US009233086B2

(12) United States Patent
Wang et al.

(10) Patent No.: US 9,233,086 B2
(45) Date of Patent: Jan. 12, 2016

(54) INHIBITION OF WDR5 INTERACTION WITH ITS BINDING PARTNERS

(75) Inventors: Shaomeng Wang, Saline, MI (US); Hacer Karatas, Ann Arbor, MI (US); Yali Dou, Ann Arbor, MI (US); Elizabeth Townsend, Ann Arbor, MI (US); Denzil Bernard, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 609 days.

(21) Appl. No.: 13/160,086

(22) Filed: Jun. 14, 2011

(65) Prior Publication Data

US 2011/0312997 A1    Dec. 22, 2011

Related U.S. Application Data

(60) Provisional application No. 61/355,449, filed on Jun. 16, 2010.

(51) Int. Cl.
*A61K 31/155* (2006.01)
*A61K 31/166* (2006.01)
*A61K 31/16* (2006.01)
*A61K 31/165* (2006.01)
*A61K 31/167* (2006.01)
*A61K 31/4164* (2006.01)
*A61K 31/445* (2006.01)

(52) U.S. Cl.
CPC .............. *A61K 31/16* (2013.01); *A61K 31/165* (2013.01); *A61K 31/166* (2013.01); *A61K 31/167* (2013.01); *A61K 31/4164* (2013.01); *A61K 31/445* (2013.01)

(58) Field of Classification Search
CPC .... A61K 31/155; A61K 31/166; A61K 31/16
See application file for complete search history.

(56) References Cited

U.S. PATENT DOCUMENTS

| 2003/0109458 A1 | 6/2003 | Haviv et al. |
| 2007/0142287 A1* | 6/2007 | Taghizadeh ..................... 514/12 |
| 2009/0215986 A1 | 8/2009 | Epstein et al. |

FOREIGN PATENT DOCUMENTS

| JP | 06220088 A | 8/1994 |
| WO | WO-2007/080194 A2 | 7/2007 |

OTHER PUBLICATIONS

Gorin et al. J. Med. Chem., 1980, vol. 23, pp. 1113-1122.*
International Search Report in international application No. PCT/US2011/040326, dated Feb. 17, 2012.
Argiropoulos, B., et al., "Hox Genes in Hematopoiesis and Leukemogenesis." *Oncogene* 2007, 26, 6766-6776.
Case, D.A., et al., Amber 9. In University of California: San Francisco, 2006.
Couture, J. F., et al., "Molecular Recognition of Histone H3 by the WD40 Protein WDR5." *Nat Struct Mol Biol* 2006, 13, 698-703.
De Vita, G., et al., "Expression of Homeobox Containing Genes in Primary and Metastatic Colorectal Cancer." *Eur J Cancer* 1993, 29A, 887-893.
Dou, Y., et al., "Regulation of MLL1 H3K4 Methyltransferase Activity by its Core Components." *Nat Struct Mol Biol* 2006, 13, 713-719.
Faber, J., et al., HOXA9 is Required for Survival in Human MLL Rearranged Acute Leukemias. *Blood* 2009, 113, 2375-2385.
Ferrando, A. A., et al., "Gene Expression Signatures in MLL Rearranged T-lineage and B-Precursor Acute Leukemias: Dominance of HOX Dysregulation." *Blood* 2003, 102, 262-268.
Guenther, M. G., et al., "Global and Hox Specific Roles for the MLL1 Ethyltransferase." *Proc/Natl Acad. Sci. USA* 2005, 102, 8603-8608.
Han, Z., et al., "Structural Basis for the Specific Recognition of Methylated Histone H3 Lysine 4 by the WD-40 Protein WDR5." *Mol Cell* 2006, 22, 137-144.
Harper, D. P., et al., "Chromosomal Rearrangements Leading to MLL Gene Fusions: Clinical and Biological Aspects." *Cancer Res* 2008, 68, 10024-10027.
Hess, J. L., "MLL: a Histone Methyltransferase Disrupted in Leukemia." *Trends Mol Med* 2004, 10, 500-507.
Hombria, J. C., et al., "Beyond Homeosis—HOX Function in Morphogenesis and Organogenesis." *Differentiation* 2003, 71, 461-476.
Hsieh, J. J., et al., Proteolytic Cleavage of MLL Generates a Complex of N and C Terminal Fragments That Confers Protein Stability and Subnuclear Localization. *Mol Cell Biol* 2003, 23, 186-194.
Huntsman, D. G., et al., "MLL2, the Second Human Homolog of the *Drosophila Trithorax* Gene, Maps to 19q13.1 and is Amplified in Solid Tumor Cell Lines." *Oncogene* 1999, 18, 7975-7984.
Jenuwein, T., et al., "Translating the Histone Code." *Science* 2001, 293, 1074-1080.
Jude, C. D., et al., "Unique and Independent Roles for MLL in adult Hematopoietic Stem Cells and Progenitors." *Cell Stem Cell* 2007, 1, 324-337.
Kouzarides, T., "Chromatin modifications and Their Function." *Cell* 2007, 128, 693-705.
Maulbecker, C. C., et al., "The Oncogenic Potential of Deregulated Homeobox Genes." *Cell Growth Differ* 1993, 4, 431-441.
Mishra, B. P., et al., "Dynamic Association of MLL1, H3K4 Trimethylation with Chromatin and Hox Gene Expression During the Cell Cycle." *FEBS J* 2009, 276, 1629-1640.
Monier, B., et al., "Downstream of Homeotic Genes: in the Heart of Hox Function." *Fly* (Austin) 2007, 1, 59-67.
Nikolovska Coleska, Z., et al., Development and Optimization of a Binding Assay for the XIAP BIR3 Domain Using Fluorescence Polarization. *Anal Biochem* 2004, 332, 261-273.
Patel, A., et al., A Conserved Arginine Containing Motif Crucial for the Assembly and Enzymatic Activity of the Mixed Lineage Leukemia Protein-1 Core Complex. *J Biol Chem* 2008, 283, 32162-32175.
Patel, A., et al., On the Mechanism of Multiple Lysine Methylation by the Human Mixed Lineage Leukemia Protein 1 (MLL1) Core Complex. *J Biol Chem* 2009, 284, 24242-24256.

(Continued)

*Primary Examiner* — Samira Jean-Louis
(74) *Attorney, Agent, or Firm* — Marshall, Gerstein & Borun LLP

(57) ABSTRACT

Peptidomimetics that inhibit the interaction between MLL1 and WDR5 are disclosed. Methods of inhibiting MLL1 activity and methods of treating cancers also are disclosed.

16 Claims, 2 Drawing Sheets

(56) References Cited

OTHER PUBLICATIONS

Patel, A., et al., "Structure of WDR5 Bound to Mixed Lineage Leukemia Protein-1 Peptide." *J Biol Chem* 2008, 283, 32158-32161.

Ruault, M., et al., "MLLE, a New Human Member of the TRX/MLL Gene Family, Maps to 7q36, a Chromosome Region Frequently Deleted in Myeloid Leukaemia." *Gene* 2002, 284, 73-81.

Ruthenburg, A. J., et al., "Histone H3 Recognition and Presentation by the WDR5 Module of the MLL1 Complex." *Nat Struct Mol Biol* 2006, 13, 704-712.

Schuetz, A., et al., "Structural Basis for Molecular Recognition and Presentation of Histone H3 by WDR5." *EMBO J* 2006, 25, 4245-4252.

Shilatifard, A., "Molecular Implementation and Physiological Roles for Histone H3 Lysine 4 (H3K4) methylation." *Curr Opin Cell Biol* 2008, 20, 341-348.

Sims, R. J., et al., "Histone H3 Lys 4 Methylation: Caught in a Bind?" *Genes Dev* 2006, 20, 2779-2786.

Song, J. J., et al., "WDR5 Interacts with Mixed Lineage Leukemia (MLL) Protein Via the Histone H3 Binding Pocket." *J Biol Chem* 2008, 283, 35258-35264.

Trievel, R. C., et al., "WDR5, a Complexed Protein." *Nat Struct Mol Biol* 2009, 16, 678-680.

Waltregny, D., et al., Overexpression of the Homeobox Gene HOXC8 in Human Prostate Cancer Correlates with Loss of Tumor Differentiation. *Prostate* 2002, 50, 162-169.

Wysocka, J., et al., "A PHD Finger of NURF Couples Histone H3 Oysine 4 Trimethylation with Chromatin Remodelling." *Nature* 2006, 442, 86-90.

Wysocka, J., et al., WDR5 Associates with Histone H3 Methylated at K4 and is Essential for H3 K4 Methylation and Vertebrate Development. *Cell* 2005, 121, 859-872.

\* cited by examiner

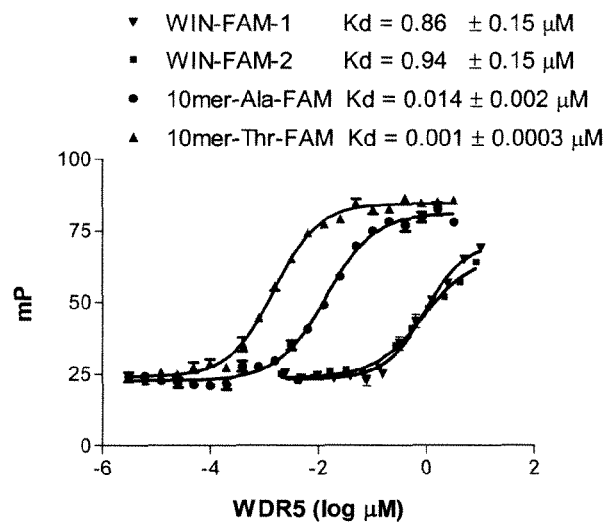
Figure 1. Saturation binding experiments with 0.6 nM tracer.
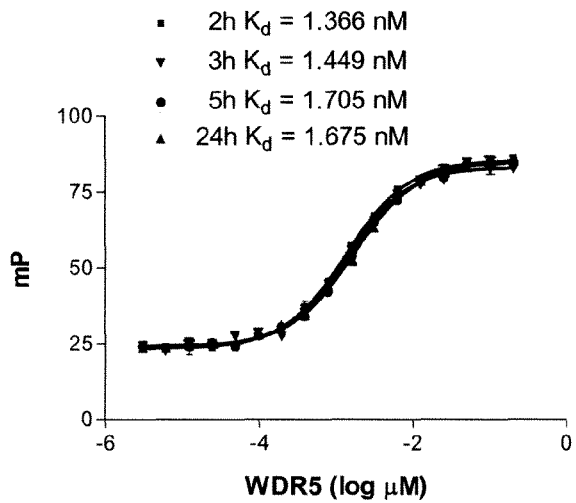
Figure 2. Stability of the saturation binding experiment with 10mer-Thr-FAM over 24 hours.

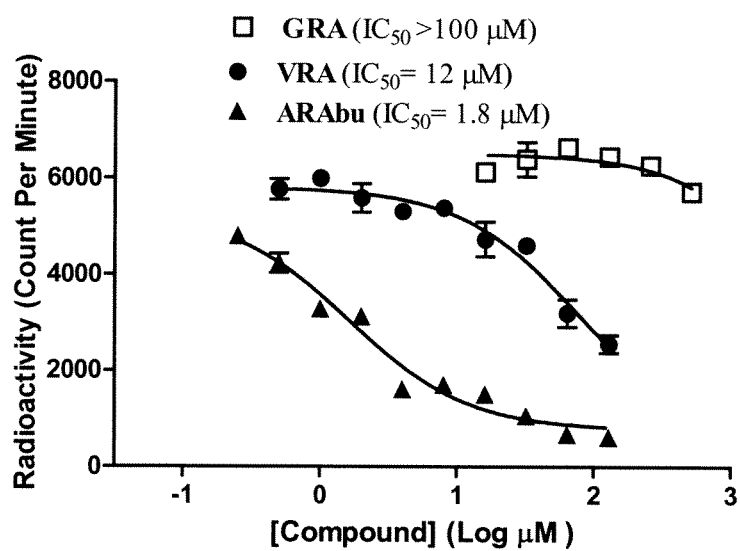
Figure 3. Inhibition of histone methyltransferase activity of the reconstituted MLL1 core complex.

INHIBITION OF WDR5 INTERACTION WITH ITS BINDING PARTNERS

CROSS REFERENCE TO RELATED APPLICATIONS

This application claims the benefit of U.S. provisional patent application No. 61/355,449, filed Jun. 16, 2010, incorporated herein by reference in its entirety.

FIELD OF THE INVENTION

The present invention relates to peptidomimetic inhibitors of interactions between WDR5 (WD Repeat Domain 5) and its binding partners that interact with the Arg binding site of WDR5. More particularly, the present invention relates to peptidomimetic compounds that block MLL (mixed lineage leukemia) binding to WDR5. The present invention relates to modulation of activity resulting from a WDR5 interaction with its binding partners, including but not limited to, activity of H3-K4 (Histone 3 Lysine 4) methylating complexes that results in H3-K4 methylation and expression of genes targeted by those complexes. The present invention also relates to the treatment of diseases and conditions related to interactions between WDR5 and its binding partners including, but not limited to, MLL.

BACKGROUND OF THE INVENTION

Histones are important in the organization of DNA into a chromatin structure and in the retrieval of genetic information. Specific modifications on histones regulate gene activity, leading to either expression or silence(1,2). Of the modifications in the euchromatins of eukaryotes that have been examined, Histone 3-Lysine 4 (H3-K4) trimethylation is recognized as a hallmark of transcriptionally active genes(3). It is believed that trimethylated H3-K4 is a recognition site for the recruitment of additional factors required for transcription (4,5). Abnormalities in H3-K4 methylating enzymes have been observed in various cancers, (6,7) the most prominent example of which is Mixed Lineage Leukemia (MLL) (8), which is also known as MLL1, ALL-1, HRX, and HTRX1.

MLL is enzymatically active in a multiprotein complex and acts as both a global and a specific gene regulator(9,10). The most well-known targets for MLL are the homeobox (Hox) genes such as Hox-a9 and Hox-c8. These genes encode for a class of homeodomain transcriptional factors that regulate organ formation during embryo development, as well as proper hematopoiesis in adults(11-13). Increased expression levels of certain Hox genes, accompanied by MLL aberrations, such as gene fusion and amplification, are frequently observed in acute leukemias, such as acute lymphoblastic leukemia (ALL) and acute myeloid leukemia (AML)(14-16). Injection of cells overexpressing Hox-a7 and Hox-c8 into nude mice results in well vascularized tumors in 4-5 weeks (17). Abnormal Hox gene expression also is observed in solid tumors, such as prostate carcinoma and primary colorectal tumors(18,19). MLL therefore is a promising therapeutic target for several forms of leukemias and solid tumors.

Immediately after translation, MLL is proteolytically cleaved to yield 180-kDa C-terminus (MLL1$^C$) and 320-kDa N-terminus fragments (MLL1$^N$)(20). These are assembled together in a multi-subunit complex together with several other proteins, including WD Repeat Domain 5 (WDR5), Absent Small or Homeotic-Like (Ash2L), and Retinoblastoma Binding Protein 5 (RbBP5), each of which is a common component of all known human H3-K4 methylating complexes.

MLL forms a catalytically active core complex with WDR5, RbBP5, and Ash2L that can dimethylate H3-K4 in vitro(21). Although MLL alone can minimally partially monomethylate H3-K4, all the other members of the core complex are required for dimethylation, including WDR5, which forms a bridge between MLL and the remainder of the core complex. In the absence of WDR5, MLL is unable to associate with RbBP5 and Ash2L, and fails to dimethylate H3-K4 in vitro(21,22). Knock-down of WDR5 is known to result in a significant decrease in the levels of H3-K4 trimethylation and expression of Hox-a9 and Hox-c8 genes in 293 cells(23). Blocking of the WDR5-MLL interaction therefore is an effective strategy for inhibiting MLL activity.

It recently has been shown that MLL binds to WDR5 via an arginine (Arg) (residue 3765) containing sequence (24,25), which is similar to that used by the N-terminal of H3 in its interaction with WDR5(26-29). WDR5 has a canonical conformation that contains a central cavity, and both H3 and MLL peptides use an Arg residue to interact with this cavity through the arginine binding site. Although crystal structures show that H3 and MLL peptides have very similar binding modes to WDR5 in this arginine binding site, MLL peptides have a higher affinity to WDR5 than H3 peptides(30). The MLL-derived, 12-residue WIN (WDR5 Interacting Motif) peptide (residues 3762-3773) (Table 1) has been shown to dissociate MLL from the remainder of the complex in vitro (21). The WIN peptide therefore represents a starting point for the design of inhibitors to block the interaction of MLL with WDR5.

TABLE 1

Sequence of WIN peptide and N-terminus of H3 peptide. Residues 1-10 in H3 and 3762-3773 in MLL1 are shown. The numbering assigned below compares the residues in these two peptides.

| | | | | | | | | | | | |
|---|---|---|---|---|---|---|---|---|---|---|---|
| WIN | G | S | A | R | A | E | V | H | L | R | K | S |
| N-term of H3 | | | A | R | T | K | Q | T | A | R | K | S |
| Numbering used herein | -2 | -1 | 1 | 2 | 3 | 4 | 5 | 6 | 7 | 8 | 9 | 10 |

Abbreviations: G—Gly—Glycine; S—Ser—Serine; A—Ala—Alanine; R—Arg—Arginine; T—Thr—Threonine; E—Glu—Glutamic acid; K—Lys—Lysine; V—Val—Valine; G—Gln—Glutamine; H—His—Histidine; L—Leu—Leucine.

Despite the availability of the crystal structures of H3 and MLL1 peptides complexed with WDR5, the essential key binding elements in MLL1 required for its high-affinity binding to WDR5 have not been defined, nor were the key structural features responsible for the large binding affinity difference between MLL1 and H3 peptides to WDR5. Elucidating these binding elements and structural features would be an important advance in the art, and provide novel therapeutic approaches to diseases and conditions mediated by an MLL1-WDR5 interaction.

SUMMARY OF THE INVENTION

The present invention is directed to compounds capable of inhibiting interactions of WDR5 with its binding partners through the Arg binding site in WDR5. More particularly, the present invention is directed to peptidomimetics that inhibit binding of MLL1 to WDR5. The present invention also is directed to the treatment of diseases and conditions that are mediated by the MLL-WDR5 interaction.

One aspect of the present invention relates to peptidomimetic compounds having a general formula (I):

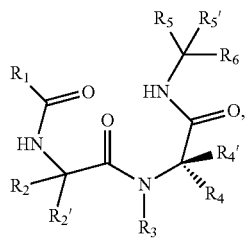

wherein $R_1$ is selected from the group consisting of H; substituted or unsubstituted $C_{1-9}$ straight chain or branched alkyl, $C_{3-7}$ cycloalkyl; —$(CH_2)_n$—U, wherein U is substituted or unsubstituted phenyl or heteroaryl and n=0-6; —Y—$R_1'$, wherein Y is O or NX and $R_1'$ and X, independently, are selected from the group consisting of H, substituted or unsubstituted $C_{1-9}$ straight chain or branched alkyl, or $C_{3-7}$ cycloalkyl, —$(CH_2)_n$—U, wherein U is substituted or unsubstituted phenyl or heteroaryl and n=0-6;

$R_2$, $R_2'$, $R_5$ and $R_5'$, independently, are selected from the group consisting of —H; $C_{1-9}$ substituted or unsubstituted straight chain or branched alkyl, $C_{3-7}$ cycloalkyl; —$(CH_2)_n$—U, wherein U is substituted or unsubstituted phenyl or heteroaryl and n=0-6; —C(A)(B)(D) wherein A is selected from the group consisting of —H, —OH, —$OCH_3$, —$NH_2$, —$NHCH_3$, —$N(CH_3)_2$, —SH, —$SCH_3$, and B and D, independently, are selected from the group consisting of H, substituted or unsubstituted $C_{1-6}$ straight chain or branched alkyl, $C_{3-7}$ cycloalkyl, —$(CH_2)_n$—U, wherein U is substituted or unsubstituted phenyl or heteroaryl and n=0-6; or $R_2$ and $R_2'$ together with the carbon atom to which they are attached can form a $C_{3-7}$ carbocyclic ring; or $R_5$ and $R_5'$ together with the carbon atom to which they are attached can form a $C_{3-7}$ carbocyclic ring or $R_5$ and $R_5'$ are null;

$R_3$ is H or substituted or unsubstituted $C_{1-6}$ straight chain or branched alkyl, or $C_{3-7}$ cycloalkyl;

$R_4$ is —H, —$(CH_2)_n$-E, arylE, or

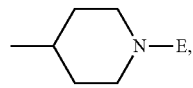

wherein n=2-6 and E is selected from the group consisting of —$NH_2$, —$NHCH_3$, —$N(CH_3)_2$, —$N^+(CH_3)_3$, —FL-C(=NJ)NKK', —FL-C(=O)NKK', and —FL-C(=S)NKK', wherein F is $C_{1-6}$alkyl, N, or CH, and L, J, K, K', independently, are H or —$CH_3$;

$R_4'$ is —H, a $C_{1-6}$ straight chain or branched alkyl, or $C_{3-7}$cycloalkyl, each unsubstituted or substituted with one or more halogen or OH;

$R_6$ is selected from the group consisting of —H; substituted or unsubstituted $C_{1-12}$ straight chain or branched alkyl, $C_{3-7}$ cycloalkyl; —C(=O)N(M)Q, wherein M and Q, independently, are selected from the group consisting of —H, $C_{1-12}$ straight chain or branched alkyl, $C_{3-7}$ cycloalkyl, phenyl, benzyl, or heteroaryl, wherein each optionally is substituted with one or more of —OH, —$OCH_3$, —$NH_2$, —$NHCH_3$, —$N(CH_3)_2$ or halogen, and —$(CH_2)_n$CPP'P''' wherein n=0-6 and P, P', and P''', independently, are selected from the group consisting of unsubstituted or substituted phenyl, benzyl, or heteroaryl, or M and Q together with the nitrogen atom to which they are attached can form a 3 to 8 membered ring; or a pharmaceutically acceptable salt or hydrate thereof.

Another aspect of the present invention is to provide peptidomimetics that inhibit WDR5 interactions with its binding partners through the arginine binding site in WDR5, i.e., where MLL and H3 proteins bind to WDR5. This embodiment includes, but is not limited to, inhibition of WDR5-MLL and WDR5-H3 interactions using the peptidomimetics of general formula (I).

Yet another aspect of the present invention is to provide a method of treating a disease or condition wherein inhibition of an interaction between WDR5 and its binding partners, including, but not limited to, MLL, provides a benefit. The method comprises administering of a therapeutically effective amount of a peptidomimetic compound of the present invention to an individual in need thereof. The peptidomimetic compound can be administered as the sole therapy, or in conjunction with a therapeutically effective amount of a second agent known to be useful in the treatment of the disease or condition of interest. For example, the disease or condition can be a cancer, and the second agent is a second anticancer agent, such as radiation and/or chemotherapy.

Another aspect of this invention relates to modulation of H3K4 methylation activity of the histone methyl transferase complexes in which WDR5 participates. Inhibition of WDR5 interactions with its binding partners, which is required for the activity of H3K4 methylating complexes, results in disrupting their ability to methylate their targets.

Still another aspect of the present invention relates to modulation of gene expression which is controlled through H3K4 methylation. This embodiment includes, but is not limited to, Meis 1 and Hox genes, in particular HoxA9, HoxA7, and HoxC8.

Another aspect of the present invention is to provide a method of treating a leukemia, such as acute lymphoblastic leukemia (ALL) and acute myeloid leukemia (AML), or a solid tumor, such as prostate carcinoma and primary colorectal tumors, by administering a therapeutically effective amount of a present peptidomimetic inhibitor of the MLL1-WDR5 interaction to an individual in need thereof.

Still another aspect of the present invention is to provide a peptidomimetic compound for use in therapy. Yet another aspect of the present invention is to provide a peptidomimetic compounds for use in a cancer therapy, such as leukemia therapy or a solid tumor therapy.

In another aspect, the present invention provides a pharmaceutical composition comprising a present peptidomimetic compound and a pharmaceutically acceptable excipient.

Another aspect of the present invention is to utilize a peptidomimetic composition comprising a compound of structural formula (I) and a second therapeutically active agent in a method of treating an individual for a disease or condition wherein inhibition of WDR5-MLL and WDR-L3 interactions provides a benefit.

In a further embodiment, the invention provides for use of a composition comprising a peptidomimetic compound of structural formula (I) and an optional second therapeutic agent for the manufacture of a medicament for treating a disease or condition of interest, e.g., a cancer.

Still another aspect of the present invention is to provide a kit for human pharmaceutical use comprising (a) a container, (b1) a packaged composition comprising a present peptidomimetic compound, and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition of interest.

Another aspect of the invention is to provide fluorescently labeled tracers for WDR5 for the accurate and quantitative evaluation of the binding affinities of various compounds to WDR5. Compounds of the invention inhibit the MLL1-WDR5 interactions and therefore also are useful research tools for in vitro study of histones and their role in biological processes.

These and other aspects and features of the present invention will become apparent from the following drawings and detailed description of the preferred embodiments.

BRIEF DESCRIPTION OF THE DRAWINGS

FIG. 1 contains plots of mP vs. WDR5 (log μM) for saturation binding experiments using 0.6 nM fluorescent tracers;

FIG. 2 contains plots of mP vs. WDR5 (log μM) showing stability of the saturation binding experiments with 10mer-Thr-FAM over 24 hours; and FIG. 3 contains plots of radioactivity (count per minute) vs. compound concentration (log μM) showing inhibition of histone methyltransferase activity.

DETAILED DESCRIPTION OF THE PREFERRED EMBODIMENTS

The present invention is described in connection with preferred embodiments. It should be appreciated that the invention is not limited to these disclosed embodiments. It is understood that, given the description of the embodiments of the invention herein, various modifications can be made by a person skilled in the art. Such modifications are encompassed by the claims below.

As used herein, the terms "treat," "treating," "treatment," and the like refer to eliminating, reducing, or ameliorating a disease or condition and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms, and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; and/or relieve, to some extent, one or more of the symptoms associated with the cancer. To extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration" and similar phrases mean that two or more agents are administered concurrently to the subject being treated. By "concurrently," it is meant that each agent is administered simultaneously or sequentially in any order at different points in time. However, if not administered simultaneously, they are, in one aspect, administered sufficiently closely in time so as to provide the desired treatment effect of the combination of agents. Suitable dosing intervals and dosing order of the agents will be readily apparent to those skilled in the art. It also is contemplated that two or more agents are administered from separate compositions, and in one aspect, one composition is administered prior to administration of the other composition. Prior administration refers to administration of the agents within one day (24 hours). It is further contemplated that one agent is administered subsequent to administration of the other agent. Subsequent administration is meant to describe administration from 30 minutes of the second agent up to one day (24 hours) after administration of the first agent. Within 24 hours may include administration after 30 minutes, 1, 2, 3, 4, 5, 6, 7, 8, 9, 10, 11, 12, 16, 20, or 24 hours.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

The term "binding partner" as used herein means compounds, oligomers, polymers, proteins, and related entities that interact with, e.g., bind, with the Arg binding site of WDR5.

The present invention is directed to peptidomimetic compounds have the structural formula (I):

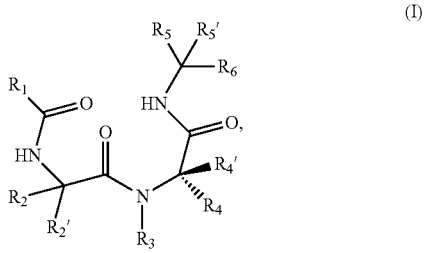

(I)

wherein R₁ is selected from the group consisting of H; substituted or unsubstituted $C_{1-9}$ straight chain or branched alkyl, $C_{3-7}$ cycloalkyl; —$(CH_2)_n$—U, wherein U is substituted or unsubstituted phenyl or heteroaryl and n=0-6; —Y—$R_1'$, wherein Y is O or NX and $R_1'$ and X, independently, are selected from the group consisting of H, substituted or unsubstituted $C_{1-9}$ straight chain or branched alkyl, or $C_{3-7}$ cycloalkyl, —$(CH_2)_n$—U, wherein U is substituted or unsubstituted phenyl or heteroaryl and n=0-6;

$R_2$, $R_2'$, $R_5$ and $R_5'$, independently, are selected from the group consisting of —H; $C_{1-9}$ substituted or unsubstituted straight chain or branched alkyl, $C_{3-7}$ cycloalkyl; —$(CH_2)_n$—U, wherein U is substituted or unsubstituted phenyl or heteroaryl and n=0-6; —C(A)(B)(D) wherein A is selected from the group consisting of —H, —OH, —$OCH_3$, —$NH_2$, —$NHCH_3$, —$N(CH_3)_2$, —SH, —$SCH_3$, and B and D, independently, are selected from the group consisting of H, substituted or unsubstituted $C_{1-6}$ straight chain or branched alkyl, $C_{3-7}$ cycloalkyl, —$(CH_2)_n$—U, wherein U is substituted or unsubstituted phenyl or heteroaryl and n=0-6; or $R_2$ and $R_2'$ together with the carbon atom to which they are attached can form a $C_{3-7}$ carbocyclic ring; or $R_5$ and $R_5'$ together with the carbon atom to which they are attached can form a $C_{3-7}$ carbocyclic ring or $R_5$ and $R_5'$ are null;

$R_3$ is H or substituted or unsubstituted $C_{1-6}$ straight chain or branched alkyl, or $C_{3-7}$ cycloalkyl;

$R_4$ is —H, $C_{1-6}$alkyl, —$(CH_2)_n$-E, arylE, or

wherein n=2-6 and E is selected from the group consisting of —$NH_2$, —$NHCH_3$, —$N(CH_3)_2$, —$N^+(CH_3)_3$, —FL-C(=NJ)NKK', —FL-C(=O)NKK', and —FL-C(=S)NKK', wherein F is $C_{1-6}$alkyl, N, or CH, and L, J, K, K', independently, are H or —$CH_3$;

$R_4'$ is —H, a $C_{1-6}$ straight chain or branched alkyl, or $C_{3-7}$cycloalkyl, each unsubstituted or substituted with one or more halogen or OH;

$R_6$ is selected from the group consisting of —H; substituted or unsubstituted $C_{1-12}$ straight chain or branched alkyl, $C_{3-7}$ cycloalkyl; —C(=O)N(M)Q, wherein M and Q, independently, are selected from the group consisting of —H, $C_{1-12}$ straight chain or branched alkyl, $C_{3-7}$ cycloalkyl, phenyl, benzyl, or heteroaryl, wherein each optionally is substituted with one or more of —OH, —$OCH_3$, —$NH_2$, —$NHCH_3$, —$N(CH_3)_2$ or halogen, and —$(CH_2)_n$CP'P'P''' wherein n=0-6 and P, P', and P''', independently, are selected from the group consisting of unsubstituted or substituted phenyl, benzyl, or heteroaryl, or M and Q together with the nitrogen atom to which they are attached can form a 3 to 8 membered ring;

or a pharmaceutically acceptable salt or hydrate thereof.

As used herein, the term "alkyl" refers to straight chained and branched saturated hydrocarbon groups, nonlimiting examples of which include methyl, ethyl, and straight chain and branched propyl, butyl, pentyl, and hexyl groups. The term $C_{n-y}$ means the alkyl group has "n" to "y" carbon atoms. An alkyl group can be substituted with halo, trifluoromethyl, trifluoromethoxy, hydroxy, alkoxy, nitro, cyano, alkylamino, or amino groups, for example.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four, groups independently selected from, for example, halo, alkyl, alkenyl, —$OCF_3$, —$NO_2$, —CN, —NC, —OH, alkoxy, amino, alkylamino, —$CO_2H$, —$CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, —$(CH_2)_{1-4}$halo, alkenyl, —$CF_3$, —$OCF_3$, —$NO_2$, —CN, —NC, —OH, alkoxy, —$(CH_2)_{1-4}$OR, —$CO_2NR_2$, amino, —$CO_2H$, —$CO_2$alkyl, —SR, —$SO_2R$, —$SO_3R$, aryl, and heteroaryl. Examples of heteroaryl groups include, but are not limited to, thienyl, furyl, oxazolyl, quinolyl, thiophenyl, isoquinolyl, indolyl, triazinyl, triazolyl, isothiazolyl, isoxazolyl, imidazolyl, benzothiazolyl, pyrimidinyl, thiazolyl, thiadiazolyl, pyridinyl, pyridazinyl, pyrazolyl, pyrazinyl, quinolyl, tetrazolyl, oxazolyl, pyrrolyl, benzimidazolyl, benzofuranyl, cinnolinyl, indazolyl, indolizinyl, phthalazinyl, triazinyl, isoindolyl, purinyl, oxadiazolyl, furazanyl, benzofurazanyl, benzothiophenyl, benzotriazolyl, benzothiazolyl, benzisothiazolyl, benzoxazolyl, benzisoxazolyl, benzimidazolyl, quinazolinyl, quinoxalinyl, napththyridinyl, dihydroquinolyl, tetrahydroquinolyl, dihydroisoquinolyl, tetrahydroisoquinolyl, benzofuryl, furopyridinyl, pyrrolopyrimidinyl, and azaindolyl.

As used herein, groups such as

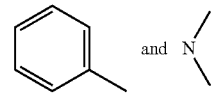

are abbreviations for

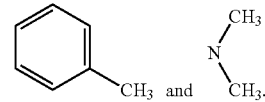

As used herein, the term "$C_{3-9}$cycloalkyl" means a monocylic aliphatic ring containing three to nine carbon atoms.

In various embodiments, $R_1$ is H, $C_{1-4}$alkyl, $C_{3-5}$cycloalkyl, —$NH(C_{1-3}$alkyl), aryl, or —$CH_2$aryl. In some preferred embodiments $R_1$ is $CH_3$—, —$CH(CH_3)_2$, —$CH_2CH_3$, —$CH_2CH_2CH_3$, —$(CH_2)_3CH_3$, cyclopropyl, cyclobutyl, cyclopentyl, phenyl, benzyl, or —$NH(CH_3)$.

In various embodiments, $R_2$ and $R_2'$, independently, are H, $C_{1-4}$alkyl, —$(CH_2)_{1-2}$SH, $C_{3-6}$cycloalkyl, —$CH_2$-heteroaryl, —$CH_2$aryl, or —$C_{1-4}$alkyleneOH, or $R_2$ and $R_2'$ are taken together with the carbon to which they are attached to form a $C_4$ to $C_6$ Spiro structure. In some embodiments, $R_2$ is H and $R_2'$ is H, $C_{1-4}$alkyl, —$(CH_2)_{1-2}$SH, $C_{2-6}$cycloalkyl, —$CH_1$-heteroaryl, —$CH_2$aryl, —$C_{1-4}$alkyleneOH, or phenyl. In other embodiments, $R_2$ and $R_2'$ each are $C_{1-4}$alkyl. In some preferred embodiments, $R_2$ and $R_2'$, independently, are H, —$CH_3$, —$CH_2CH_3$, —$CH(CH_3)_3$, —$(CH_2)_2CH_3$, —$C(CH_3)_2$, —$CH_2SH$, —$CH_2CH(CH_3)_2$, cyclopentyl, cyclohexyl,

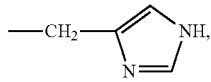

—$CH_2$-phenyl, —$CH_2OH$, —$CH(OH)CH_3$, or $R_2$ and $R_2'$ are taken together with the carbon to which they are attached to form a Spiro $C_3$, $C_4$, $C_5$, or $C_6$ moiety. In other preferred embodiments, $R_2$ is H and $R_2'$ is $CH_3$ or both $R_2$ and $R_2'$ are —$CH_2CH_3$.

In some preferred embodiments, $R_3$ is H.

In various embodiments, $R_4$ is H, —$(CH_2)_n$—FH—C(=NJ)NKK', aryl-FH—C(=NJ)NKK',

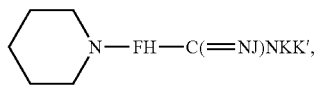

$C_{1-4}$alkyl, or —$(CH_2)_n NH_2$. In some preferred embodiments, $R_4$ is H,

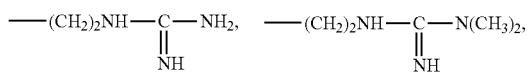

—$(CH_2)_3CH_3$, —$(CH_2)_{3-4}NH_2$,

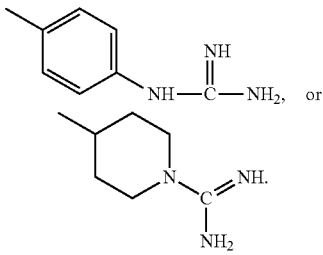

In various embodiments, $R_4'$ is H, —$(CH_2)_n$FH—C(=NJ)NKK', or aryl-FH—C(=NJ)NKK'. In some preferred embodiments, $R_4'$ is H,

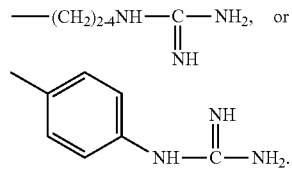

In various embodiments, $R_5$ and $R_5'$, independently, are null, H, $C_{1-4}$alkyl, —$(CH_2)_{1-3}SH$, —$(CH_2)_{1-3}OH$, $C_{3-6}$cycloalkyl, —$CH_2$aryl, —$CH(OH)CH_3$, —$(CH_2)_{1-3}CO_2H$, aryl optionally halo substituted, or $R_5$ and $R_5'$ are taken together with the carbon to which they are attached to form a $C_3$ to $C_6$ Spiro moiety. In some preferred embodiments, $R_5$ and $R_5'$, independently, are null, H, —$CH_3$, —$CH_2CH_3$, —$CH(CH_3)_2$, —$CH_2SH$, —$CH_2OH$, —$CH_2CH(CH_3)_2$,

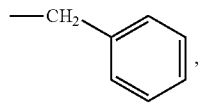

—$CH(OH)CH_3$, —$C(CH_2)_3$, cyclohexyl, —$(CH_2)_2CO_2H$, cyclopentyl, or $R_5$ and $R_5'$ are taken together with the carbon to which they are attached to form a $C_3$, $C_4$, $C_5$, or $C_6$ spiro moiety.

In various embodiments, $R_6$ is —C(=O)N(M)(O), wherein M and Q, independently, are H, $C_{1-8}$alkyl, aryl, —$(CH_2)_{1-4}$aryl, —CH(aryl)$_2$ optionally halo substituted, —CH(CH$_3$)aryl, or $C_{3-6}$cycloalkyl. In preferred embodiments, $R_6$ is —C(=O)N(M)(O) wherein M and Q, independently, are H, —$CH_3$, —$CH_2CH_3$, —$CH(CH_3)_2$, —CH(CH$_2$CH$_3$)$_2$, cyclohexyl, cyclopentyl,

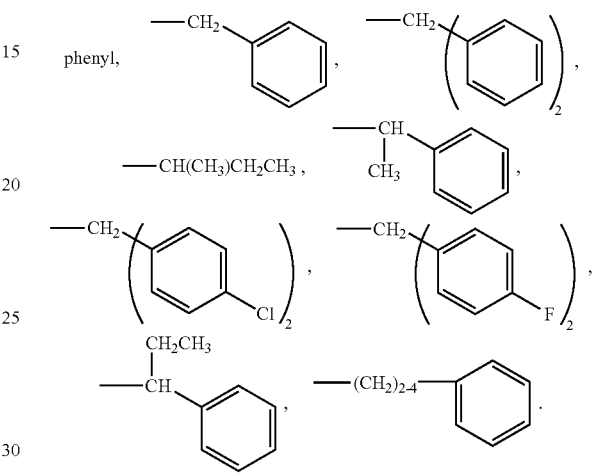

In several embodiments, both M and Q are H or $C_{1-4}$alkyl. In other embodiments, one of M and Q is H and the other is different from H.

Peptidomimetic compounds of the invention can exist as salts. In some embodiments, pharmaceutically acceptable salts of the peptidomimetic compounds may be preferred in the methods of the invention. As used herein, the term "pharmaceutically acceptable salts" refers to salts or zwitterionic forms of the peptidomimetic compounds. Salts of the compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In light of the foregoing, any reference to compounds of the present invention appearing herein is intended to include the peptidomimetic compounds as well as pharmaceutically acceptable salts and hydrates thereof.

As previously discussed, mixed lineage leukemia 1 (MLL1) is a Histone 3-Lysine 4 (H3-K4) methyltransferase and is a cancer therapeutic target. The catalytic activity of MLL1 is regulated by the formation of a core complex consisting of MLL1, WDR5, RbBP5, and Ash2L. The interaction between WDR5 and MLL1 plays an essential role in regulation of the H3-K4 methyltransferase activity of MLL1 and targeting this interaction represents an attractive therapeutic strategy.

In accordance with the present invention, the essential elements in MLL1 required for its high-affinity binding to WDR5 have been found. A systematic analysis of the interaction of MLL1 and H3 peptides with WDR5 was performed, and it was found that in the MLL1 derived peptides, —CO-Ala-Arg-Ala-NH— is the minimum motif for their high-affinity bonding to WDR5. The analysis further shows that intramolecular hydrogen bonds formed within this motif play a role for the high affinity bonding to WDR5.

The absence of one of these intramolecular hydrogen bonds in H3 peptides is responsible for their weak bonding affinity to WDR5. In particular, wild-type H3 peptide (i.e., ARTKQTARKS) with a free N-terminal has a $K_i$ value of 15 μM to WDR5, but introduction of an acetyl group at its N-terminal to provide the missing intramolecular hydrogen bond improves the binding affinity by greater than 10,000 times, and the resulting peptide has a $K_i$ value of less than 1 nM. In one embodiment of the invention, two 3-mer peptides, Ac-ARA-NH$_2$ and Ac-ART-NH$_2$, were prepared and exhibited $K_i$ values of 120 nM and 20 nM to WDR5, respectively. This discovery provides a solid basis for the use of peptidomimetic compounds to inhibit MLL1 activity by targeting the MLL1 and WDR5 interaction.

More particularly, the minimal motif in MLL1 for high-affinity binding to WDR5 first was determined. The MLL1 peptide containing the WIN sequence has been shown to bind to WDR5 with a $K_d$ of 0.12 μM(21). To identify the residues required for the high-affinity binding, residues were systematically deleted, whose numbering is given in Table 1, from either the N-terminus or the C-terminus of the WIN peptide (i.e., Ac-GSRAREVHLRKS—NH$_2$). Unless stated otherwise, all the peptides produced were acetylated at the N-terminus and capped with amide at the C-terminus. The binding affinity of each of the peptides to WDR5 was measured by a fluorescence polarization (FP) based competitive binding assay. The data are summarized in Table 2.

After determining the essential elements required of a peptidomimetic to bind to MLL1 and thereby disrupt an MLL1-WDR5 interaction, the present peptidomimetic inhibitors of the MLL1-WDR5 interaction were designed, synthesized, and tested.

TABLE 2

Binding affinities of truncated MLL peptides to WDR5.

| Peptide | Formula | IC$_{50}$ ± SD (μM) | Ki ± SD (μM) |
|---|---|---|---|
| WIN | Ac-GSARAEVHLRKS-NH$_2$ | 0.75 ± 0.10 | 0.16 ± 0.02 |
| Ac-11mer | Ac-SARAEVHLRKS-NH$_2$ | 1.04 ± 0.14 | 0.20 ± 0.03 |
| Ac-10mer | Ac-ARAEVHLRKS-NH$_2$ | 0.02 ± 0.004 | 0.003 ± 0.001 |
| H$_2$N-11mer | H$_2$N-SARAEVHLRKS-NH$_2$ | 0.08 ± 0.01 | 0.02 ± 0.002 |
| Ac-9mer | Ac-RAEVHLRKS-NH$_2$ | 29 ± 4 | 6.30 ± 0.80 |
| Ac-7mer | Ac-ARAEVHL-NH$_2$ | 0.16 ± 0.03 | 0.03 ± 0.01 |
| Ac-6mer | Ac-ARAEVH-NH$_2$ | 0.40 ± 0.10 | 0.09 ± 0.02 |
| Ac-5mer | Ac-ARAEV-NH$_2$ | 0.75 ± 0.10 | 0.16 ± 0.03 |
| Ac-4mer | Ac-ARAE-NH$_2$ | 0.40 ± 0.05 | 0.08 ± 0.01 |
| Ac-3mer | Ac-ARA-NH$_2$ | 0.54 ± 0.03 | 0.12 ± 0.01 |
| Ac-2mer | Ac-AR-NH$_2$ | 125 ± 6 | 27 ± 1.4 |

Ac is acetyl (H$_3$C—CO—) at the N-terminal of the peptides and peptide analogues.

As seen in Table 2, the 12-residue WIN peptide has a $K_i$ value of 0.16 μM, which is similar to the reported values(21, 24). Removal of the Gly from the −2 position did not significantly affect the binding. Surprisingly, further deletion of Ser from the −1 position in the 11-residue peptide (Ac-11 mer) resulted in a highly potent 10-residue peptide (Ac-10mer), which has $K_i$=3 nM, 50 times more potent than that of the WIN peptide. It also was found that the N-terminal acetyl group in Ac-11 mer is detrimental to its binding to WDR5. The H$_2$N-11mer peptide with a free N-terminus is 10-times more potent than Ac-11mer. Further deletion of Ala1 from Ac-10mer, giving Ac-9mer, decreases the binding affinity by 1500 times.

The sequence from the C-terminus was truncated starting from Ac-10mer. Simultaneous deletion of Arg8, Lys9, and Ser10, residues unresolved in the co-crystal structure of WIN-WDR5 complex, led to the Ac-7mer, which has a 10-fold lower binding affinity than the Ac-10mer(25). Further stepwise deletions from the C-terminus generated the Ac-6mer, Ac-5mer, Ac-4-mer, and Ac-3mer, all of which have binding affinities similar to the 12-residue WIN peptide. However, removal of Ala3 from the Ac-3mer peptide results in a greater than 200-fold loss of binding affinity to WDR5. Therefore, it was discovered that the Ac-3mer (Ac-ARA-NH$_2$) is the shortest MLL1 peptide to achieve high-affinity binding to WDR5.

The role of intramolecular hydrogen bonds in MLL1 peptides for high-affinity binding to WDR5 also was investigated. In the crystal structure of the WDR5-WIN complex, two intramolecular hydrogen bonds are present in the main chain of the WIN peptide(25). The first is between the Ser carbonyl at the −1 position and the amide proton of Ala3, and the second is between the Ala1 carbonyl and the Glu4 amide proton. These intramolecular hydrogen bonds allow the peptide to adopt a 3$_{10}$ helical secondary structure, and it is theorized that this conformation may contribute to the binding affinity of the WIN peptide to WDR5. Ac-ARA-NH$_2$ exhibits a binding affinity similar to that of the 12mer WIN peptide, and this 3mer maintains these two intramolecular hydrogen bonds.

To determine the effect of the hydrogen bonds, hydrogen bond 1 was disrupted either by removing the acetyl group from Ala1 or by methylating the Ala3 nitrogen. Removal of the acetyl group from the N-terminal Ala1 of the Ac-3mer peptide yields the H$_2$N-3mer, which does not bind to WDR5 up to the concentrations tested (Table 3). To further demonstrate the influence of this hydrogen bond, the acetyl group from the most potent Ac-10mer peptide also was removed, and a greater than 1500-fold decrease in binding affinity was observed. A similar fold loss of binding affinity was observed when the N-terminal acetyl group was removed from the Ac-7mer, Ac-6mer, and Ac-5mer peptides.

Methylation of the Ala3 nitrogen (peptide Δ1), which also disrupts hydrogen bond 1, led to a complete loss of its binding to WDR5. Next, the methyl group from the N-terminal acetyl was removed, yielding the CHO-ARA-NH$_2$ peptide (CHO-3mer), in order to determine the contribution of a carbonyl in the absence of methyl. Replacement of the acetyl by a formyl group decreases the binding affinity by a factor of 25, suggesting that the methyl group in the N-terminal acetyl contributes to the increase in binding affinity, albeit to a smaller extent. Together, these data show that hydrogen bond 1 plays an important role in maintaining the high binding affinities of these potent MLL1 peptides to WDR5.

TABLE 3

Binding affinities of peptide analogues of Ac-ARA-NH$_2$

| Peptide | Formula | IC$_{50}$ ± SD (μM) | K$_i$ ± SD (μM) |
|---|---|---|---|
| Ac-10mer | Ac-ARAEVHLRKS-NH$_2$ | 0.02 ± 0.004 | 0.003 ± 0.001 |
| H$_2$N-10mer | H$_2$N-ARAEVHLRKS-NH$_2$ | 34 ± 3 | 7.30 ± 0.70 |
| Ac-3mer | Ac-ARA-NH$_2$ | 0.54 ± 0.03 | 0.12 ± 0.01 |
| H$_2$N-3mer | H$_2$N-ARA-NH$_2$ | >300 | >50 |
| CHO-3mer | CHO-ARA-NH$_2$ | 14.9 ± 1.4 | 3.20 ± 0.3 |
| Δ1 | Ac-AR-(N—Me)A-NH$_2$ | >300 | >50 |

TABLE 3-continued

Binding affinities of peptide analogues of Ac-ARA-NH$_2$

| Peptide | Formula | IC$_{50}$ ± SD (μM) | K$_i$ ± SD (μM) |
|---|---|---|---|
| Δ2a | Ac-ARA-CONHMe | 0.70 ± 0.14 | 0.15 ± 0.03 |
| Δ2b | Ac-ARA-CONMe$_2$ | 30 ± 5 | 6.50 ± 1.20 |
| Δ2c | Ac-ARA-COOCH$_3$ | 7.30 ± 0.80 | 1.60 ± 0.20 |

N—Me is N-Methyl Ala 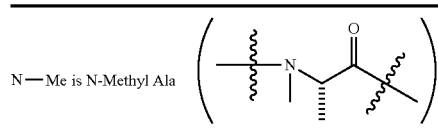

To perturb hydrogen bond 2, the C-terminal amide was mono- or dimethylated using Ac-3mer (Table 3). The monomethylated derivative (Δ2a) was shown by modeling to maintain hydrogen bond 2 in its bound conformation, and has K$_i$=0.15 μM, similar to that of Ac-3mer. However, the dimethylated derivative (Δ2b) is 50 times less potent than Ac-3mer. Replacement of the C-terminal amide group with a methyl ester provided Δ2c, which is 10 times less potent than Ac-3mer. These data indicate that while hydrogen bond 2 makes an important contribution to the binding affinity of Ac-3mer increasing it by perhaps an order of magnitude, it is less critical than hydrogen bond 1.

The binding of H3 peptides to WDR5 also was investigated. While H3 and MLL1 peptides have similar binding modes to WDR5, H3 peptides show much weaker affinities than MLL1 peptides(30).

The H3 peptides have an ART binding motif similar to the ARA binding motif in the MLL1 peptides, but possess a free amino group at the Ala1 residue. To investigate whether this free amino group is responsible for weaker H3 binding affinities, the H3-3mer and H3-10mer peptides were acetylated (Table 4). In both cases, acetylation of the free amino group increased binding affinities to WDR5 significantly (1500 times for Ac—H3-3mer and greater than 10,000 times for Ac—H3-10mer). The Ac—H3-3mer and Ac—H3-10mer peptides have K$_i$ values of 20 nM and less than 1 nM, respectively, to WDR5, and both also are more potent than the corresponding MLL1 peptides Ac-3mer and Ac-10mer (Table 3 and Table 4). The data show that the primary feature underlying the weaker binding affinities of H3 peptides to WDR5 is the free amino group in Ala1 and the absence of intramolecular hydrogen bond 1.

It also was examined whether methylation of Lys4 (K4) significantly changes the binding affinity of H3-10mer to WDR5. Mono-, di-, or tri-methylation of K4 led to no significant difference in the binding affinity to WDR5 compared to that of H3-10mer (Table 4). This is consistent with experiments using an isothermal titration curve measurement(28).

TABLE 4

Binding affinities of histone 3 peptides to WDR5.

| Peptide | Formula | IC$_{50}$ ± SD (μM) | Ki ± SD (μM) |
|---|---|---|---|
| H3-10mer | H$_2$N-ARTKQTARKS-NH$_2$ | 70 ± 6 | 15.10 ± 1.30 |
| Ac-H3-10mer | Ac-ARTKQTARKS-NH$_2$ | 0.006 ± 0.002 | <0.001 |
| H3-3mer | H$_2$N-ART-NH$_2$ | 127 ± 12 | 27.30 ± 2.50 |
| Ac-H3-3mer | Ac-ART-NH$_2$ | 0.08 ± 0.003 | 0.02 ± 0.001 |
| H3-10mer-K4Me | H$_2$N-ARTK(Me)QTARKS-NH$_2$ | 69 ± 7 | 15.00 ± 1.60 |
| H3-10mer-K4Me$_2$ | H$_2$N-ARTK(Me$_2$)QTARKS-NH$_2$ | 42 ± 6 | 9.00 ± 1.30 |
| L3-10mer-K4Me$_3$ | H$_2$N-ARTK(Me$_3$)QTARKS-NH$_2$ | 73 ± 6 | 15.60 ± 1.20 |

K(Me) in Table 4 refers to Lys residue wherein the amine group of the side chain is monomethylated.

K(Me$_2$) in Table 4 refers to Lys residue wherein the amine group of the side chain is dimethylated.

K(Me$_3$) in Table 4 refers to Lys residue wherein the amine group of the side chain is trimethylated.

As stated above, MLL is frequently found to be unregulated in cancers, resulting in increased expression levels of Hox target genes which link MLL with its tumorigenic properties(8,32). Consequently, inhibition of MLL activity is an attractive strategy for cancer therapy.

The MLL1 protein alone has minimal enzymatic activity for the mono-methylation of H3-K4 in vitro, is incapable of di- and trimethylation, and its overall catalytic activity is dramatically enhanced when it forms a core complex with WDR5, Ash2L, and RbBP5 proteins(33). Previous studies clearly established that interaction between WDR5 and MLL1 is required for the H3-K4 catalytic activity of the MLL1 core complex(21,22). Therefore, inhibition of the WDR5-MLL1 interaction with small-molecule inhibitors can effectively inhibit the enzymatic activity of MLL1. The above-described studies show that short MLL1 peptides bind to WDR5 with a high affinity, and based upon these studies, it was concluded that —CO-ARA-NH— is the minimal motif within the WIN peptide for high-affinity binding to WDR5.

Having discovered the elements required for the high-affinity binding of MLL1 to WDR5, inhibitors of the MLL1-WDR5 interaction were designed, synthesized, and tested. In particular, based on the above-described studies, a series of 3-mers was designed and synthesized. The binding affinity of the 3-mer peptidomimetics to WDR5 also was determined. The compounds and binding affinities are summarized below (Table 5).

TABLE 5

Structure, binding affinities and ESI-Mass characterization of the compounds.

| Compound | Structure | Binding Affinity to WDR5 ($IC_{50} \pm SD$, μM) | (ESI-MS) $(M + H)^+$ |
| --- | --- | --- | --- |
| 1A | 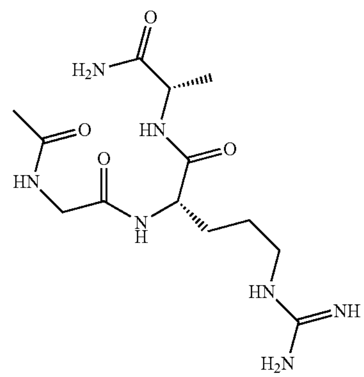 [SMILES: CC(=O)NCC(=O)N[C@@H](CCCNC(=N)N)C(=O)N[C@@H](C)C(N)=O] | >10 | 344.33 |
| 1B | 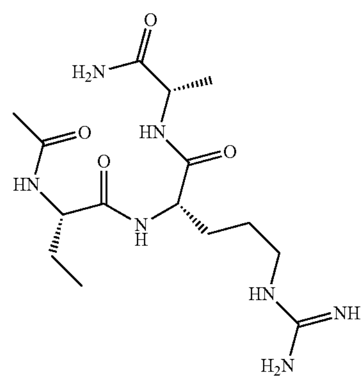 [SMILES: CC[C@H](NC(C)=O)C(=O)N[C@@H](CCCNC(=N)N)C(=O)N[C@@H](C)C(N)=O] | <1 | 372.33 |
| 1C | 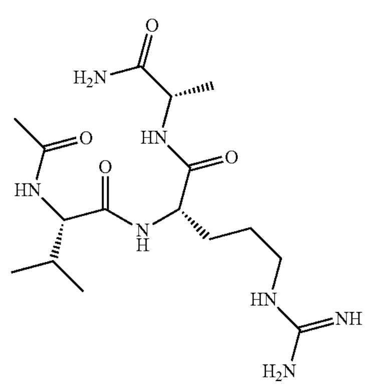 [SMILES: CC(=O)N[C@H](C(=O)N[C@@H](CCCNC(=N)N)C(=O)N[C@@H](C)C(N)=O)C(C)C] | <1 | 386.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 1D | 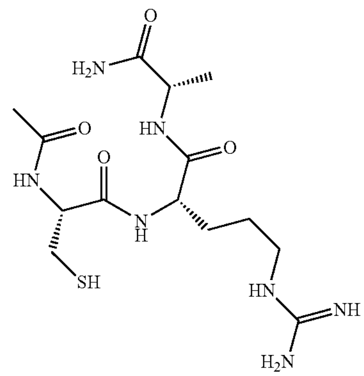 [SMILES: CC(=O)N[C@@H](CS)C(=O)N[C@@H](CCCNC(=N)N)C(=O)N[C@@H](C)C(N)=O] | <5 | 390.33 |
| 1E | 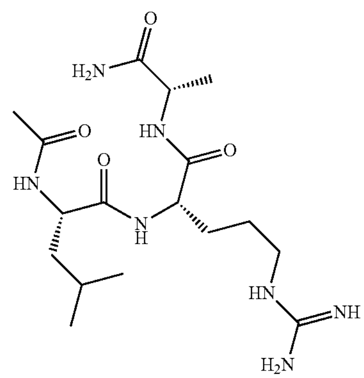 [SMILES: CC(=O)N[C@@H](CC(C)C)C(=O)N[C@@H](CCCNC(=N)N)C(=O)N[C@@H](C)C(N)=O] | <50 | 400.42 |
| 1F | 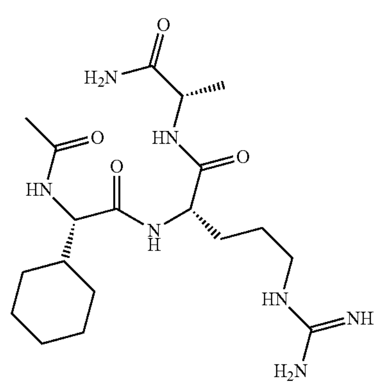 [SMILES: CC(=O)N[C@H](C(=O)N[C@@H](CCCNC(=N)N)C(=O)N[C@@H](C)C(N)=O)C1CCCCC1] | <50 | 426.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 1G | 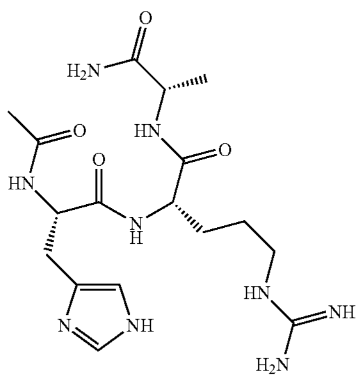 [SMILES: CC(=O)N[C@@H](Cc1c[nH]cn1)C(=O)N[C@@H](CCCNC(=N)N)C(=O)N[C@@H](C)C(N)=O] | <10 | 424.42 |
| 1H | 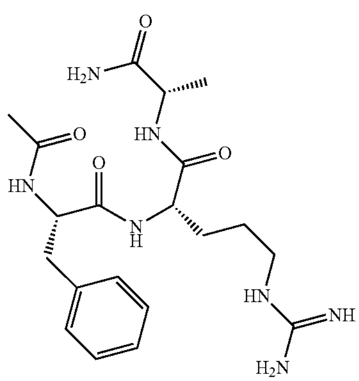 [SMILES: CC(=O)N[C@@H](Cc1ccccc1)C(=O)N[C@@H](CCCNC(=N)N)C(=O)N[C@@H](C)C(N)=O] | <50 | 434.42 |
| 1I | 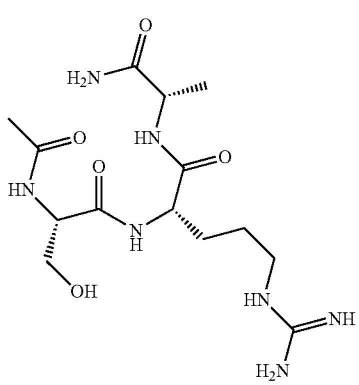 | <30 | 374.33 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
| --- | --- | --- | --- |
| 1J | 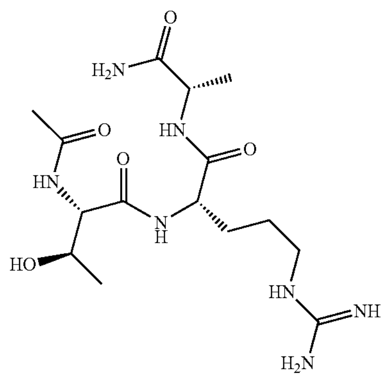 [SMILES: CC(=O)N[C@H](C(=O)N[C@@H](CCCNC(=N)N)C(=O)N[C@@H](C)C(N)=O)[C@@H](C)O] | <30 | 388.33 |
| 2A | 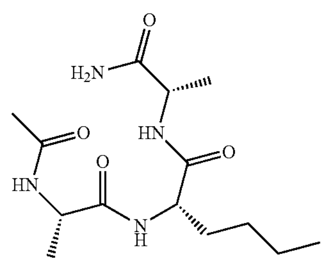 [SMILES: CCCC[C@H](NC(=O)[C@H](C)NC(C)=O)C(=O)N[C@@H](C)C(N)=O] | >1 | 315.08 |
| 2B | 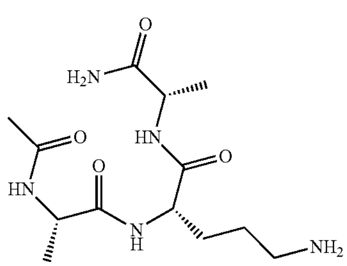 [SMILES: CC(=O)N[C@@H](C)C(=O)N[C@@H](CCCN)C(=O)N[C@@H](C)C(N)=O] | >1 | 316.17 |
| 2C | 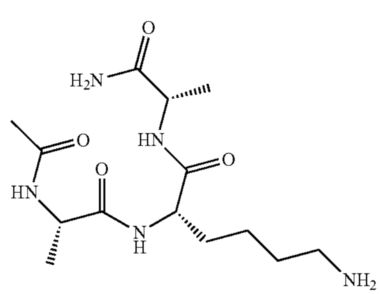 [SMILES: CC(=O)N[C@@H](C)C(=O)N[C@@H](CCCCN)C(=O)N[C@@H](C)C(N)=O] | >1 | 330.25 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 2D | 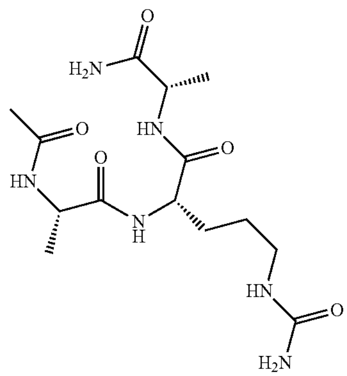 [SMILES: CC(=O)N[C@@H](C)C(=O)N[C@@H](CCCNC(N)=O)C(=O)N[C@@H](C)C(N)=O] | >1 | 359.08 |
| 2E | 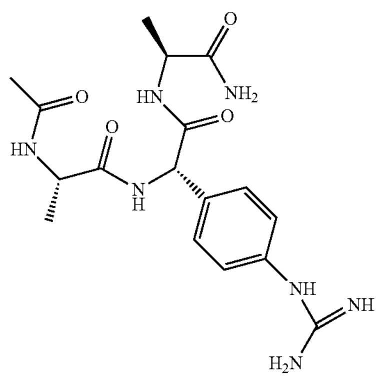 [SMILES: CC(=O)N[C@@H](C)C(=O)N[C@H](C(=O)N[C@@H](C)C(N)=O)c1ccc(NC(=N)N)cc1] | >10 | 392.83 |
| 2F | 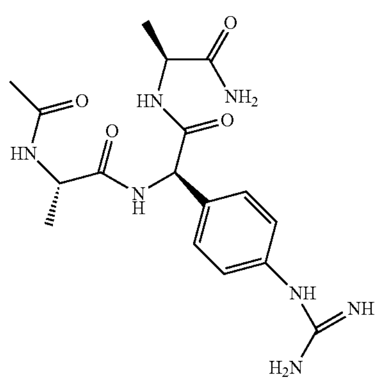 [SMILES: CC(=O)N[C@@H](C)C(=O)N[C@@H](C(=O)N[C@@H](C)C(N)=O)c1ccc(NC(=N)N)cc1] | >10 | 392.92 |
| 2G | 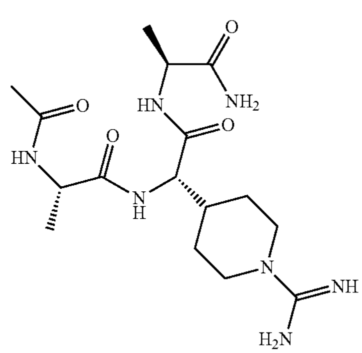 [SMILES: CC(=O)N[C@@H](C)C(=O)N[C@H](C(=O)N[C@@H](C)C(N)=O)C1CCN(C(=N)N)CC1] | >10 | 384.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 3A | 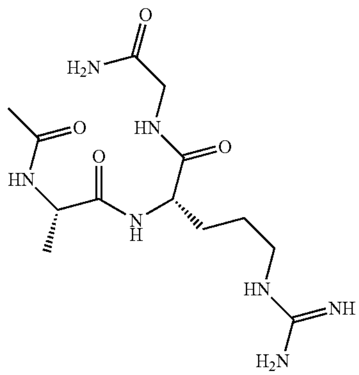 [SMILES: CC(=O)N[C@@H](C)C(=O)N[C@@H](CCCNC(=N)N)C(=O)NCC(N)=O] | >1 | 344.33 |
| 3B | 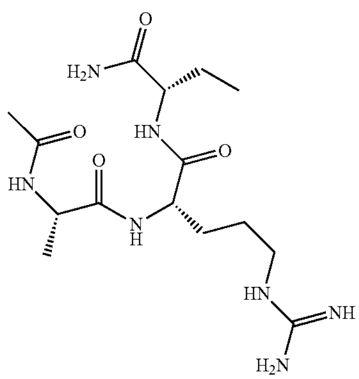 [SMILES: CC[C@H](NC(=O)[C@H](CCCNC(=N)N)NC(=O)[C@H](C)NC(C)=O)C(N)=O] | <0.1 | 372.33 |
| 3C | 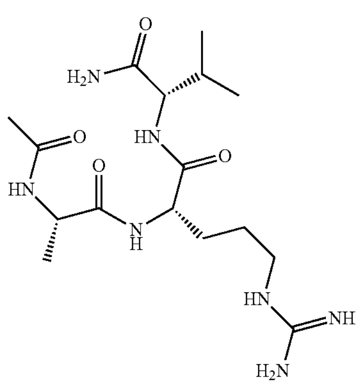 [SMILES: CC(=O)N[C@@H](C)C(=O)N[C@@H](CCCNC(=N)N)C(=O)N[C@H](C(N)=O)C(C)C] | <1 | 386.42 |

TABLE 5-continued

Structure, binding affinities and ESI-Mass characterization of the compounds.

| Compound | Structure | Binding Affinity to WDR5 (IC$_{50}$ ± SD, µM) | (ESI-MS) (M + H)$^+$ |
| --- | --- | --- | --- |
| 3D | 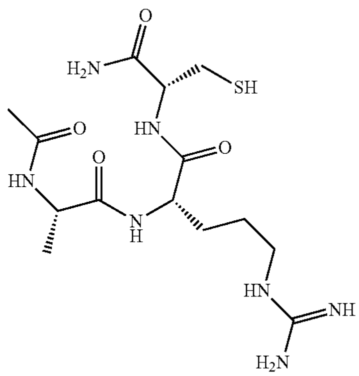 [SMILES: CC(=O)N[C@@H](C)C(=O)N[C@@H](CCCNC(=N)N)C(=O)N[C@@H](CS)C(N)=O] | <1 | 390.33 |
| 3E | 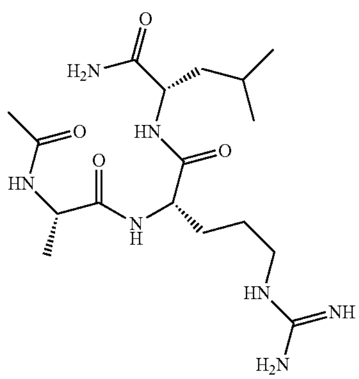 [SMILES: CC(=O)N[C@@H](C)C(=O)N[C@@H](CCCNC(=N)N)C(=O)N[C@@H](CC(C)C)C(N)=O] | >10 | 400.42 |
| 3F | 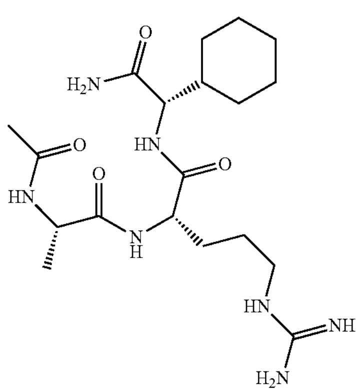 [SMILES: CC(=O)N[C@@H](C)C(=O)N[C@@H](CCCNC(=N)N)C(=O)N[C@H](C(N)=O)C1CCCCC1] | >10 | 426.42 |

TABLE 5-continued
Structure, binding affinities and ESI-Mass characterization of the compounds.
| Compound | Structure | Binding Affinity to WDR5 (IC$_{50}$ ± SD, μM) | (ESI-MS) (M + H)$^+$ |
|---|---|---|---|
| 3G | 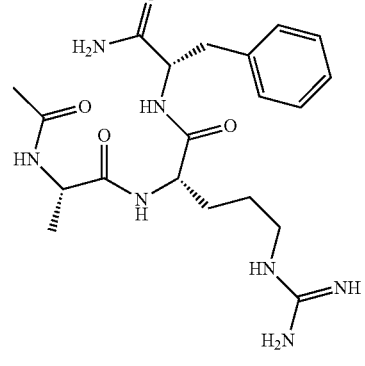 | >10 | 434.42 |
| 3H | 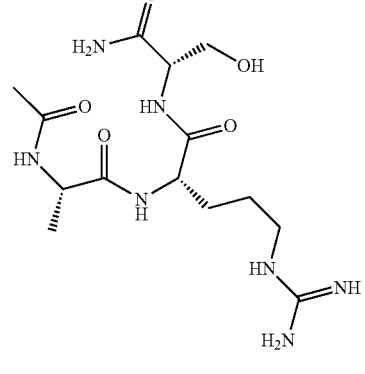 | <5 | 374.33 |
| 3I | 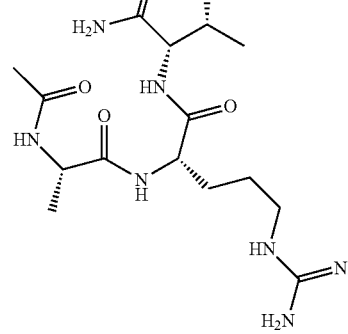 | <1 | 388.33 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 3J | 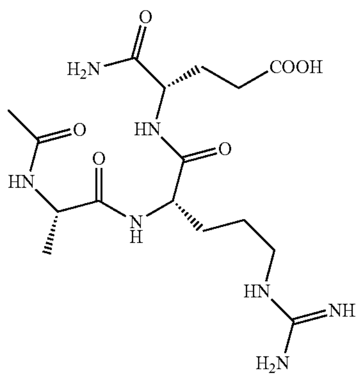 [SMILES: CC(=O)N[C@@H](C)C(=O)N[C@@H](CCCNC(=N)N)C(=O)N[C@@H](CCC(=O)O)C(N)=O] | >10 | 416.42 |
| 4A | 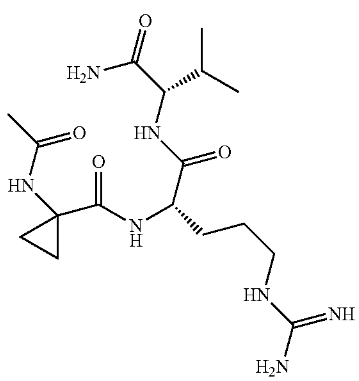 [SMILES: CC(=O)NC1(C(=O)N[C@@H](CCCNC(=N)N)C(=O)N[C@H](C(N)=O)C(C)C)CC1] | <1 | 398.20 |
| 4B | 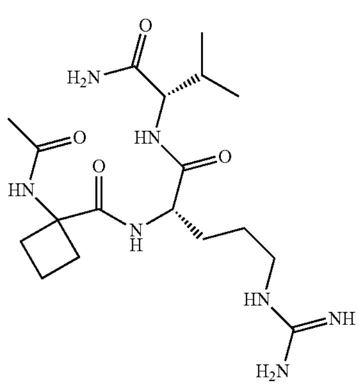 [SMILES: CC(=O)NC1(C(=O)N[C@@H](CCCNC(=N)N)C(=O)N[C@H](C(N)=O)C(C)C)CCC1] | <1 | 412.20 |

TABLE 5-continued
Structure, binding affinities and ESI-Mass characterization of the compounds.
| Compound | Structure | Binding Affinity to WDR5 (IC$_{50}$ ± SD, μM) | (ESI-MS) (M + H)$^+$ |
|---|---|---|---|
| 4C | 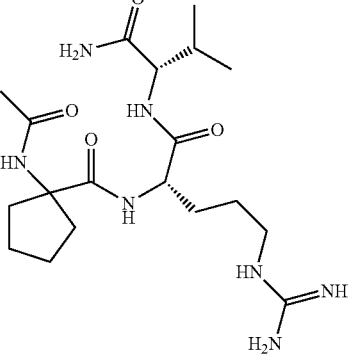 | <1 | 426.24 |
| 4D | 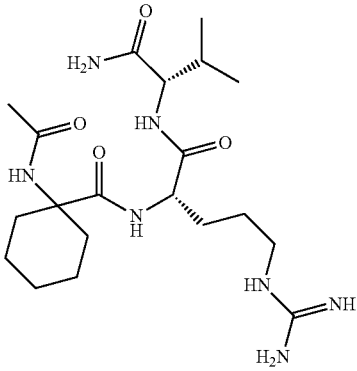 [SMILES: CC(=O)NC1(C(=O)N[C@@H](CCCNC(=N)N)C(=O)N[C@H](C(N)=O)C(C)C)CCCCC1] | <1 | 440.24 |
| 4E | 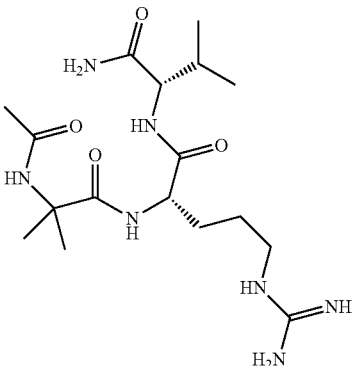 | <1 | 400.20 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 4F | 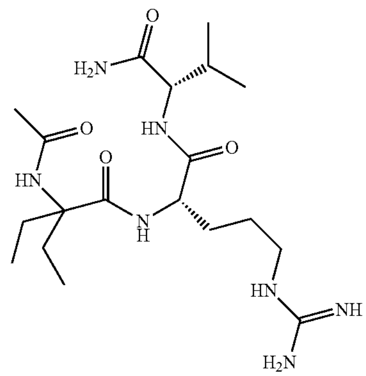 [SMILES: CCC(CC)(NC(C)=O)C(=O)N[C@@H](CCCNC(=N)N)C(=O)N[C@H](C(N)=O)C(C)C] | <1 | 428.42 |
| 4G | 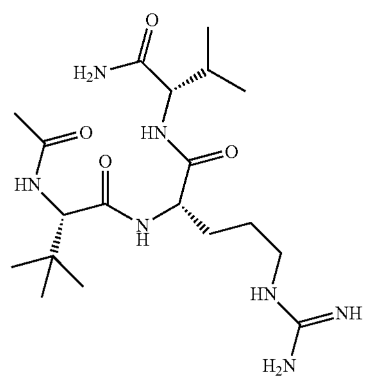 [SMILES: CC(=O)N[C@H](C(=O)N[C@@H](CCCNC(=N)N)C(=O)N[C@H](C(N)=O)C(C)C)C(C)(C)C] | <5 | 428.24 |
| 4H | 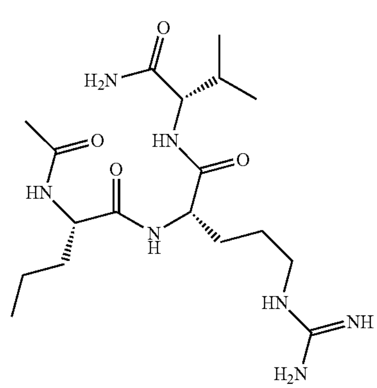 [SMILES: CCC[C@H](NC(C)=O)C(=O)N[C@@H](CCCNC(=N)N)C(=O)N[C@H](C(N)=O)C(C)C] | <1 | 414.24 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 4I | 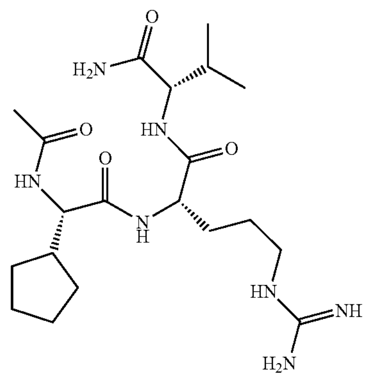 [SMILES: CC(=O)N[C@H](C(=O)N[C@@H](CCCNC(=N)N)C(=O)N[C@H](C(N)=O)C(C)C)C1CCCC1] | <10 | 440.24 |
| 4J | 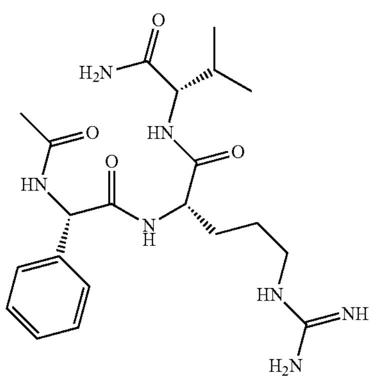 [SMILES: CC(=O)N[C@H](C(=O)N[C@@H](CCCNC(=N)N)C(=O)N[C@H](C(N)=O)C(C)C)c1ccccc1] | <30 | 448.33 |
| 4K | 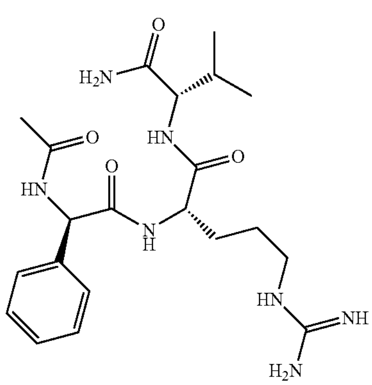 [SMILES: CC(=O)N[C@@H](C(=O)N[C@@H](CCCNC(=N)N)C(=O)N[C@H](C(N)=O)C(C)C)c1ccccc1] | >10 | 448.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
| --- | --- | --- | --- |
| 5A | 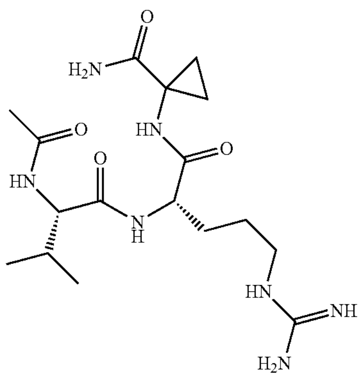 [SMILES: CC(=O)N[C@H](C(=O)N[C@@H](CCCNC(=N)N)C(=O)NC1(C(N)=O)CC1)C(C)C] | <10 | 398.33 |
| 5B | 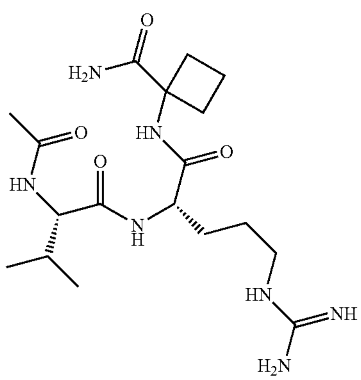 [SMILES: CC(=O)N[C@H](C(=O)N[C@@H](CCCNC(=N)N)C(=O)NC1(C(N)=O)CCC1)C(C)C] | <10 | 412.33 |
| 5C | 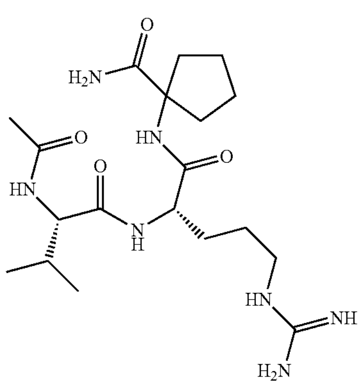 [SMILES: CC(=O)N[C@H](C(=O)N[C@@H](CCCNC(=N)N)C(=O)NC1(C(N)=O)CCCC1)C(C)C] | <1 | 426.33 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 5D | 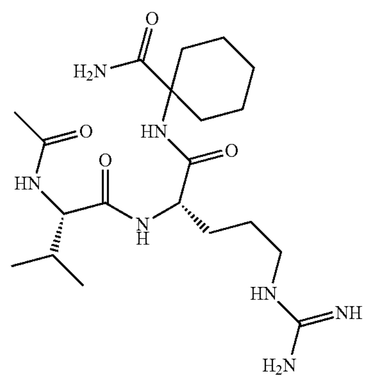 [SMILES: CC(=O)N[C@H](C(=O)N[C@@H](CCCNC(=N)N)C(=O)NC1(C(N)=O)CCCCC1)C(C)C] | <10 | 440.42 |
| 5E | 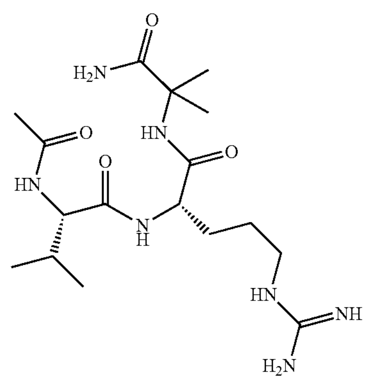 [SMILES: CC(=O)N[C@H](C(=O)N[C@@H](CCCNC(=N)N)C(=O)NC(C)(C)C(N)=O)C(C)C] | >1 | 400.33 |
| 5F | 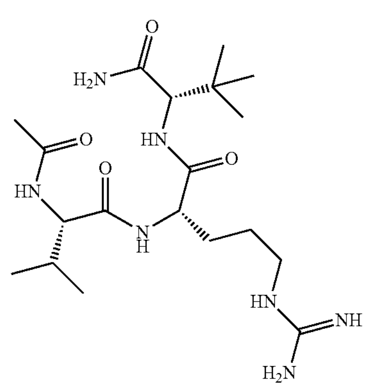 [SMILES: CC(=O)N[C@H](C(=O)N[C@@H](CCCNC(=N)N)C(=O)N[C@H](C(N)=O)C(C)(C)C)C(C)C] | >10 | 428.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 5G | 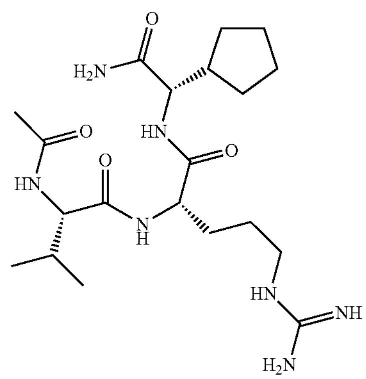 [SMILES: CC(=O)N[C@H](C(=O)N[C@@H](CCCNC(=N)N)C(=O)N[C@H](C(N)=O)C1CCCC1)C(C)C] | >10 | 440.42 |
| 6A | 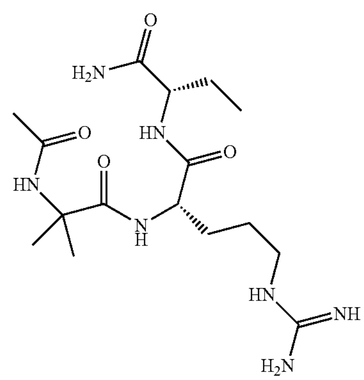 [SMILES: CC[C@H](NC(=O)[C@H](CCCNC(=N)N)NC(=O)C(C)(C)NC(C)=O)C(N)=O] | <1 | 386.33 |
| 6B | 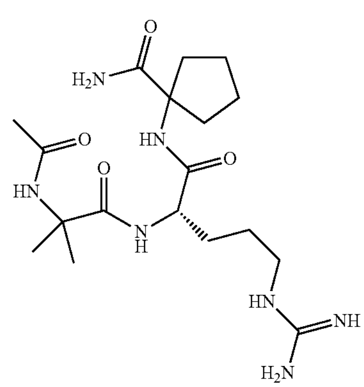 [SMILES: CC(=O)NC(C)(C)C(=O)N[C@@H](CCCNC(=N)N)C(=O)NC1(C(N)=O)CCCC1] | <1 | 412.33 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
| --- | --- | --- | --- |
| 6C | 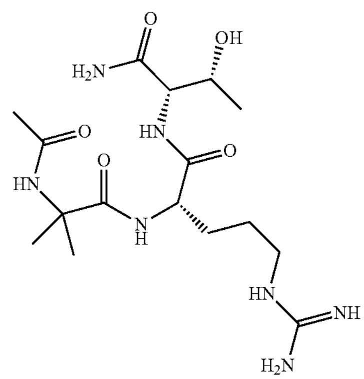 [SMILES: CC(=O)NC(C)(C)C(=O)N[C@@H](CCCNC(=N)N)C(=O)N[C@H](C(N)=O)[C@@H](C)O] | <1 | 402.42 |
| 6D | 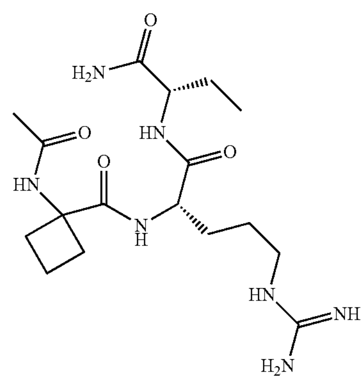 [SMILES: CC[C@H](NC(=O)[C@H](CCCNC(=N)N)NC(=O)C1(NC(C)=O)CCC1)C(N)=O] | <1 | 398.33 |
| 6E | 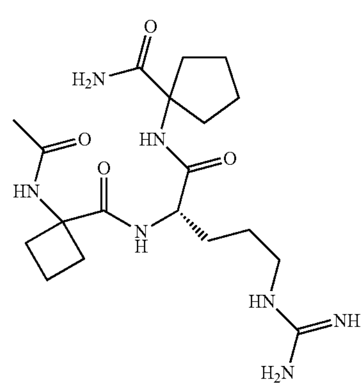 [SMILES: CC(=O)NC1(C(=O)N[C@@H](CCCNC(=N)N)C(=O)NC2(C(N)=O)CCCC2)CCC1] | <1 | 424.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 6F | 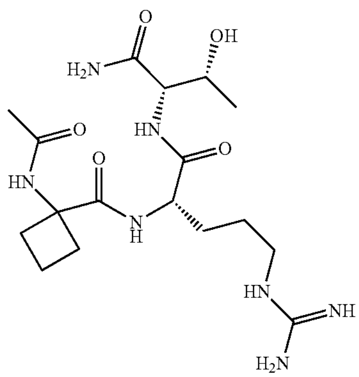 [SMILES: CC(=O)NC1(C(=O)N[C@@H](CCCNC(=N)N)C(=O)N[C@H](C(N)=O)[C@@H](C)O)CCC1] | <1 | 414.33 |
| 6G | 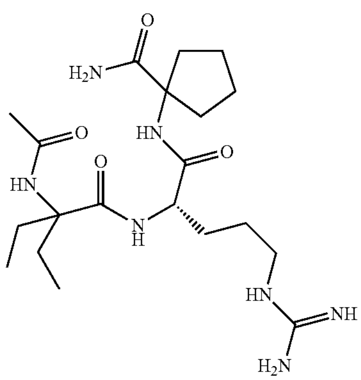 [SMILES: CCC(CC)(NC(C)=O)C(=O)N[C@@H](CCCNC(=N)N)C(=O)NC1(C(N)=O)CCCC1] | <1 | 440.41 |
| 7A | 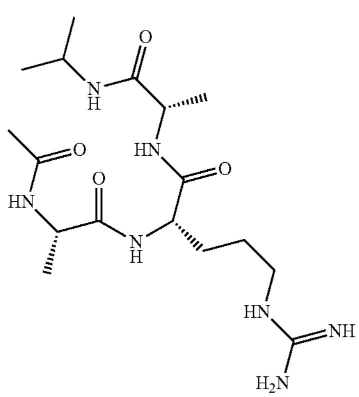 [SMILES: CC(=O)N[C@@H](C)C(=O)N[C@@H](CCCNC(=N)N)C(=O)N[C@@H](C)C(=O)NC(C)C] | <1 | 400.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 7B | 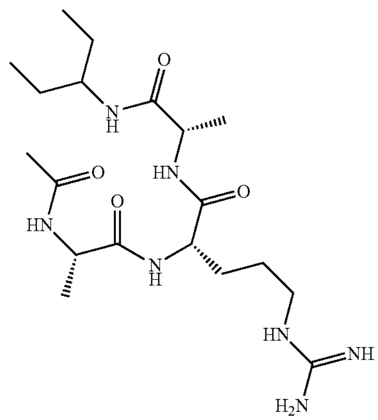 [SMILES: CCC(CC)NC(=O)[C@H](C)NC(=O)[C@H](CCCNC(=N)N)NC(=O)[C@H](C)NC(C)=O] | <1 | 428.42 |
| 7C | 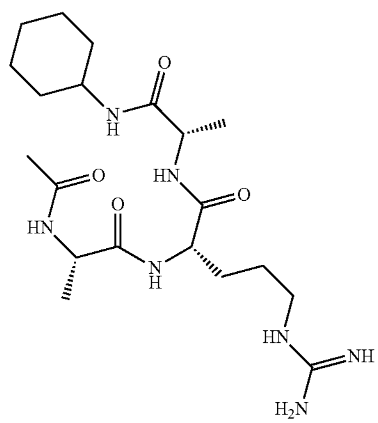 [SMILES: CC(=O)N[C@@H](C)C(=O)N[C@@H](CCCNC(=N)N)C(=O)N[C@@H](C)C(=O)NC1CCCCC1] | <1 | 440.42 |
| 7D | 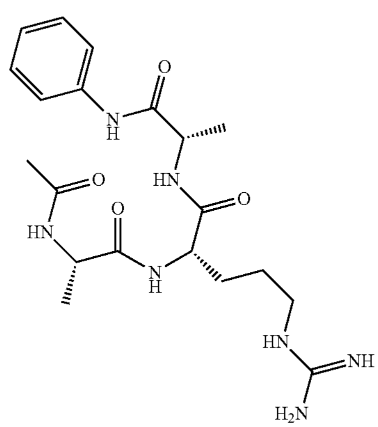 [SMILES: CC(=O)N[C@@H](C)C(=O)N[C@@H](CCCNC(=N)N)C(=O)N[C@@H](C)C(=O)Nc1ccccc1] | <1 | 434.33 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 7E | 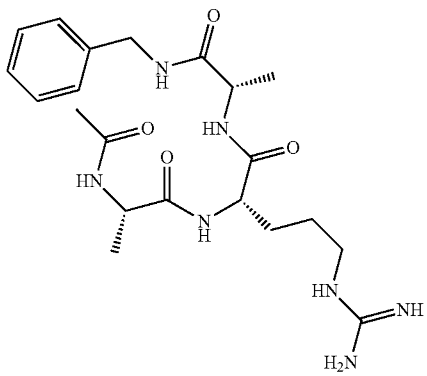 [SMILES: CC(=O)N[C@@H](C)C(=O)N[C@@H](CCCNC(=N)N)C(=O)N[C@@H](C)C(=O)NCc1ccccc1] | <1 | 448.42 |
| 7F | 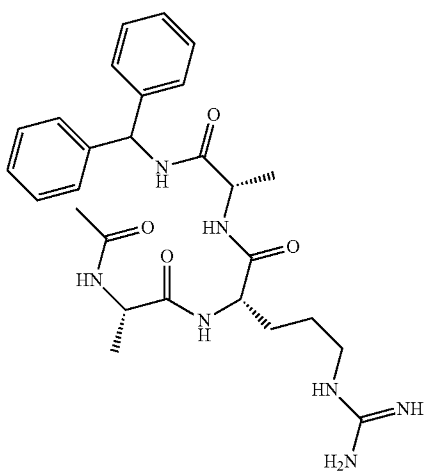 [SMILES: CC(=O)N[C@@H](C)C(=O)N[C@@H](CCCNC(=N)N)C(=O)N[C@@H](C)C(=O)NC(c1ccccc1)c1ccccc1] | <1 | 524.42 |
| 8A | 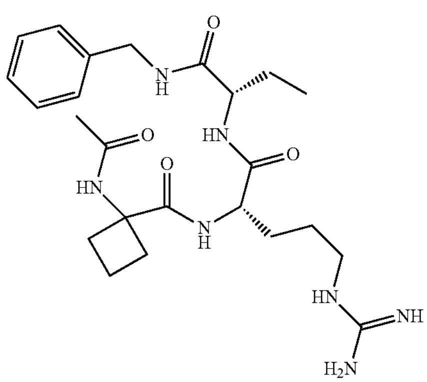 [SMILES: CC[C@H](NC(=O)[C@H](CCCNC(=N)N)NC(=O)C1(NC(C)=O)CCC1)C(=O)NCc1ccccc1] | <1 | 488.39 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 8B | 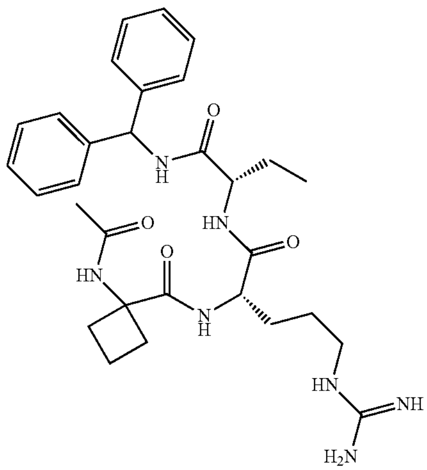 [SMILES: CC[C@H](NC(=O)[C@H](CCCNC(=N)N)NC(=O)C1(NC(C)=O)CCC1)C(=O)NC(c1ccccc1)c1ccccc1] | <1 | 564.40 |
| 9A | 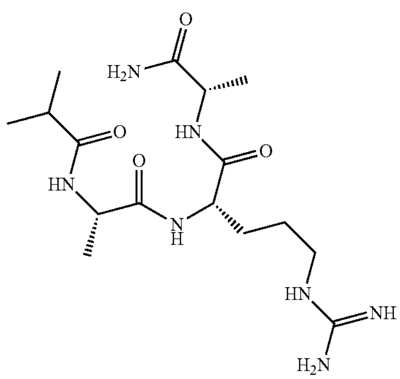 [SMILES: CC(C)C(=O)N[C@@H](C)C(=O)N[C@@H](CCCNC(=N)N)C(=O)N[C@@H](C)C(N)=O] | <1 | 386.31 |
| 9B | 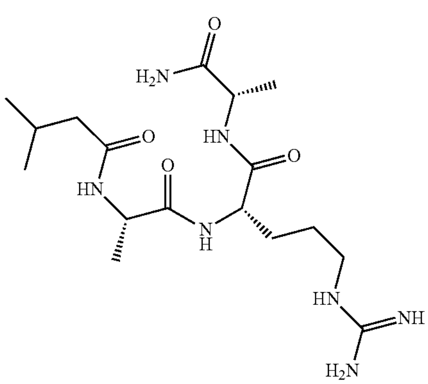 [SMILES: CC(C)CC(=O)N[C@@H](C)C(=O)N[C@@H](CCCNC(=N)N)C(=O)N[C@@H](C)C(N)=O] | >10 | 400.35 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 9C | 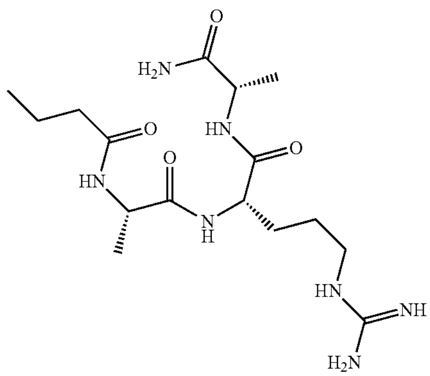 [SMILES: CCCC(=O)N[C@@H](C)C(=O)N[C@@H](CCCNC(=N)N)C(=O)N[C@@H](C)C(N)=O] | <5 | 386.42 |
| 9D | 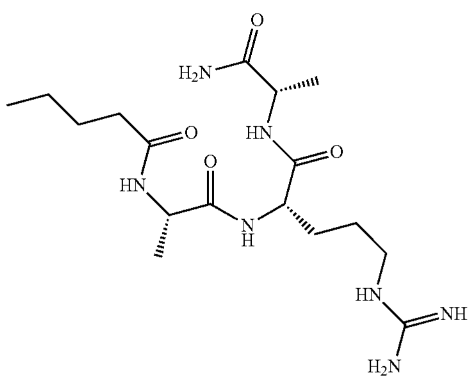 [SMILES: CCCCC(=O)N[C@@H](C)C(=O)N[C@@H](CCCNC(=N)N)C(=O)N[C@@H](C)C(N)=O] | >10 | 400.34 |
| 9E | 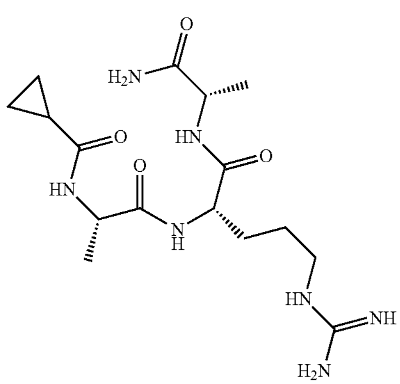 [SMILES: C[C@H](NC(=O)[C@H](CCCNC(=N)N)NC(=O)[C@H](C)NC(=O)C1CC1)C(N)=O] | <5 | 384.30 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 9F | 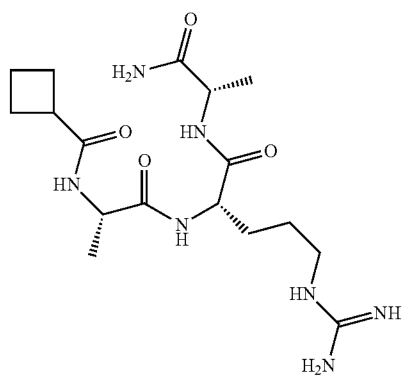 [SMILES: C[C@H](NC(=O)[C@H](CCCNC(=N)N)NC(=O)[C@H](C)NC(=O)C1CCC1)C(N)=O] | <10 | 398.33 |
| 9G | 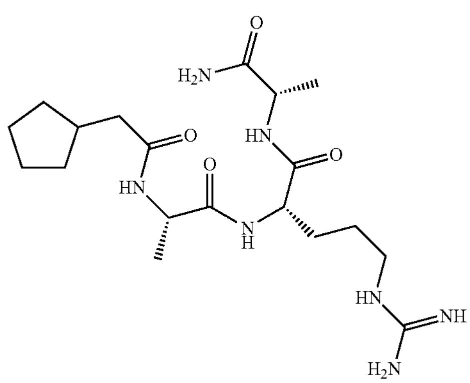 [SMILES: C[C@H](NC(=O)[C@H](CCCNC(=N)N)NC(=O)[C@H](C)NC(=O)CC1CCCC1)C(N)=O] | >1 | 426.36 |
| 9H | 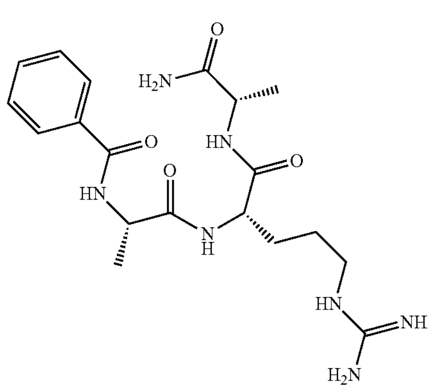 [SMILES: C[C@H](NC(=O)[C@H](CCCNC(=N)N)NC(=O)[C@H](C)NC(=O)c1ccccc1)C(N)=O] | >1 | 420.32 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
| --- | --- | --- | --- |
| 9I | 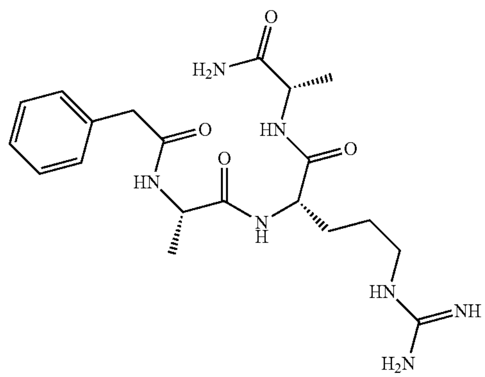 [SMILES: C[C@H](NC(=O)[C@H](CCCNC(=N)N)NC(=O)[C@H](C)NC(=O)Cc1ccccc1)C(N)=O] | >25 | 434.34 |
| 9J | 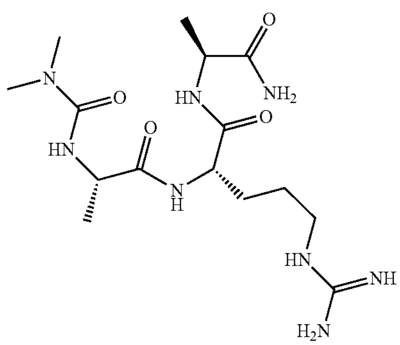 [SMILES: C[C@H](NC(=O)[C@H](CCCNC(=N)N)NC(=O)[C@H](C)NC(=O)N(C)C)C(N)=O] | <100 | 387.75 |
| 9K | 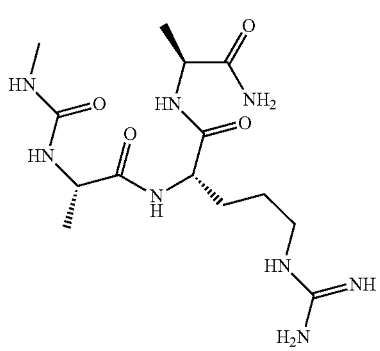 [SMILES: CNC(=O)N[C@@H](C)C(=O)N[C@@H](CCCNC(=N)N)C(=O)N[C@@H](C)C(N)=O] | <10 | 373.33 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
| --- | --- | --- | --- |
| 10A | 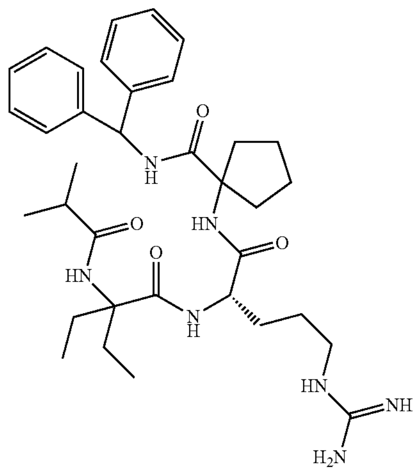 [SMILES: CCC(CC)(NC(=O)C(C)C)C(=O)N[C@@H](CCCNC(=N)N)C(=O)NC1(C(=O)NC(c2ccccc2)c2ccccc2)CCCC1] | <1 | 634.49 |
| 10B | 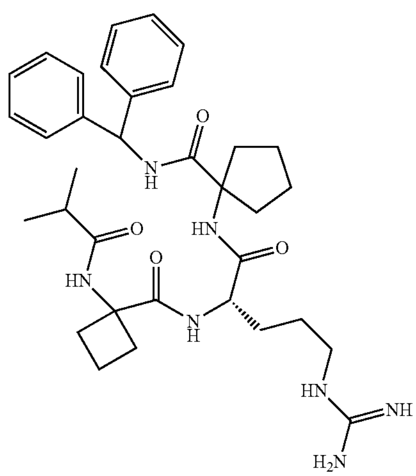 [SMILES: CC(C)C(=O)NC1(C(=O)N[C@@H](CCCNC(=N)N)C(=O)NC2(C(=O)NC(c3ccccc3)c3ccccc3)CCCC2)CCC1] | <1 | 618.47 |
| 10C | 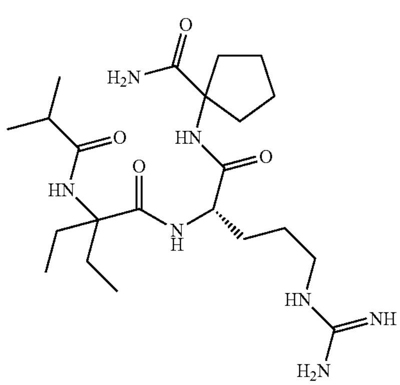 [SMILES: CCC(CC)(NC(=O)C(C)C)C(=O)N[C@@H](CCCNC(=N)N)C(=O)NC1(C(N)=O)CCCC1] | <1 | 468.45 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 10D | 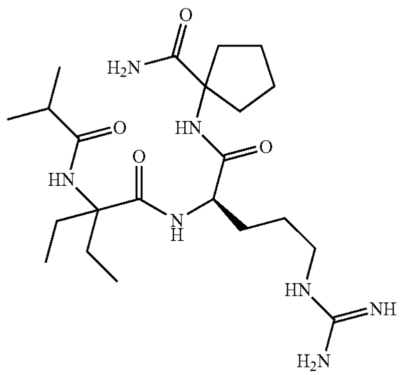 [SMILES: CCC(CC)(NC(=O)C(C)C)C(=O)N[C@H](CCCNC(=N)N)C(=O)NC1(C(N)=O)CCCC1] | <20 | 468.42 |
| 10E | 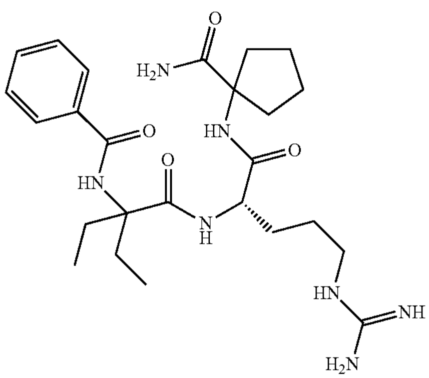 [SMILES: CCC(CC)(NC(=O)c1ccccc1)C(=O)N[C@@H](CCCNC(=N)N)C(=O)NC1(C(N)=O)CCCC1] | >1 | 502.42 |
| 10F | 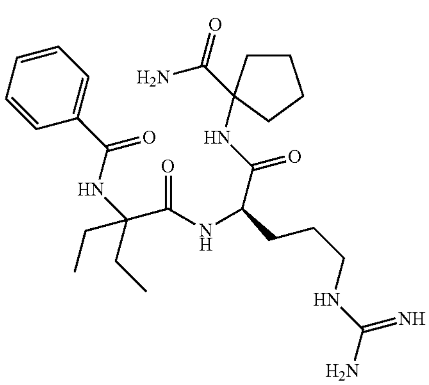 [SMILES: CCC(CC)(NC(=O)c1ccccc1)C(=O)N[C@H](CCCNC(=N)N)C(=O)NC1(C(N)=O)CCCC1] | >5 | 502.50 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 10G | 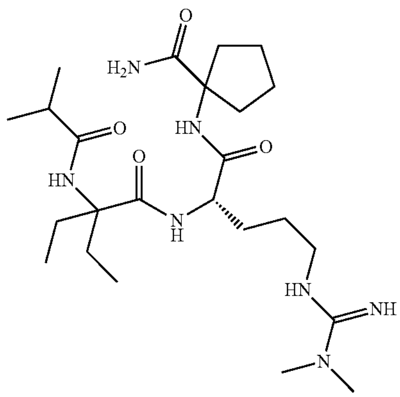 [SMILES: CCC(CC)(NC(=O)C(C)C)C(=O)N[C@@H](CCCNC(=N)N(C)C)C(=O)NC1(C(N)=O)CCCC1] | >1 | 496.50 |
| 10H | 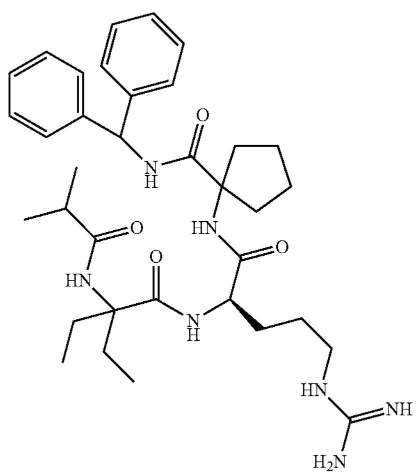 [SMILES: CCC(CC)(NC(=O)C(C)C)C(=O)N[C@H](CCCNC(=N)N)C(=O)NC1(C(=O)NC(c2ccccc2)c2ccccc2)CCCC1] | <1 | 634.50 |
| 10I | 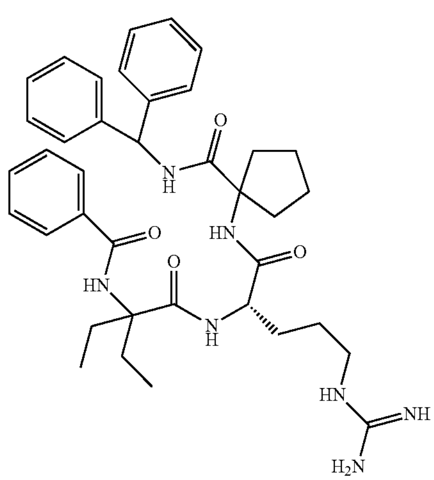 [SMILES: CCC(CC)(NC(=O)c1ccccc1)C(=O)N[C@@H](CCCNC(=N)N)C(=O)NC1(C(=O)NC(c2ccccc2)c2ccccc2)CCCC1] | >5 | 668.50 |

TABLE 5-continued
Structure, binding affinities and ESI-Mass characterization of the compounds.
| Compound | Structure | Binding Affinity to WDR5 (IC$_{50}$ ± SD, μM) | (ESI-MS) (M + H)$^+$ |
|---|---|---|---|
| 10J | 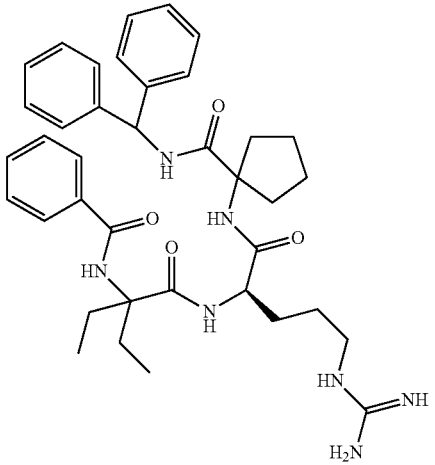 [SMILES: CCC(CC)(NC(=O)c1ccccc1)C(=O)N[C@H](CCCNC(=N)N)C(=O)NC1(C(=O)NC(c2ccccc2)c2ccccc2)CCCC1] | <10 | 668.50 |
| 10K | 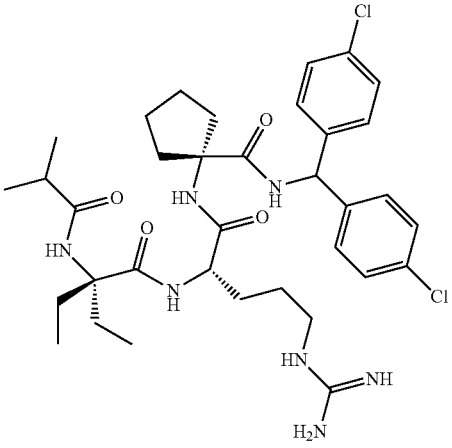 | <3 | 703.33 |
| 10L | 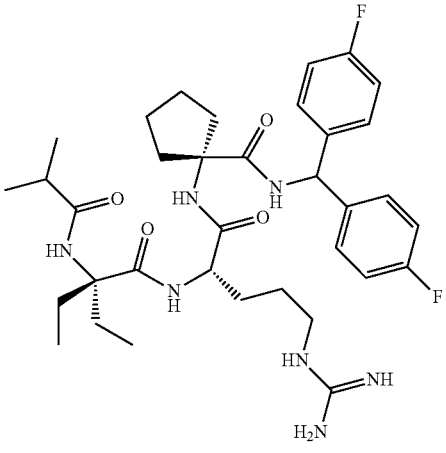 | <3 | 670.33 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 10M | 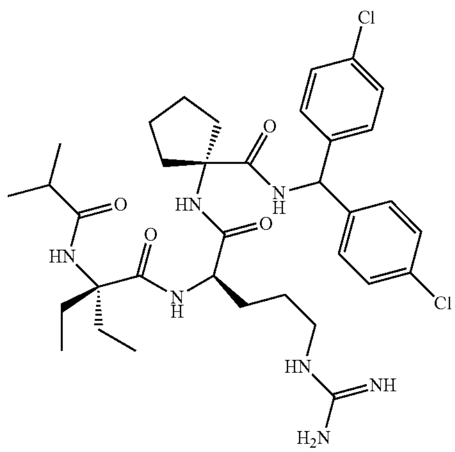 | <10 | 703.33 |
| 10N | 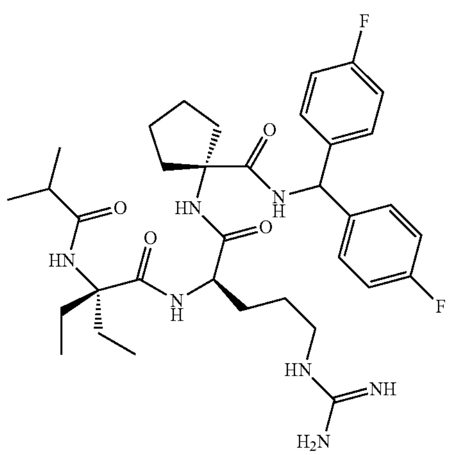 | <10 | 670.58 |
| 11A | 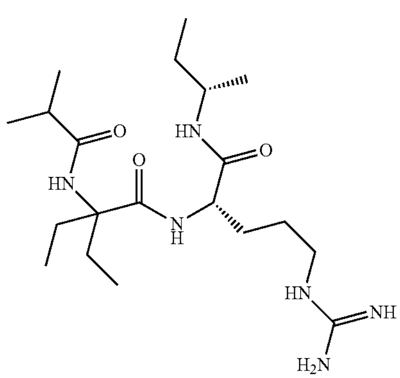 [SMILES: CC[C@H](C)NC(=O)[C@H](CCCNC(=N)N)NC(=O)C(CC)(CC)NC(=O)C(C)C] | <3 | 413.42 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 11B | 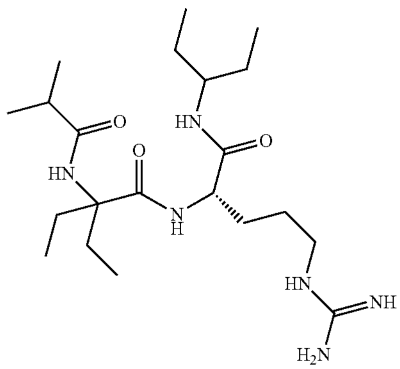 [SMILES: CCC(CC)NC(=O)[C@H](CCCNC(=N)N)NC(=O)C(CC)(CC)NC(=O)C(C)C] | <1 | 427.42 |
| 11C | 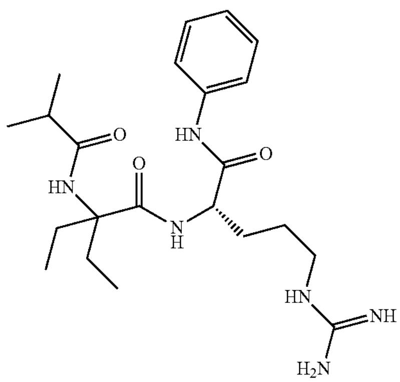 [SMILES: CCC(CC)(NC(=O)C(C)C)C(=O)N[C@@H](CCCNC(=N)N)C(=O)Nc1ccccc1] | <10 | 433.42 |
| 11D | 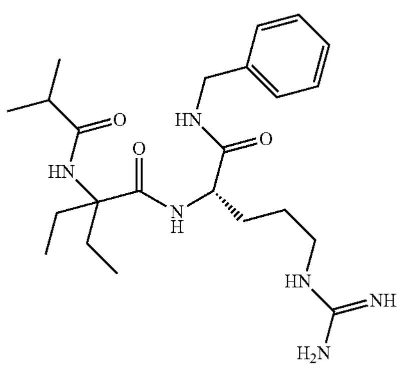 [SMILES: CCC(CC)(NC(=O)C(C)C)C(=O)N[C@@H](CCCNC(=N)N)C(=O)NCc1ccccc1] | <30 | 447.42 |
| 11E | 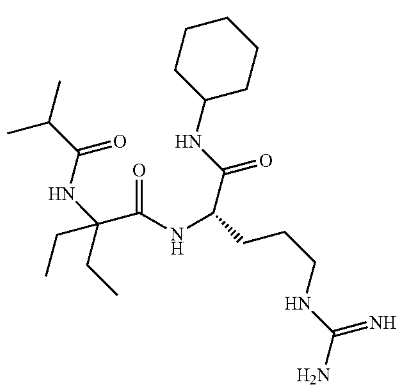 [SMILES: CCC(CC)(NC(=O)C(C)C)C(=O)N[C@@H](CCCNC(=N)N)C(=O)NC1CCCCC1] | <10 | 439.50 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 11F | 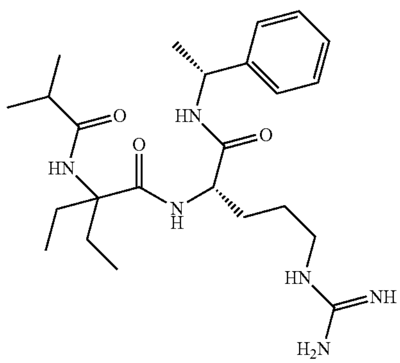 [SMILES: CCC(CC)(NC(=O)C(C)C)C(=O)N[C@@H](CCCNC(=N)N)C(=O)N[C@H](C)c1ccccc1] | <30 | 461.42 |
| 11G | 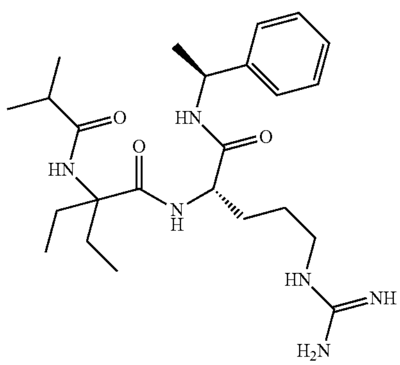 [SMILES: CCC(CC)(NC(=O)C(C)C)C(=O)N[C@@H](CCCNC(=N)N)C(=O)N[C@@H](C)c1ccccc1] | <30 | 461.42 |
| 11H | 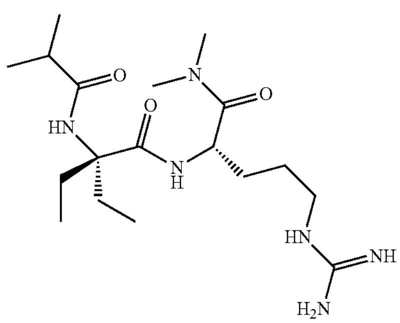 | >30 | 386.00 |
| 11I | 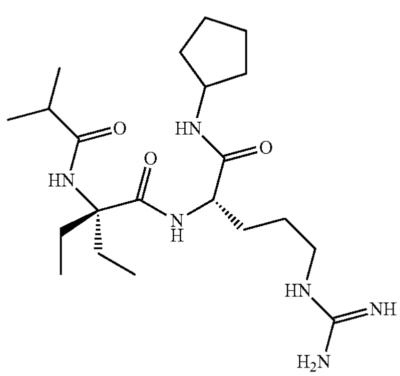 | <10 | 425.67 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 11J | 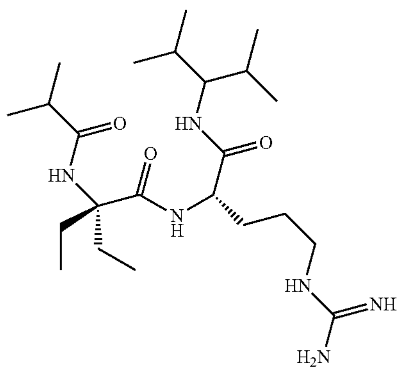 | <10 | 455.58 |
| 11K | 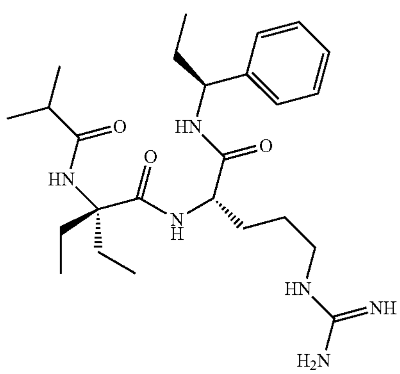 | <3 | 475.75 |
| 11L | 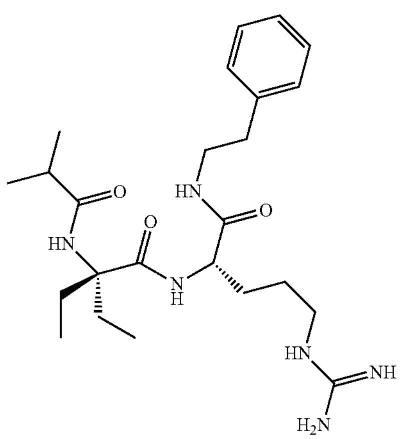 | >10 | 461.67 |

TABLE 5-continued

Structure, binding affinities and ESI-Mass characterization of the compounds.

| Compound | Structure | Binding Affinity to WDR5 (IC$_{50}$ ± SD, μM) | (ESI-MS) (M + H)$^+$ |
|---|---|---|---|
| 11M | 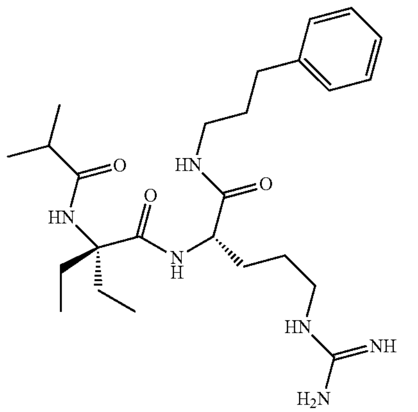 | >1 | 475.67 |
| 11N | 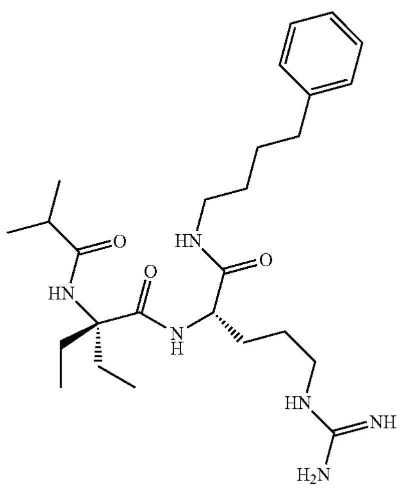 | <10 | 489.75 |
| 12A | 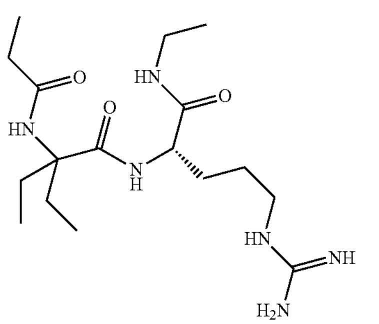 [SMILES: CCNC(=O)[C@H](CCCNC(=N)N)NC(=O)C(CC)(CC)NC(=O)CC] | <10 | 371.92 |

The present invention therefore provides inhibitors of the WDR5 interactions with its binding partners, as exemplified by the compounds disclosed herein, for the treatment of diseases and conditions wherein inhibition of the WDR5 interactions has a beneficial effect. Preferably, a present peptidomimetic compound preferentially binds to WDR5 compared to a WDR5 binding partner by a factor of at least 10, preferably at least 100, and more preferably by a factor of at least 1000.

In one embodiment, the present invention relates to methods of treating an individual suffering from a disease or condition wherein inhibition of WDR5 interactions with its binding partners provides a benefit comprising administering a therapeutically effective amount of a present peptidomimetic compound to an individual in need thereof.

The methods described herein relate to the use of a present peptidomimetic compound useful in the treatment of diseases and conditions wherein inhibition of interactions of WDR5 with its binding partner, including but not limited to the MLL1-WDR5 interaction, provides a benefit, either alone or in conjunction with an optional second therapeutic agent useful in a treatment of the disease or condition of interest. The method of the present invention can be accomplished by administering a present peptidomimetic compound as the neat compound or as a pharmaceutical composition. Administration of a pharmaceutical composition, or neat peptidomimetic compound, can be performed during or after the onset of the disease or condition of interest. Typically, the pharmaceutical compositions are sterile, and contain no toxic, carcinogenic, or mutagenic compounds that would cause an adverse reaction when administered.

In many embodiments, a present peptidomimetic compound is administered in conjunction with a second therapeutic agent useful in the treatment of a disease or condition wherein inhibition of the WDR5 interaction with its binding partners, including but not limited to MLL, provides a benefit. The second therapeutic agent is different from a present peptidomimetic compound. A present peptidomimetic compound and the second therapeutic agent can be administered simultaneously or sequentially. In addition, a present peptidomimetic compound and the second therapeutic agent can be administered from a single composition or two separate compositions. A present peptidomimetic compound and the optional second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention also is directed to pharmaceutical compositions comprising a present peptidomimetic compound and a second therapeutic agent useful in the treatment of diseases and conditions wherein inhibition of the WDR5 interactions with its binding partners provides a benefit. Further provided are kits comprising a present peptidomimetic compound and, optionally, a second therapeutic agent useful in the treatment of diseases and conditions wherein inhibition of the WDR5 interactions with its binding partners provides a benefit, packaged separately or together, and an insert having instructions for using these active agents.

A present peptidomimetic compound and the second therapeutic agent can be administered together as a single-unit dose or separately as multi-unit doses, wherein the present peptidomimetic compound is administered before the second therapeutic agent or vice versa. One or more dose of the present peptidomimetic compound and/or one or more dose of the second therapeutic agent can be administered. The present peptidomimetic compounds therefore can be used in conjunction with one or more second therapeutic agents, for example, but not limited to, anticancer agents.

Within the meaning of the present invention, the term "disease" or "condition" denotes disturbances and/or anomalies that as a rule are regarded as being pathological conditions or functions, and that can manifest themselves in the form of particular signs, symptoms, and/or malfunctions. As demonstrated below, a present peptidomimetic compound is a potent inhibitor of the WDR5 interactions and can be used in treating diseases and conditions wherein inhibition of the WDR5 interactions with its binding partners provides a benefit.

In one embodiment, the present invention provides a method of treating a cancer comprising: (a) administering to an individual in need thereof an amount of a present peptidomimetic compound; and (b) administering to the individual an amount of radiotherapy, chemotherapy, or both. The amounts administered are each effective to treat cancer. In another embodiment, the amounts are together effective to treat the cancer.

In another embodiment, the invention provides a method for treating a cancer, said method comprising administering to a subject in need thereof a pharmaceutical composition comprising an amount of a present peptidomimetic compound effective to treat the cancer.

These therapies can be used in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

The diseases and conditions that can be treated in accordance to the invention include, for example, cancers. A variety of cancers can be treated including, but not limited to: carcinomas, including bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the peptidomimetic compounds of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Accordingly, administration of a present peptidomimetic compound is expected to enhance treatment regimens.

Other cancers that can be treated with the compounds and methods of the invention include, but are not limited to, cancers and metastases selected from the group consisting of solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforma, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; blood-borne cancers, including but not limited to: acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myclomonocytic leukemia, acute nonlymphocytic leukemia, acute undifferentiated leukemia, chronic myclocytic leukemia, chronic lymphocytic leukemia, hairy cell leukemia, and multiple myeloma; acute and chronic leukemias: lymphoblastic, myelogenous lymphocytic, and myelocytic leukemias; lymphomas: Hodgkin's disease and non-Hodgkin's lymphoma; multiple myeloma; Waldenstrom's macroglobulinemia; heavy chain disease; and polycythemia vera.

In the present method, a therapeutically effective amount of peptidomimetic compound of the present invention, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present peptidomimetic compound can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present peptidomimetic compound is administered in an effective amount to achieve its intended purpose. The exact formulation, route of administration, and dosage is determined by an individual physician in view of the diagnosed condition or disease. Dosage amount and interval can be adjusted individually to provide levels of a present peptidomimetic compound that is sufficient to maintain therapeutic effects.

Toxicity and therapeutic efficacy of the present peptidomimetic compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present peptidomimetic compound required for use in therapy varies with the nature of the condition being treated, the length of time that activity is desired, and the age and the condition of the patient, and ultimately is determined by the attendant physician. Dosage amounts and intervals can be adjusted individually to provide plasma levels of a peptidomimetic compound that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present peptidomimetic compound can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a present peptidomimetic compound, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750

µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A present peptidomimetic compound used in a method of the present invention can be administered in an amount of about 0.005 to about 500 milligrams per dose, about 0.05 to about 250 milligrams per dose, or about 0.5 to about 100 milligrams per dose. For example, a present peptidomimetic compound can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

In the treatment of a cancer, a present peptidomimetic compound can be administered with a chemotherapeutic agent and/or radiation, or as an adjunct to surgery.

Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present STAT3 inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a peptidomimetic compound of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct antineoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

TABLE 6

| Alkylating agents | Natural products |
|---|---|
| Nitrogen mustards | Antimitotic drugs |
| mechlorethamine | Taxanes |
| cyclophosphamide | paclitaxel |
| ifosfamide | Vinca alkaloids |
| melphalan | vinblastine (VLB) |
| chlorambucil | vincristine |
| uracil mustard | vinorelbine |
| temozolomide | vindesine |
| Nitrosoureas | Taxotere ® (docetaxel) |
| carmustine (BCNU) | estramustine |
| lomustine (CCNU) | estramustine phosphate |
| semustine (methyl-CCNU) | Epipodophylotoxins |
| chlormethine | etoposide |
| streptozocin | teniposide |
| Ethylenimine/Methyl-melamine | Antibiotics |
| triethylenemelamine (TEM) | actimomycin D |
| triethylene thiophosphoramide (thiotepa) | daunomycin (rubidomycin) |
| | doxorubicin (adriamycin) |
| hexamethylmelamine | mitoxantroneidarubicin |
| (HMM, altretamine) | bleomycin |
| Alkyl sulfonates | splicamycin (mithramycin) |
| busulfan | mitromycin-C |
| pipobroman | dactinomycin |
| Triazines | aphidicolin |
| dacarbazine (DTIC) | epirubicin |
| Antimetabolites | idarubicin |
| Folic Acid analogs | daunorubicin |
| methotrexate | mithramycin |
| trimetrexate | deoxy co-formycin |
| pemetrexed (Multi-targeted antifolate) | Enzymes |
| | L-asparaginase |
| Pyrimidine analogs | L-arginase |
| 5-fluorouracil | Radiosensitizers |
| fluorodeoxyuridine | metronidazole |
| gemcitabine | misonidazole |
| cytosine arabinoside (AraC, cytarabine) | desmethylmisonidazole |
| | pimonidazole |
| 5-azacytidine | etanidazole |
| 2,2'- difluorodeoxy-cytidine | nimorazole |
| floxuridine | RSU 1069 |
| pentostatine | EO9 |
| Purine analogs | RB 6145 |
| 6-mercaptopurine | Nonsteroidal antiandrogens |
| 6-thioguanine | SR4233 |
| azathioprine | flutamide |
| 2'-deoxycoformycin | nicotinamide |

TABLE 6-continued

| | |
|---|---|
| (pentostatin) | 5-bromodeozyuridine |
| erythrohydroxynonyl-adenine (EHNA) | 5-iododeoxyuridine |
| fludarabine phosphate | bromodeoxycytidine |
| 2-chlorodeoxyadenosine | Miscellaneous agents |
| (cladribine, 2-CdA) | Platinium coordination complexes |
| Type I Topoisomerase Inhibitors | cisplatin |
| camptothecin | carboplatin |
| topotecan | oxaliplatin |
| irinotecan | anthracenedione |
| Biological response modifiers | mitoxantrone |
| G-CSF | Substituted urea |
| GM-CSF | hydroxyurea |
| Differentiation Agents | Methylhydrazine derivatives |
| retinoic acid derivatives | N-methylhydrazine (MIH) |
| Hormones and antagonists | procarbazine |
| Adrenocorticosteroids/antagonists | Adrenocortical suppressant |
| prednisone and equivalents | mitotane (o,p' - DDD) |
| dexamethasone | ainoglutethimide |
| ainoglutethimide | Cytokines |
| Progestins | interferon (α, β, γ) |
| hydroxyprogesterone caproate | interleukin-2 |
| medroxyprogesterone acetate | Photosensitizers |
| megestrol acetate | hematoporphyrin derivatives |
| Estrogens | PHOTOFRIN ® |
| diethylstilbestrol | benzoporphyrin derivatives |
| ethynyl estradiol/equivalents | Npe6 |
| Antiestrogen | tin etioporphyrin (SnET2) |
| tamoxifen | pheoboride-a |
| Androgens | bacteriochlorophyll-a |
| testosterone propionate | naphthalocyanines |
| fluoxymesterone/equivalents | phthalocyanines |
| Antiandrogens | zinc phthalocyanines |
| flutamide | Radiation |
| gonadotropin-releasing | X-ray |
| hormone analogs | ultraviolet light |
| leuprolide | gamma radiation |
| | visible light |
| | infrared radiation |
| | microwave radiation |

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274:2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

The peptidomimetic compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of the peptidomimetic compounds.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. The composition typically can be in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present peptidomimetic compound. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present peptidomimetic compound.

When a therapeutically effective amount of a present peptidomimetic compound is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. A present peptidomimetic compound can be infused with other fluids over a 10-30 minute span or over several hours.

The present peptidomimetic compounds can be readily combined with pharmaceutically acceptable carriers well-known in the art. Such carriers enable the active agents to be formulated as tablets, pills, dragees, capsules, liquids, gels, syrups, slurries, suspensions and the like. Pharmaceutical preparations can be obtained by adding a present peptidomimetic compound to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present peptidomimetic compound can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present peptidomimetic compound can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present peptidomimetic compound also can be formulated in rectal compositions, such as suppositories or retention enemas, e.g., containing conventional suppository bases. In addition to the formulations described previously, a compound also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present peptidomimetic compound and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

In accordance with an important feature of the present invention, peptidomimetic compounds were synthesized and evaluated as inhibitors for the WDR5 interactions with its binding partners. For example, compounds of the present invention typically have a bonding affinity ($IC_{50}$) to WDR5 of less than 100 µM, less than 50 µM, less than 10 µM, and less than 1 µM.

PROCEDURES AND EXAMPLES

Fluorescently Tagged Peptides for Assay Development

Quantitative FP based assays are important for accurate evaluation of the binding affinities of the peptidomimetic compounds. Initially, two 5-carboxy fluorescein (5-FAM) tagged tracers (WIN-FAM-1 and WIN-FAM-2) using the WIN sequence with two different linkers were designed and synthesized, as shown in Table 7. These two tracers were found to have similar $K_d$ values and dynamic ranges in the WDR5 saturation experiments (Table 7 and FIG. 1). WIN-FAM-1, WIN-FAM-2, 10mer-Thr-FAM, and 10mer-Alc-FAM were titrated with WDR5 separately.

TABLE 7

Binding affinities of fluorescently tagged tracers to WDR5 protein.
Ac-Amino acid sequence-Linker-K(5-FAM)-NH$_2$

| Tracer Name | Amino acid sequence | Linker | Kd ± SD (µM) |
| --- | --- | --- | --- |
| WIN-FAM-1 | GSARAEVHLRKS | βA-βA-βA* | 0.86 ± 0.15 |
| WIN-FAM-2 | GSARAEVHLRKS | Ahx-Ahx** | 0.94 ± 0.15 |
| 10mer-Ala-FAM | ARAEVHLRKS | Ahx-Ahx | 0.014 ± 0.002 |
| 10mer-Thr-FAM | ARTEVHLRKS | Ahx-Ahx | 0.001 ± 0.0003 |

*βA = Beta alanine
**Ahx = 6-Aminohexanoic acid

To dilutions of WDR5 (Residues 23-334) (2.2-0 µM) in 100 µl assay buffer (0.1M Phosphate, 25 mM KCl, 0.01% Triton, pH 6.5) 20 µl of a fixed concentration of the tracer in the assay buffer was added, followed by an addition of 5 µl DMSO to give 125 µl of total volume. Each assay had two controls, i.e., blank (without protein and tracer) and tracer only (without protein). The plates were incubated on a shaker at room temperature to reach equilibrium and mP values were measured at the 3 hour time point.

Another aspect of the invention is development of a Fluorescent Polarization (FP) based competitive binding assay. 10mer-Thr-FAM was chosen as the tracer for the competitive binding assay. First, the minimal concentration of 10mer-Thr-FAM needed to produce a total fluorescence intensity of 100,000 in the competitive binding assay was evaluated. This was achieved at the concentrations of 0.6 nM or higher, which was selected as the tracer concentration for further evaluations of the assay conditions. Next, the millipolarization (mP) values were measured at different time points in order to determine equilibrium duration and stability. The equilibrium between the tracer and protein was reached at two hours and was stable for over 24 hours (FIG. 2).

Higher protein concentrations can increase the dynamic range (ΔmP) of the assay, but to preserve assay sensitivity, the protein concentration should not exceed the linear range in the saturation curve(31). Accordingly, the optimal protein concentrations for the competitive assay was investigated. WDR5 (2, 3, and 4 nM) with 0.6 nM 10mer-Thr-FAM in competitive binding assays were evaluated and the binding affinities of Ac-10mer under these assay conditions were determined. Although very similar $IC_{50}$ values were obtained with these three protein concentrations, the dynamic range increased from 31 to 40 mP when the protein concentration increased from 2 nM to 4 nM. Therefore, 4 nM was selected as the optimal WDR5 protein concentration and 0.6 nM of 10mer-Thr-FAM tracer in the competitive binding assay for determination of the $IC_{50}$ values of all the peptides shown in Tables 2-4.

Another aspect of the current invention is to develop tools to investigate role of WDR5 interaction with its binding partners including but not limited to MLL and H3 proteins, and the role of WDR5 in cell functions including, but not limited to, H3K4 methylation, expression of Hox genes and skeletal development. These tools can be peptidomimetics of general formula (I) or peptides derived from H3 and MLL sequences as shown in Tables 2-4.

Chemistry

ABBREVIATIONS

OtBu—tertiary butoxide; Trt—trityl; Boc—tert-butoxycarboyl; Mtt—3-(4,5-dimethyl-2-thiazolyl)-2,5-diphenyl- 2H-tetrazolione bromide; Pbf—3-phenyl-benzofuranone; HOBt—1-hydroxybenzotriazole; HBTU—N-[(1H-benzotriazol-1-yl)(dimethylamino)-methylene]-methylmethanaminium hexafluorophosphate N-oxide; DIC—N,N'-diisopropylcarbodiimide; HOAt—7-aza-hydroxybenzotriazole; DMF—dimethylfomiamide; TFA—trifluoroacetic acid; DTT—dithiothreitol; TIS—triisopropylsilane; Fmoc—9-fluorenylmethoxycarbonyl; DIEA—diisopropylethylamine; DCM—dichloromethane; THF—tetrahydrofuran; HATU—2-(1H-7-azabenzotriazol-1-yl)-1,1,3,3-tetramethyl uronium hexafluorophosphate methanaminium; min—minute; h—hour; eq—equivalent; ml—milliliter; MeOH—methanol; IPTG—isopropyl-β-D-1-thiogalactopyranoside; KCl—potassium chloride; HEPES—(4-(2-hydroxyethyl)-1-piperazineethanesulfonic acid); PMSF—phenylmethylsulfonyl fluoride; DMSO—dimethyl sulfoxide.

Solid Phase Peptide Synthesis

Peptides were synthesized manually or with an ABI 433 Peptide synthesizer using Fmoc chemistry. Rink amide resin was used as the solid support. To avoid side reactions, amino acid residues were protected as follows: Glu (OtBu), H is (Trt), Lys (Boc or Mtt), Gln (Trt), Arg (Pbf), Ser (OtBu), Thr (OtBu). HOBt/HBTU or DIC/HOAt was used as the coupling reagent. HCOOH/DIC/HOAt in DMF was used for on-bead formylation where the reaction was carried out in a flask rotated overnight at room temperature using rotavapor without applying vacuum. All the peptides were cleaved from the resin using a TFA:DTT:TIS:H$_2$O (17.5 ml:0.5 g:0.5 ml:1 ml) cleavage cocktail, which also led to removal of the protecting groups. The cleavage solution was evaporated and the crude product was precipitated with diethyl ether followed by HPLC purification using a C18 reversed phase column (Waters, SUNFIRE™ Prep C18, 19×150 mm, 5 μm). All the purified final peptides were analyzed by analytical RP-HPLC (Waters, SUNFIRE™ C18, 4.6×150 mm, 5 μm) for purity and the characterization of the peptides was determined by electrospray ionization mass spectroscopy (ESI-MS) as summarized in Table 8.

TABLE 8

Characterization data of synthesized peptides.

| Peptide | % Purity analytical RP-HPLC* | Calculated | Observed (ESI-MS)** |
|---|---|---|---|
| | | (M + 2H)$^{2+}$ | |
| WIN-FAM-1 | >99 | 1026.009 | 1026.20 |
| WIN-FAM-2 | 99 | 1032.538 | 1032.60 |
| | | (M + H)$^+$ | |
| 10mer-Ala-FAM | 98 | 1920.013 | 1919.87 |
| 10mer-Thr-FAM | 99 | 1950.024 | 1949.87 |
| WIN | 95 | 1351.756 | 1351.73 |
| Ac-11mer | >99 | 1294.734 | 1294.80 |
| Ac-10mer | 90 | 1207.702 | 1207.73 |
| NH$_2$-11mer | >99 | 1252.724 | 1252.80 |
| Ac-9mer | 98 | 1136.665 | 1136.73 |
| Ac-7mer | 96 | 836.474 | 836.53 |
| Ac-6mer | 97 | 723.390 | 723.53 |
| Ac-5mer | 99 | 586.331 | 586.47 |
| Ac-4mer | 93 | 487.263 | 487.40 |
| Ac-3mer | 96 | 358.220 | 358.33 |
| Ac-2mer | >99 | 287.183 | 287.27 |
| NH$_2$-10mer | 98 | 1165.692 | 1165.73 |
| NH$_2$-3mer | >99 | 316.210 | 316.27 |
| CHO-ARA | >99 | 344.205 | 344.27 |
| Δ1 | >99 | 372.236 | 372.33 |
| Δ2a | 95 | 372.236 | 372.33 |
| Δ2b | >99 | 386.252 | 386.33 |
| Δ2c | 95 | 373.220 | 373.33 |
| H3-10mer | >99 | 1145.687 | 1145.80 |

TABLE 8-continued

Characterization data of synthesized peptides.

| Peptide | % Purity analytical RP-HPLC* | Calculated | Observed (ESI-MS)** |
|---|---|---|---|
| | | (M + 2H)$^{2+}$ | |
| Ac-H3-10mer | >99 | 1187.697 | 1187.73 |
| H3-3mer | 93 | 346.220 | 346.27 |
| Ac-H3-3mer | 95 | 388.231 | 388.33 |
| H3-10mer-K4Me | >99 | 1159.702 | 1159.80 |
| H3-10mer-K4Me$_2$ | >99 | 1173.718 | 1173.80 |
| H3-10mer-K4Me$_3$ | >99 | 1188.741 | 1187.80 |

*Waters, SUNFIRE ™ C18, 4.6 × 150 mm, 5 μm.
**Finnigan LCQ Deca (Thermoquest).

Synthesis of C-Terminally Modified Peptides.

The corresponding peptide intermediates with C-terminal —COOH group were synthesized using Fmoc-solid phase chemistry and 2-chlorotrityl chloride resin as the solid support. The first residue (3 eq.) was loaded in DCM and in the presence of 3 eq. DIEA for 3 hours overnight. Next, classical chain elongation was carried out with Fmoc Chemistry. The carboxylic acid intermediate was cleaved from the resin by treatment with 4 ml of 1% TFA in DCM (3×10 minutes). The filtrate was evaporated and purified over the HPLC using the C18 reverse phase column. The —COOH intermediate (0.2 mmol) dissolved in 10 ml of THF was mixed with 3 eq. HATU, 3 eq. HOAt, 5 eq. DIEA, and 3 eq. of the corresponding amine. The reaction mixture was stirred at room temperature for 24 hours, the solvent was evaporated and the crude product purified by HPLC. The Pbf protected group from the arginine was removed by treatment with the cleavage cocktail, followed by HPLC purification.

Synthesis of Δ2c

The Ac-AR(Pbf)A-COOH intermediate (0.2 mol) was dissolved in absolute MeOH, and 0.5 mL of TFA was added. The reaction mixture was stirred at room temperature for three days, the solvent evaporated and the Pbf protecting group was removed by treatment with the cleavage cocktail to give a final product which was purified by HPLC.

Synthesis of Tracers

The peptide was synthesized as described above with an Mtt protecting group on the C-terminal lysine residue. The fluorescein label, 5-FAM, was introduced to the side chain of C-terminal lysine by removal of the Mtt protecting group with 5 ml 1% TFA in DCM (4×10 minutes) followed by overnight treatment with 1.5 eq. 5-carboxy fluorescein succinimide ester (5-FAM, SE) and 4 eq. DIEA. The peptide was cleaved from the resin and purified over HPLC as described above.

Binding Assay

Protein Expression and Purification for the Binding Assay

N-terminal His-tagged WDR5Δ23 (residues 24-334) was expressed from the pET28-MHL vector in Rosetta2(DE3) pLysS cells (Novagen). Cells were grown to OD$_{600}$=0.4-0.6 in 4 L 2XTY at 30° C., induced with 0.1 mM IPTG at 16° C. for 16 hours and harvested in 20 mM HEPES pH 7.5, 500 mM KCl, 10% glycerol, 0.1 mg/ml PMSF, 0.05% NP40. Cells were lysed by addition of 0.2 mg/ml hen egg white lysozyme followed by sonication and clarification by centrifuging for 30 minutes at 15,000 rpm. The resin was washed 3 times for 10 minutes with 40 ml lysis buffer. His-WDR5Δ23 was eluted from the resin by 3×15 minute elutions with 20 mM HEPES pH 7.5, 100 mM KCl, 10% glycerol, 250 mM imidazole pH 7.5. Eluates were clarified by centrifugation at 2000 rpm for 1 minute, syringe-filtered through a 0.45 μM membrane (Millipore), then loaded onto two 5 ml SP-Sepharose Hi-Trap columns using the AKTApurifier (GE Healthcare). Fractions were eluted in 20 mM HEPES pH 7.5, 10% glycerol with a KCl gradient from 0-1000 mM and peak fractions were pooled and concentrated to 64 µM using an Amicon Ultra centrifugal filter, 10,000 MWCO (Amicon). Concentrated protein was aliquoted and samples were frozen on dry ice and stored at −80° C.

FP Based Experiments

All the FP based experiments were performed in MICROFLUOR® 2 Black, "U" Bottom, 96-well Microtiter Plates (ThermoSci.) and FP was measured as mP units in a microplate reader (Tecan Ultra) with excitation at 485 nm and emission at 530 nm. The $K_d$ of the tracers and the $IC_{50}$ value of the inhibitors were calculated using GraphPad Prism 4 software.

Saturation Binding Experiment to Determine Dissociation Constant ($K_d$) of the Tracers To dilutions of WDR5Δ23 (2.2-0 µM) in 100 µl assay buffer (0.1M Phosphate, 25 mM KCl, 0.01% Triton, pH 6.5) 20 µl of a fixed concentration of the tracer in the assay buffer was added, followed by an addition of 5 µl DMSO to give 125 µl of total volume. Each assay had two controls: blank (without protein and tracer) and tracer only (without protein). The plates were incubated on a shaker at room temperature to reach equilibrium and mP values were measured at the 3 hour time point.

Competitive Binding Experiments

The binding affinities of the synthetic peptides shown in the study were measured using this competitive binding assay. A pre-incubated complex solution of WDR5Δ23 and the tracer in 120 µl assay buffer were added to dilutions of the test compound in 5 µl DMSO, giving final concentrations of WDR5Δ23 and the tracer of 4 nM and 0.6 nM, respectively. Three control wells were included in each plate: blank (without protein and tracer), 100% inhibition (tracer only), and 0% inhibition (complex solution only). The plates were incubated with shaking at room temperature. The mP values were measured after five hours of incubation and $K_i$ values were calculated using the equation described previously(31).

Inhibition of Histone Methyltransferase Activity of the MLL1 Core Complex

The interaction of WDR5 and MLL1 is critical for H3K4 methyltransferase activity of the MLL1 core complex. Inhibitors that block this interaction are expected to inhibit the catalytic activity of the core complex.

An in vitro functional assay using recombinant MLL1, WDR5, RbBP5 and Ash2L proteins, an H3-10mer (residues 1-10) peptide as the substrate, and a radio-labeled cofactor $^3$H—S-adenosyl methionine was developed. Assays were performed in 50 mM HEPES pH 7.8, 100 mM NaCl, 1.0 mM EDTA and 5% glycerol at room temperature. Each reaction contained 1.5 µCi of the cofactor, $^3$H—S-adenosyl methionine (Perkin Elmer). A Histone 3 peptide (residues 1-10) was used as the substrate at 50 µM. Inhibitors were added at concentrations ranging from 0.125-128 µM. Reactions were initiated by addition of the MLL complex, composed of bacterially expressed fragments $MLL^{3762-C'}$, $WDR5^{23-C'}$, RbBP5 and $Ash2L^{SPRY}$, at a final concentration of 0.5 µM and allowed to proceed for 30 minutes before counting. As a negative control, assays were performed using 0.5 µM MLL complex assembled with the non-interacting mutant, $WDR5^{D107A}$. The MLL1 histone methyltransferase activity was monitored by the incorporation of the radioactivity into the lysine residue in the Histone 3 peptide substrate determined with a scintillation counter. Using this assay, the inhibitory activity for a number of compounds with different ranges of binding affinities to WDR5 in an FP-based assay were evaluated. The results are shown in FIG. 3.

One peptide (ARAbu), which binds strongly to WDR5 in the binding assay, effectively inhibits the MLL1 histone methyltransferase activity with an $IC_{50}$ value of 1.8 µM. Another peptide, VRA, which binds to WDR5 with a weaker affinity than ARAbu, inhibits the MLL1 histone methyltransferase activity with an $IC_{50}$ value of 12 µM. A third peptide, GRA, which binds to WDR5 with a very weak affinity, fails to inhibit the MLL1 histone methyltransferase activity at concentrations up to 100 µM. These functional data show that small compounds designed to bind to the MLL binding site in WDR5 inhibit the MLL1 histone methyltransferase activity of the core complex.

REFERENCES

1. Kouzarides, T. Chromatin modifications and their function. *Cell* 2007, 128, 693-705.
2. Jenuwein, T.; Allis, C. D. Translating the histone code. *Science* 2001, 293, 1074-1080.
3. Shilatifard, A. Molecular implementation and physiological roles for histone H3 lysine 4 (H3K4) methylation. *Curr Opin Cell Biol* 2008, 20, 341-348.
4. Sims, R. J., 3rd; Reinberg, D. Histone H3 Lys 4 methylation: caught in a bind? *Genes Dev* 2006, 20, 2779-2786.
5. Wysocka, J.; Swigut, T.; Xiao, H.; Milne, T. A.; Kwon, S. Y.; Landry, J.; Kauer, M.; Tackett, A. J.; Chait, B. T.; Badenhorst, P.; Wu, C.; Allis, C. D. A PHD finger of NURF couples histone H3 lysine 4 trimethylation with chromatin remodelling. *Nature* 2006, 442, 86-90.
6. Huntsman, D. G.; Chin, S. F.; Muleris, M.; Batley, S. J.; Collins, V. P.; Wiedemann, L. M.; Aparicio, S.; Caldas, C. MLL2, the second human homolog of the *Drosophila trithorax* gene, maps to 19q13.1 and is amplified in solid tumor cell lines. *Oncogene* 1999, 18, 7975-7984.
7. Ruault, M.; Brun, M. E.; Ventura, M.; Roizes, G.; De Sario, A. MLL3, a new human member of the TRX/MLL gene family, maps to 7q36, a chromosome region frequently deleted in myeloid leukaemia. *Gene* 2002, 284, 73-81.
8. Hess, J. L. MLL: a histone methyltransferase disrupted in leukemia. *Trends Mol Med* 2004, 10, 500-507.
9. Guenther, M. G.; Jenner, R. G.; Chevalier, B.; Nakamura, T.; Croce, C. M.; Canaani, E.; Young, R. A. Global and Hox-specific roles for the MLL1 methyltransferase. *Proc Natl Acad Sci USA* 2005, 102, 8603-8608.
10. Mishra, B. P.; Ansari, K. I.; Mandal, S. S. Dynamic association of MLL1, H3K4 trimethylation with chromatin and Hox gene expression during the cell cycle. *FEBS J* 2009, 276, 1629-1640.
11. Hombria, J. C.; Lovegrove, B. Beyond homeosis—HOX function in morphogenesis and organogenesis. *Differentiation* 2003, 71, 461-476.
12. Monier, B.; Tevy, M. F.; Perrin, L.; Capovilla, M.; Semeriva, M. Downstream of homeotic genes: in the heart of Hox function. *Fly (Austin)* 2007, 1, 59-67.
13. Jude, C. D.; Climer, L.; Xu, D.; Artinger, E.; Fisher, J. K.; Ernst, P. Unique and independent roles for MLL in adult hematopoietic stem cells and progenitors. *Cell Stem Cell* 2007, 1, 324-337.
14. Ferrando, A. A.; Armstrong, S. A.; Neuberg, D. S.; Sallan, S. E.; Silverman, L. B.; Korsmeyer, S. J.; Look, A. T. Gene expression signatures in MLL-rearranged T-lineage and B-precursor acute leukemias: dominance of HOX dysregulation. *Blood* 2003, 102, 262-268.

15. Harper, D. P.; Aplan, P. D. Chromosomal rearrangements leading to MLL gene fusions: clinical and biological aspects. *Cancer Res* 2008, 68, 10024-10027.
16. Argiropoulos, B.; Humphries, R. K. Hox genes in hematopoiesis and leukemogenesis. *Oncogene* 2007, 26, 6766-6776.
17. Maulbecker, C. C.; Gruss, P. The oncogenic potential of deregulated homeobox genes. *Cell Growth Differ* 1993, 4, 431-441.
18. Waltregny, D.; Alami, Y.; Clausse, N.; de Leval, J.; Castronovo, V. Overexpression of the homeobox gene HOXC8 in human prostate cancer correlates with loss of tumor differentiation. *Prostate* 2002, 50, 162-169.
19. De Vita, G.; Barba, P.; Odartchenko, N.; Givel, J. C.; Freschi, G.; Bucciarelli, G.; Magli, M. C.; Boncinelli, E.; Cillo, C. Expression of homeobox-containing genes in primary and metastatic colorectal cancer. *Eur J Cancer* 1993, 29A, 887-893.
20. Hsieh, J. J.; Ernst, P.; Erdjument-Bromage, H.; Tempst, P.; Korsmeyer, S. J. Proteolytic cleavage of MLL generates a complex of N- and C-terminal fragments that confers protein stability and subnuclear localization. *Mol Cell Biol* 2003, 23, 186-194.
21. Patel, A.; Vought, V. E.; Dharmarajan, V.; Cosgrove, M. S. A conserved arginine-containing motif crucial for the assembly and enzymatic activity of the mixed lineage leukemia protein-1 core complex. *J Biol Chem* 2008, 283, 32162-32175.
22. Dou, Y.; Milne, T. A.; Ruthenburg, A. J.; Lee, S.; Lee, J. W.; Verdine, G. L.; Allis, C. D.; Roeder, R. G. Regulation of MLL1 H3K4 methyltransferase activity by its core components. *Nat Struct Mol Biol* 2006, 13, 713-719.
23. Wysocka, J.; Swigut, T.; Milne, T. A.; Dou, Y.; Zhang, X.; Burlingame, A. L.; Roeder, R. G.; Brivanlou, A. H.; Allis, C. D. WDR5 associates with histone H3 methylated at K4 and is essential for H3 K4 methylation and vertebrate development. *Cell* 2005, 121, 859-872.
24. Song, J. J.; Kingston, R. E. WDR5 interacts with mixed lineage leukemia (MLL) protein via the histone H3-binding pocket. *J Biol Chem* 2008, 283, 35258-35264.
25. Patel, A.; Dharmarajan, V.; Cosgrove, M. S. Structure of WDR5 bound to mixed lineage leukemia protein-1 peptide. *J Biol Chem* 2008, 283, 32158-32161.
26. Schuetz, A.; Allali-Hassani, A.; Martin, F.; Loppnau, P.; Vedadi, M.; Bochkarev, A.; Plotnikov, A. N.; Arrowsmith, C. H.; Min, J. Structural basis for molecular recognition and presentation of histone H3 by WDR5. *EMBO J* 2006, 25, 4245-4252.
27. Han, Z.; Guo, L.; Wang, H.; Shen, Y.; Deng, X. W.; Chai, J. Structural basis for the specific recognition of methylated histone H3 lysine 4 by the WD-40 protein WDR5. *Mol Cell* 2006, 22, 137-144.
28. Couture, J. F.; Collazo, E.; Trievel, R. C. Molecular recognition of histone H3 by the WD40 protein WDR5. *Nat Struct Mol Biol* 2006, 13, 698-703.
29. Ruthenburg, A. J.; Wang, W.; Graybosch, D. M.; Li, H.; Allis, C. D.; Patel, D. J.; Verdine, G. L. Histone H3 recognition and presentation by the WDR5 module of the MLL1 complex. *Nat Struct Mol Biol* 2006, 13, 704-712.
30. Trievel, R. C.; Shilatifard, A. WDR5, a complexed protein. *Nat Struct Mol Biol* 2009, 16, 678-680.
31. Nikolovska-Coleska, Z.; Wang, R.; Fang, X.; Pan, H.; Tomita, Y.; Li, P.; Roller, P. P.; Krajewski, K.; Saito, N. G.; Stuckey, J. A.; Wang, S. Development and optimization of a binding assay for the XIAP BIR3 domain using fluorescence polarization. *Anal Biochem* 2004, 332, 261-273.
32. Faber, J.; Krivtsov, A. V.; Stubbs, M. C.; Wright, R.; Davis, T. N.; van den Heuvel-Eibrink, M.; Zwaan, C. M.; Kung, A. L.; Armstrong, S. A. HOXA9 is required for survival in human MLL-rearranged acute leukemias. *Blood* 2009, 113, 2375-2385.
33. Patel, A.; Dharmarajan, V.; Vought, V. E.; Cosgrove, M. S. On the mechanism of multiple lysine methylation by the human mixed lineage leukemia protein-1 (MLL1) core complex. *J Biol Chem* 2009, 284, 24242-24256.
34. D. A. Case, T. A. D., T. E. Cheatham, III, C. L. Simmerling, J.; Wang, R. E. D., R. Luo, K. M. Merz, D. A. Pearlman, M. Crowley, R. C.; Walker, W. Z., B. Wang, S. Hayik, A. Roitberg, G. Seabra, K. F.; Wong, F. P., X. Wu, S. Brozell, V. Tsui, H. Gohlke, L. Yang, C.; Tan, J. M., V. Hornak, G. Cui, P. Beroza, D. H. Mathews, C.; Schafmeister, W. S. R., P. A. Kollman. AMBER 9. In University of California: San Francisco, 2006.

What is claimed:
1. A composition comprising (a) a peptidomimetic compound having a structure

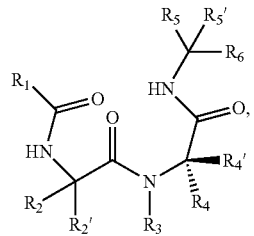

wherein $R_1$ is selected from the group consisting of $CH_3$—, —$CH(CH_3)_2$, —$CH_2CH_3$, —$CH_2CH_2CH_3$, —$(CH_2)_3CH_3$, cyclopropyl, cyclobutyl, cyclopentyl, phenyl, benzyl, or —$NH(CH_3)$;

$R_2$, and $R_2'$, independently, are selected from the group consisting of —H; $C_{1-9}$ substituted or unsubstituted straight chain or branched alkyl, $C_{3-7}$ cycloalkyl; —$(CH_2)_n$—U, wherein U is substituted or unsubstituted phenyl or heteroaryl and n=0-6; —C(A)(B)(D) wherein A is selected from the group consisting of —H, —OH, —$OCH_3$, —$NH_2$, —$NHCH_3$, —$N(CH_3)_2$, —SH, —$SCH_3$, and B and D, independently, are selected from the group consisting of H, substituted or unsubstituted $C_{1-6}$ straight chain or branched alkyl, $C_{3-7}$ cycloalkyl, and —$(CH_2)_n$—U, wherein U is substituted or unsubstituted phenyl or heteroaryl and n=0-6; or $R_2$ and $R_2'$ together with the carbon atom to which they are attached can form a $C_{3-7}$ carbocyclic ring;

$R_5$ and $R_5'$, independently, are selected from the group consisting of —H; —$CH_2CH_2CO_2H$; $C_{1-9}$ substituted or unsubstituted straight chain or branched alkyl, $C_{3-7}$ cycloalkyl; —$(CH_2)_n$—U, wherein U is substituted or unsubstituted phenyl and n=0-6; —C(A)(B)(D) wherein A is selected from the group consisting of —H, —OH, —$OCH_3$, —$NH_2$, —$NHCH_3$, —$N(CH_3)_2$, —SH, —$SCH_3$, and B and D, independently, are selected from the group consisting of H, substituted or unsubstituted $C_{1-6}$ straight chain or branched alkyl, and $C_{3-7}$ cycloalkyl, —$(CH_2)_n$—U, wherein U is substituted or unsubstituted phenyl and n=0-6; or $R_5$ and $R_5'$ together with the carbon atom to which they are attached can form a $C_{3-7}$ carbocyclic ring or $R_5$ and $R_5'$ are null;

R₃ is H or substituted or unsubstituted $C_{1-6}$ straight chain or branched alkyl, or $C_{3-7}$ cycloalkyl;

R₄ is —H, $C_{1-6}$alkyl, —$(CH_2)_n$-E, arylE,

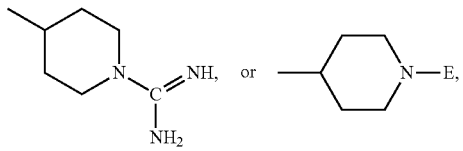

wherein n=2-6 and E is selected from the group consisting of —$NH_2$, —$NHCH_3$, —$N(CH_3)_2$, —$N+(CH_3)_3$, —FL-C(=NJ)NKK', —FL-C(=O)NKK', and —FL-C(=S)NKK', wherein F is $C_{1-6}$alkyl, aryl, N, or CH, and L, J, K, K', independently, are H or —$CH_3$;

R₄' is —H, a $C_{1-6}$ straight chain or branched alkyl, or $C_{3-7}$cycloalkyl, each unsubstituted or substituted with one or more halogen or OH;

R₆ is selected from the group consisting of $C_{3-7}$ cycloalkyl; —C(=O)N(M)Q, wherein M is H and Q is selected from the group consisting of —H, $C_{1-12}$ straight chain or branched alkyl, $C_{3-7}$ cycloalkyl, phenyl, or benzyl, wherein each optionally is substituted with one or more of —OH, —$OCH_3$, —$NH_2$, —$NHCH_3$, —$N(CH_3)_2$ or halogen, and, CHP'P", wherein P' and P", independently, are selected from the group consisting of unsubstituted or substituted phenyl or benzyl, or M and Q together with the nitrogen atom to which they are attached can form a 3 to 8 membered ring;

wherein a phenyl group is optionally substituted with one or more halo, alkyl, alkenyl, —$OCF_3$, —$NO_2$, —CN, —NC, —OH, alkoxy, amino, alkylamino, —$CO_2H$, —$CO_2$alkyl, aryl, heteroaryl, and a $C_{1-9}$ straight chain or branched chain alkyl group is optionally substituted with halo, trifluoromethyl, trifluoromethoxy, hydroxy, alkoxy, nitro, cyano, alkylamino, or amino;

or a pharmaceutically acceptable salt thereof, (b) an optional second therapeutic agent useful in a treatment of a cancer; and (c) an excipient and/or pharmaceutically acceptable carrier.

2. The composition of claim 1 wherein R₁ is H, optionally substituted $C_{1-4}$alkyl, $C_{3-5}$cycloalkyl, —NH($C_{1-3}$alkyl), phenyl, or —$CH_2$phenyl.

3. The composition of claim 1 wherein R₂ and R₂', independently, are H, $C_{1-4}$alkyl, —$(CH_2)_{1-2}$SH, $C_{3-6}$cycloalkyl, —$CH_2$-heteroaryl, —$CH_2$phenyl, or —$C_{1-4}$alkyleneOH, or R₂ and R₂' are taken together with the carbon to which they are attached to form a $C_4$ to $C_6$ spiro structure.

4. The composition of claim 1 wherein R₂ and R₂', independently, are H, —$CH_3$, —$CH_2CH_3$, —$CH(CH_3)_3$, —$(CH_2)_2$ $CH_3$, —$C(CH_3)_2$, —$CH_2SH$, —$CH_2CH(CH_3)_2$, cyclopentyl, cyclohexyl,

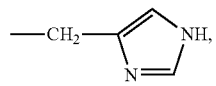

—$CH_2$phenyl, —$CH_2OH$, —$CH(OH)CH_3$, or R₂ and R₂' are taken together with the carbon to which they are attached to form a spiro $C_3$, $C_4$, $C_5$, or $C_6$ moiety.

5. The composition of claim 1 wherein R₃ is H.

6. The composition of claim 1 wherein R₄ is H, —$(CH_2)_n$—FH—C(=NJ)NKK', aryl-FH—C(=NJ)NKK',

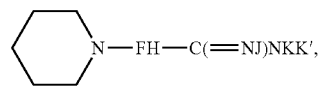

$C_{1-4}$alkyl, or —$(CH_2)_nNH_2$.

7. The composition of claim 1 wherein R₄ is H,

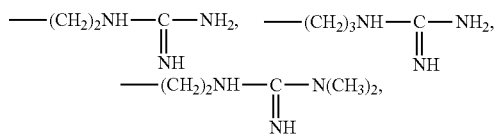

—$(CH_2)_3CH_3$, —$(CH_2)_{3-4}NH_2$,

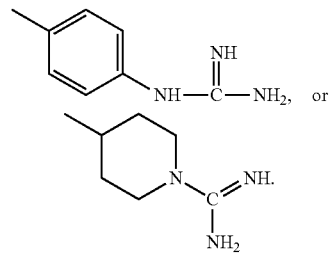

8. The composition of claim 1 wherein R₄' is H.

9. The composition of claim 1 wherein R₅ and R₅', independently, are null, H, optionally substituted $C_{1-4}$alkyl, —$CH_2SH$, $CH_2OH$, $C_{3-6}$cycloalkyl, —$CH_2$phenyl, —CH(OH)$CH_3$, —$(CH_2)_2CO_2H$, phenyl optionally halo substituted, or R₅ and R₅' are taken together with the carbon to which they are attached to form a $C_3$ to $C_6$ spiro moiety.

10. The composition of claim 1 wherein R₅ and R₅', independently, are null, H, —$CH_3$, —$CH_2CH_3$, —$CH(CH_3)_2$, —$CH_2SH$, —$CH_2OH$, —$CH_2CH(CH_3)_2$,

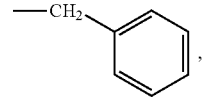

—$CH(OH)CH_3$, —$C(CH_2)_3$, cyclohexyl, —$(CH_2)_2CO_2H$, cyclopentyl, or R₅ and R₅' are taken together with the carbon to which they are attached to form a $C_3$, $C_4$, $C_5$, or $C_6$ spiro moiety.

11. The composition of claim 1 wherein R₆ is —C(=O)N(M)(Q) and Q, is H, optionally substituted $C_{1-8}$alkyl, phenyl, —$(CH_2)_{1-4}$phenyl, —CH(phenyl)₂ optionally halo substituted, —CH($CH_3$)phenyl, or $C_{3-6}$cycloalkyl.

12. The composition of claim 1 wherein R₆ is —C(=O)N(M)(Q) and Q is H, —$CH_3$, —$CH_2CH_3$, —$CH(CH_3)_2$, —CH($CH_2CH_3$)₂, cyclohexyl, cyclopentyl, phenyl,

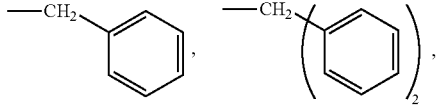

-continued
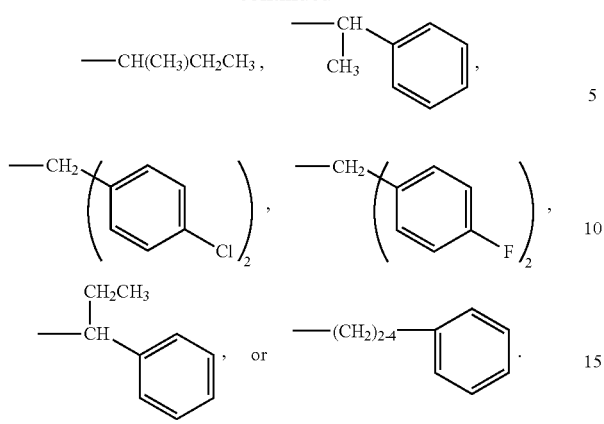
13. The composition of claim 1 wherein the peptidomimetic compound is selected from the group consisting of
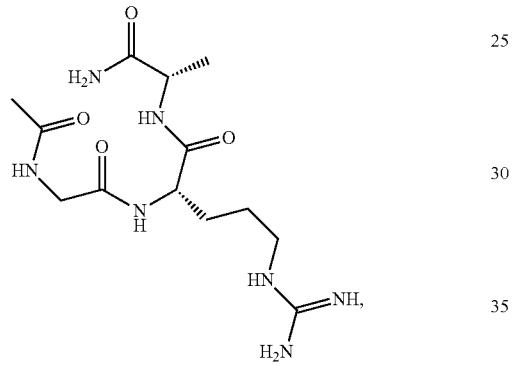
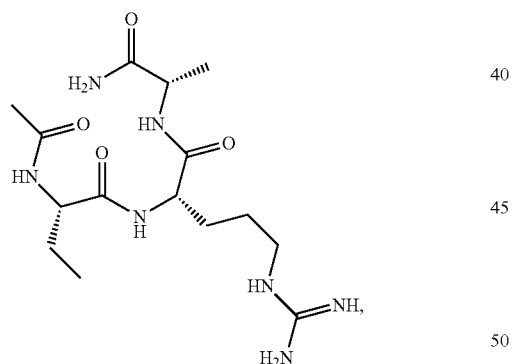
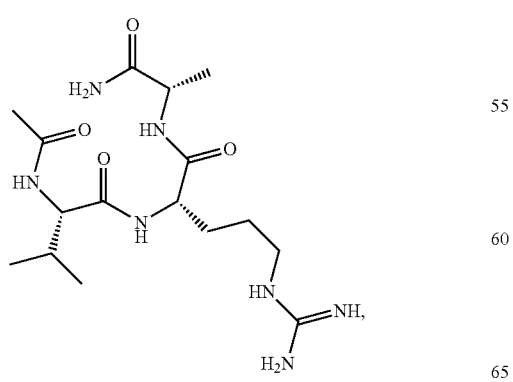
-continued
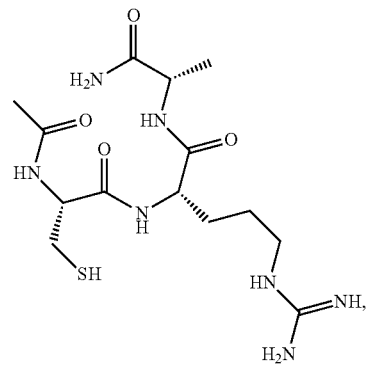
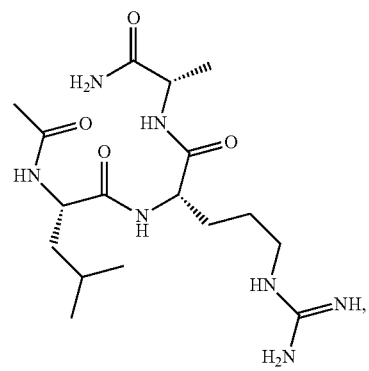
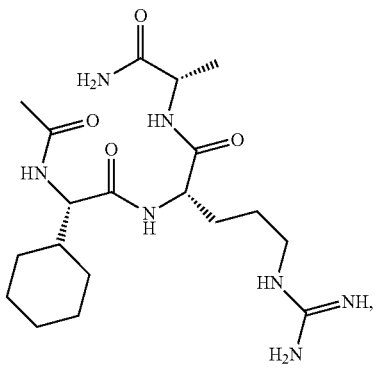
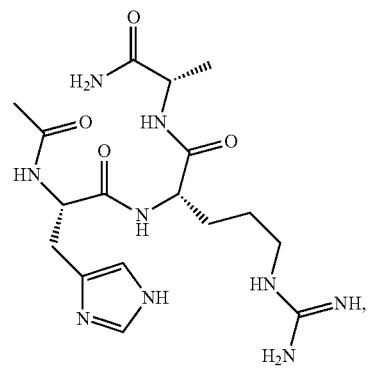

99
-continued
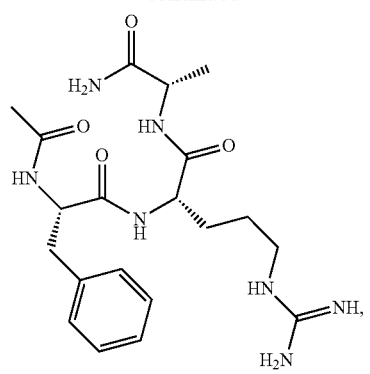
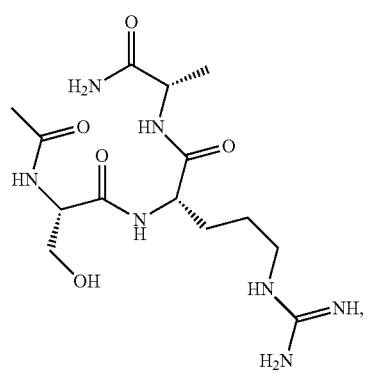
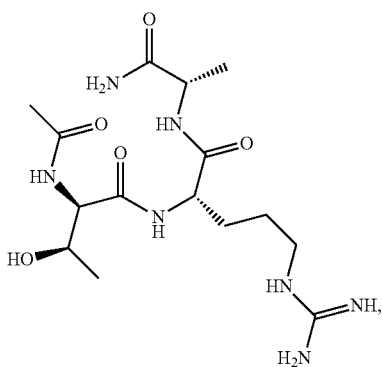
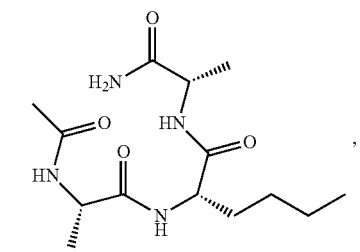
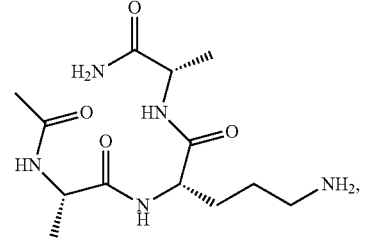
100
-continued
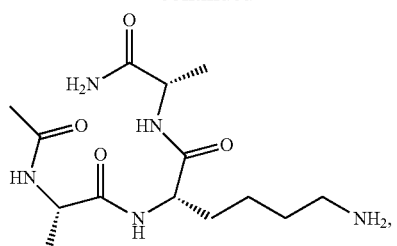
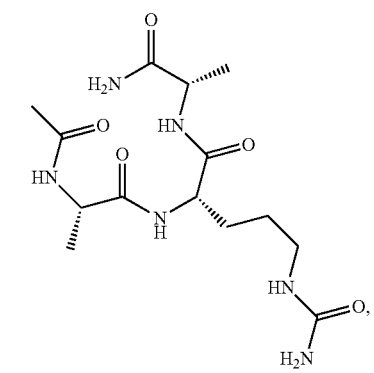
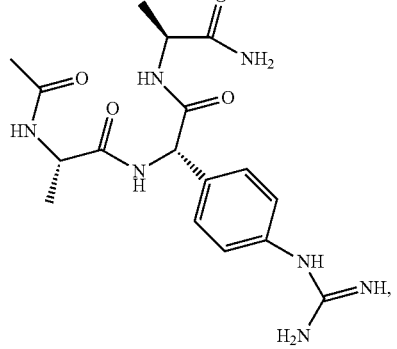
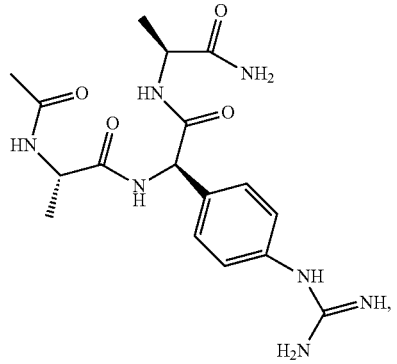
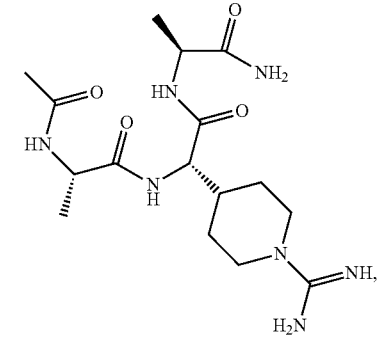

101
-continued
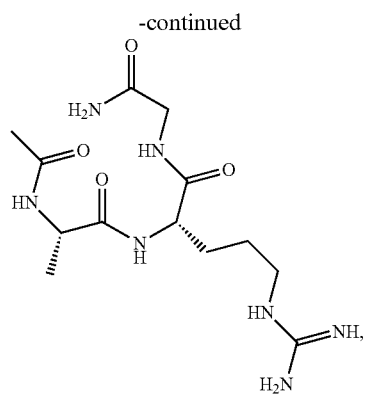
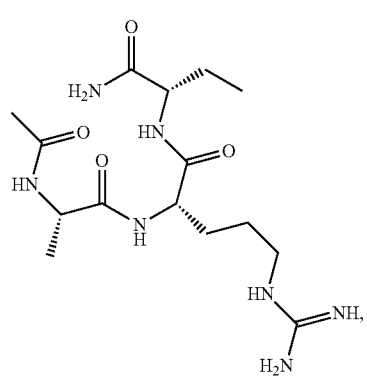
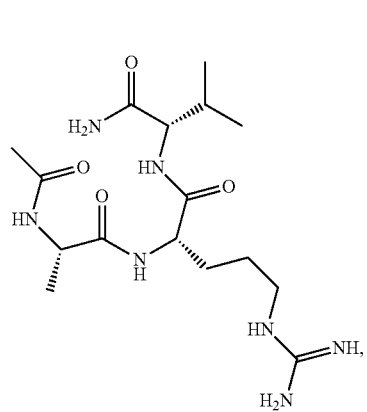
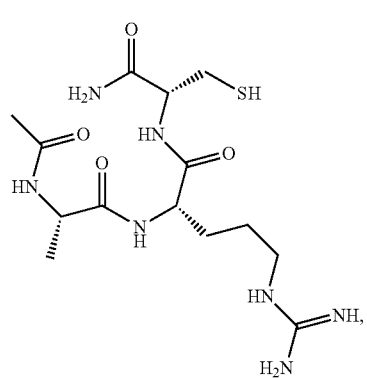
102
-continued
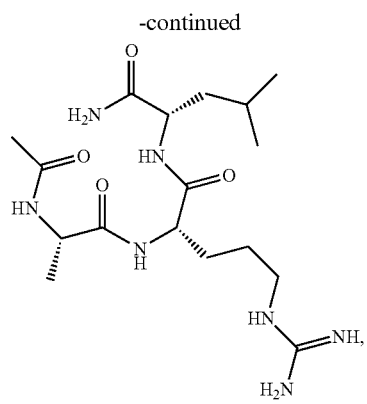
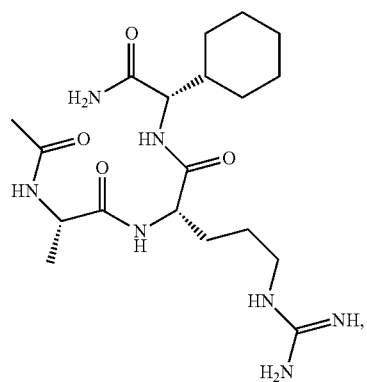
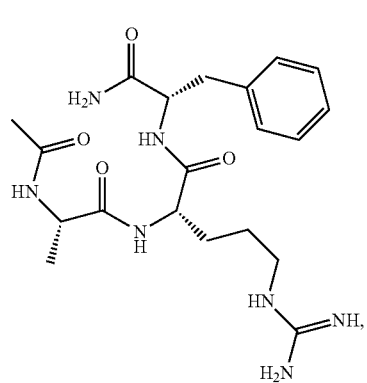
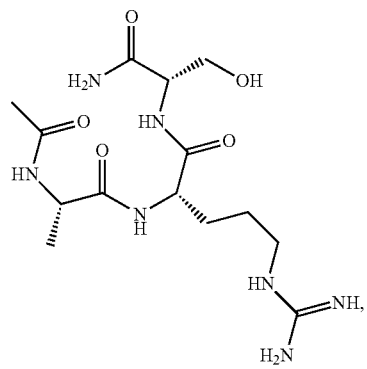

103
-continued
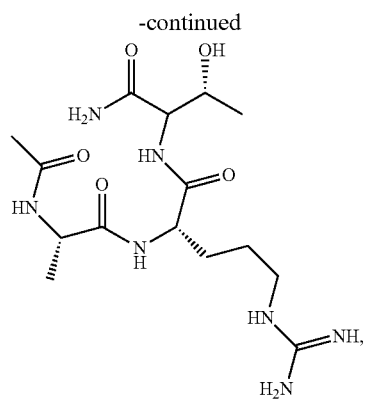
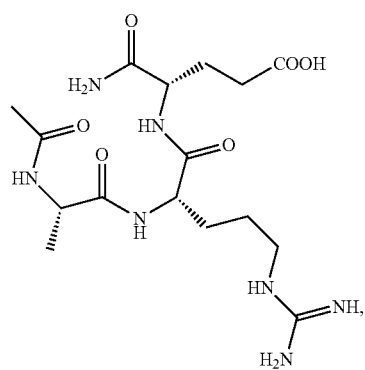
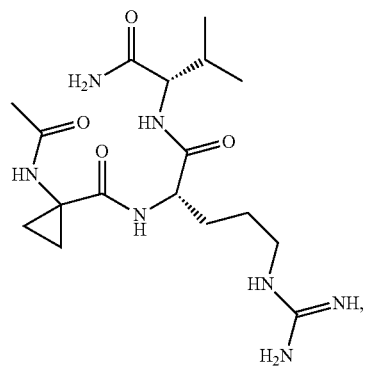
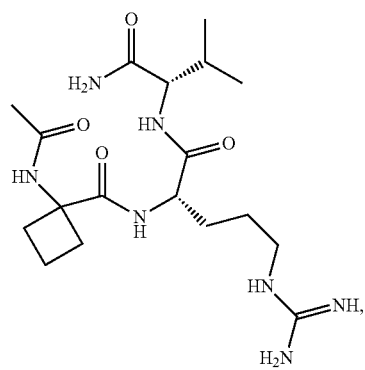
104
-continued
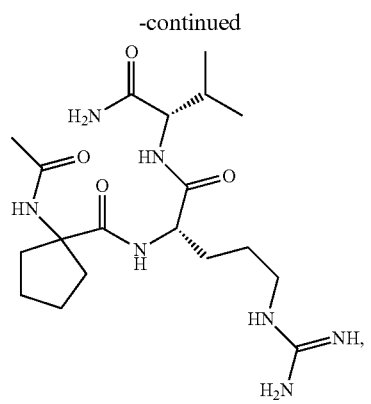
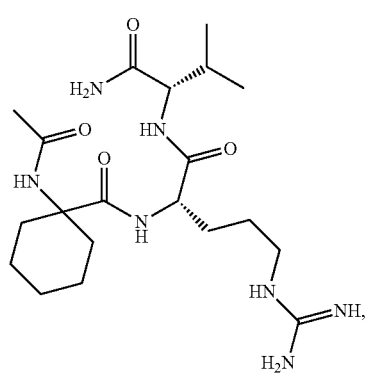
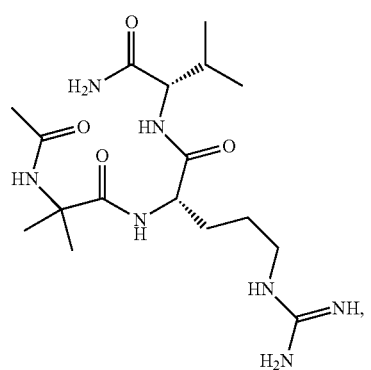
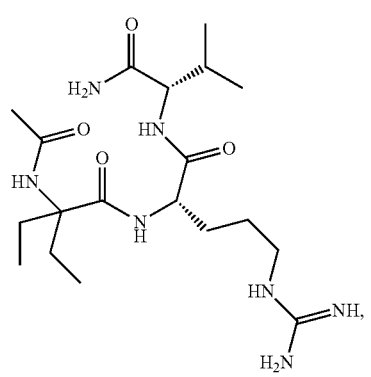

105
-continued
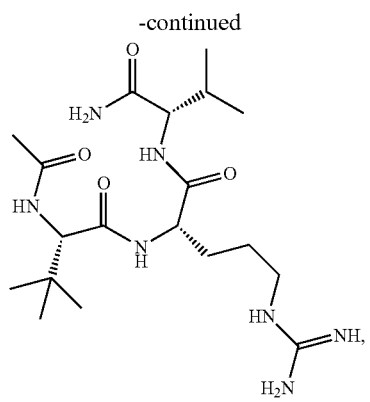
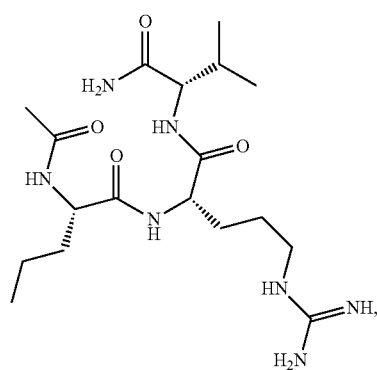
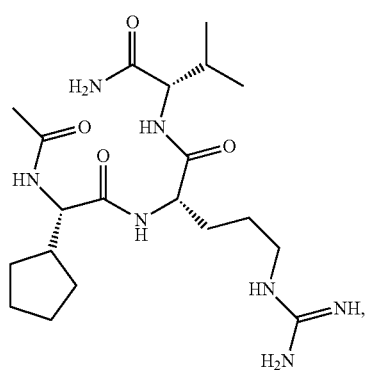
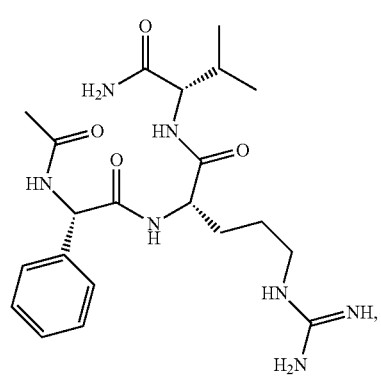
106
-continued
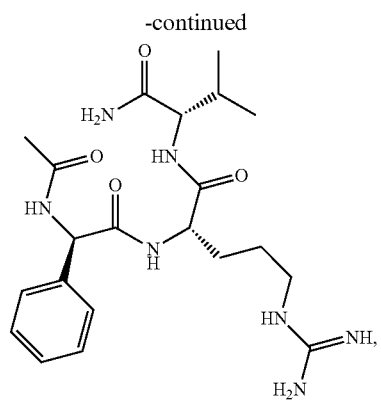
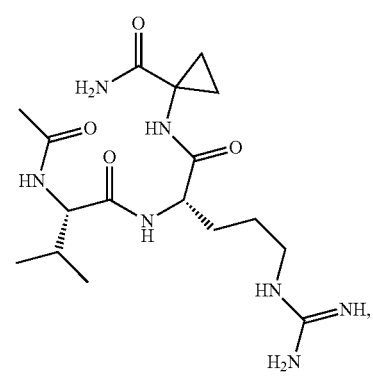
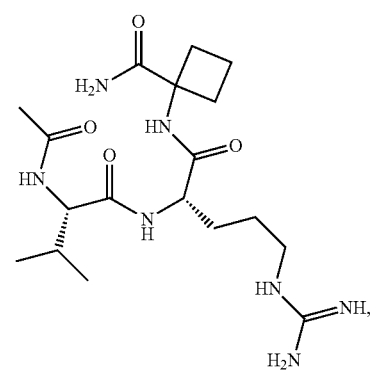
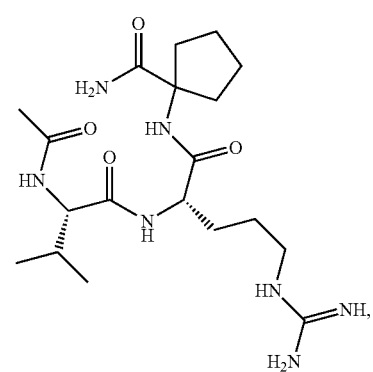

107
-continued
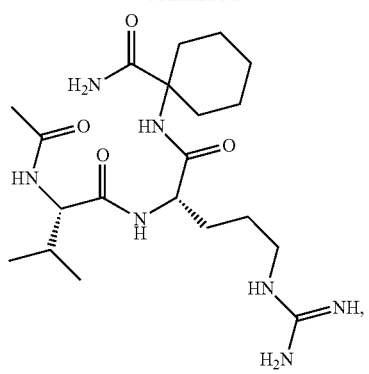
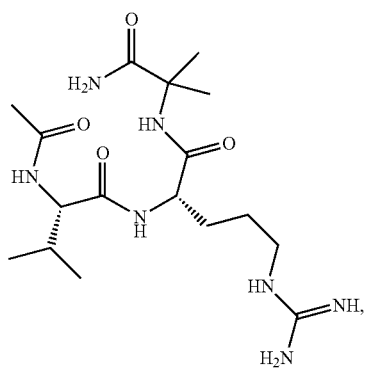
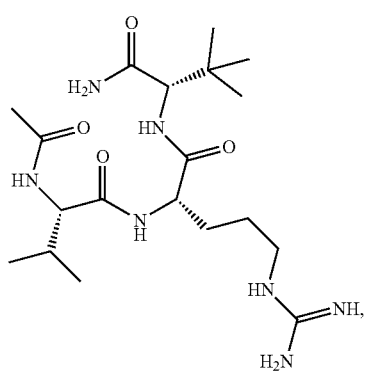
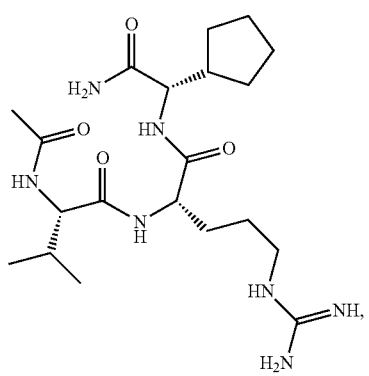
108
-continued
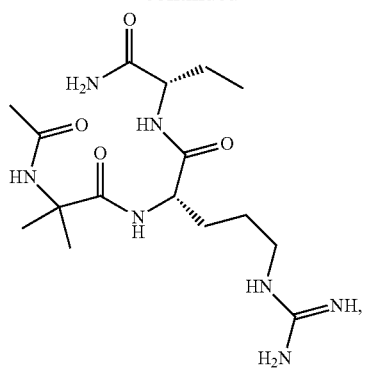
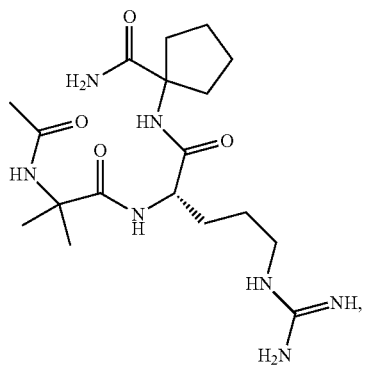
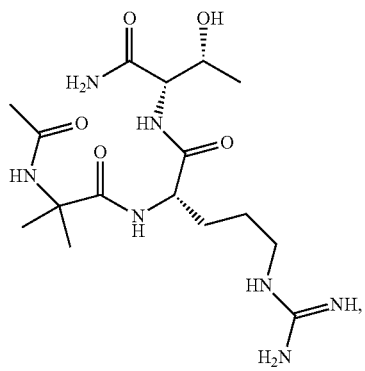
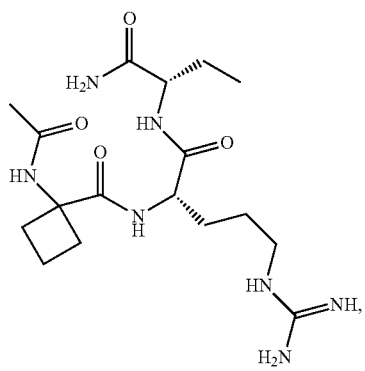

109
-continued
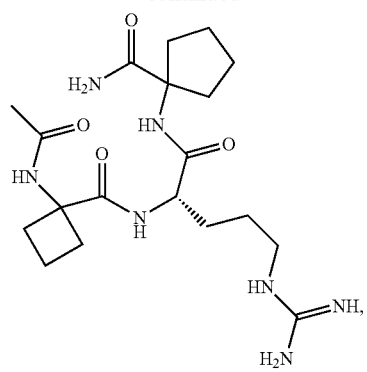
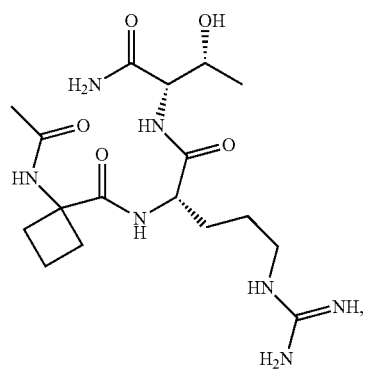
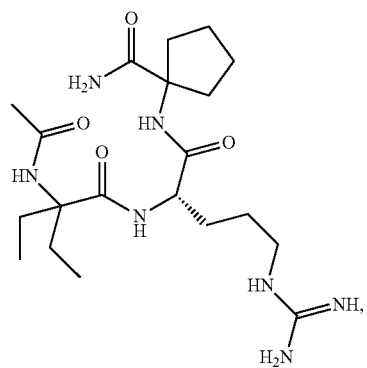
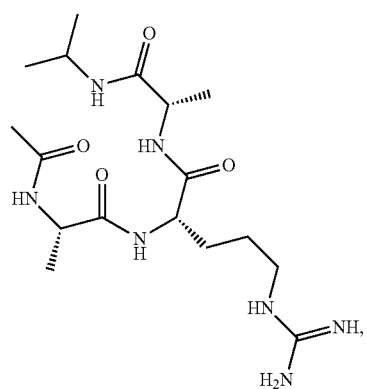
110
-continued
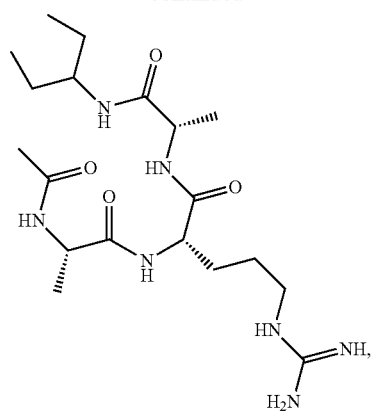
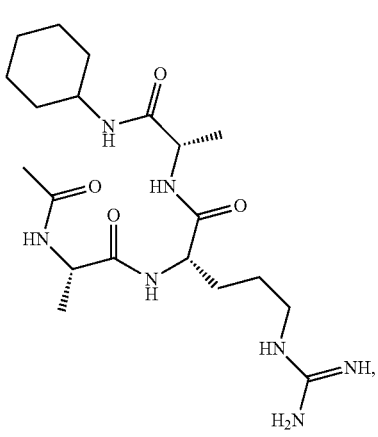
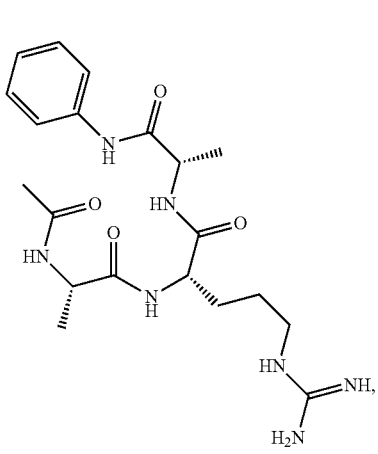
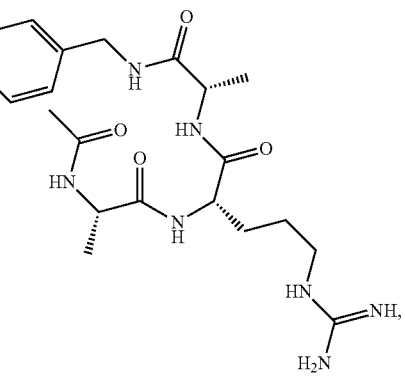

111
-continued
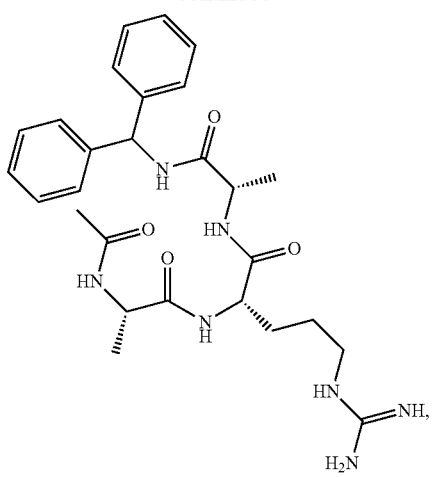
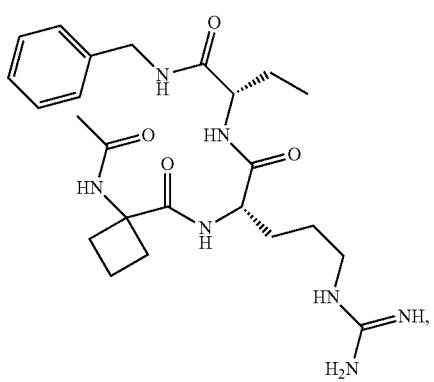
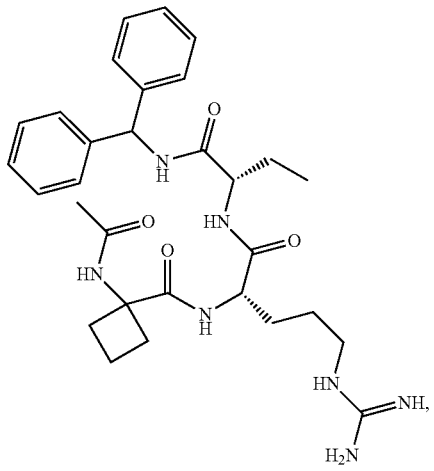
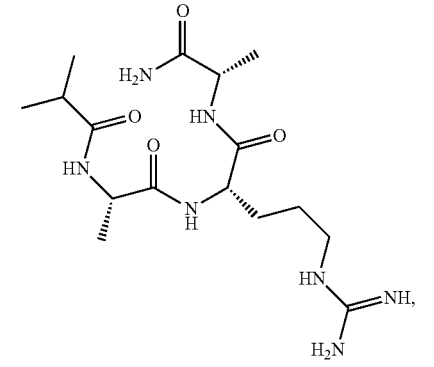
112
-continued
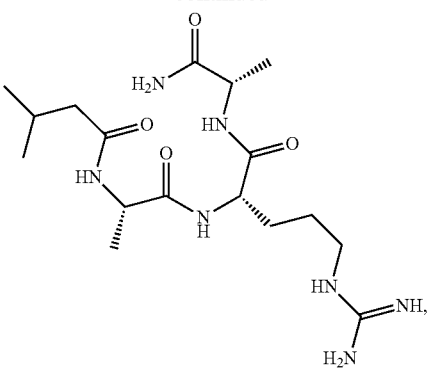
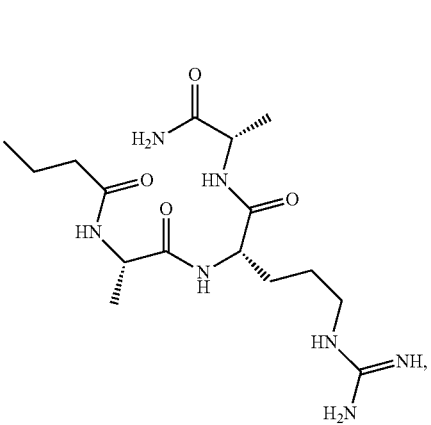
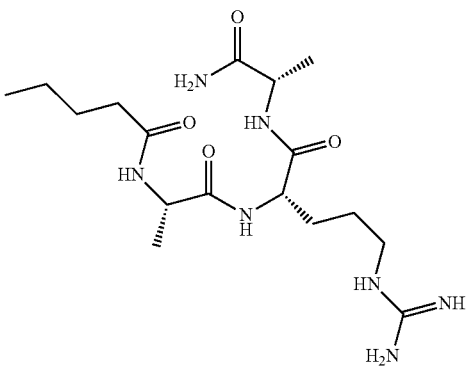
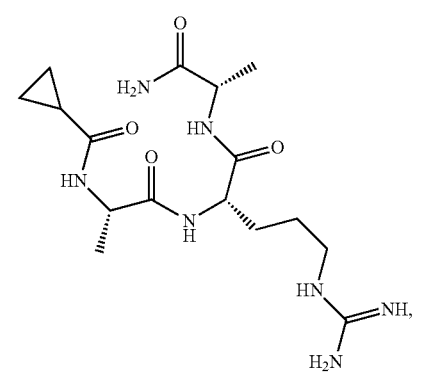

113
-continued
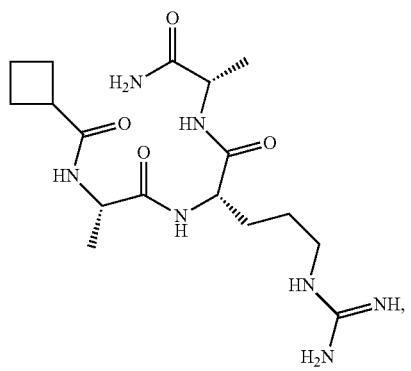
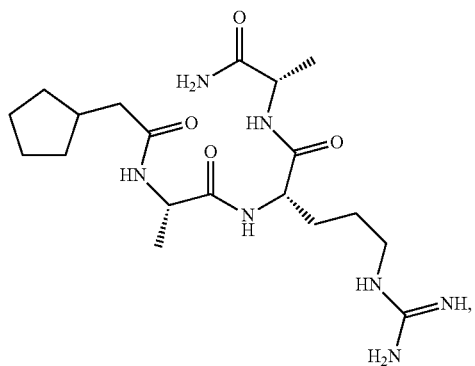
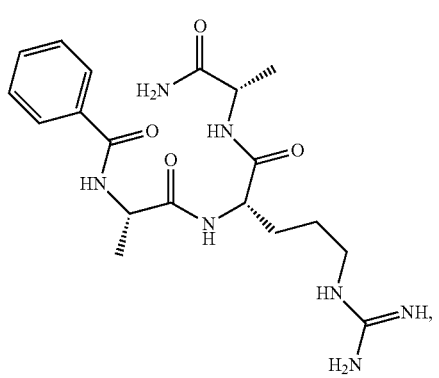
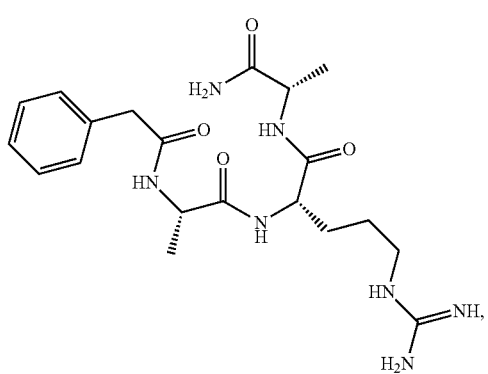
114
-continued
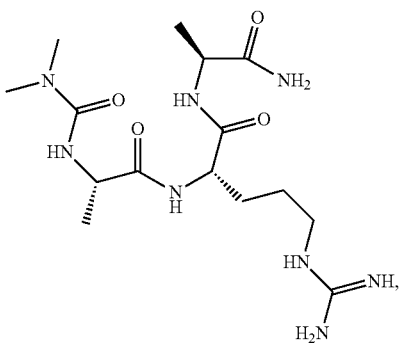
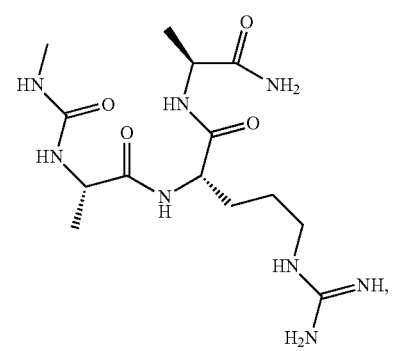
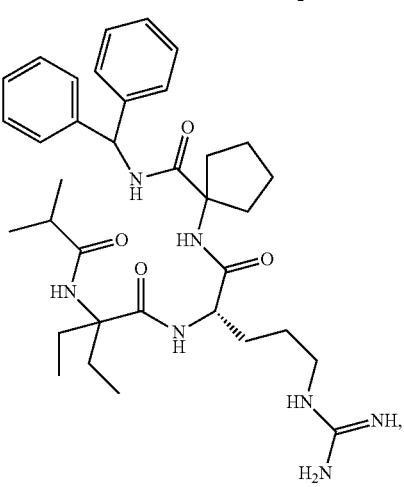
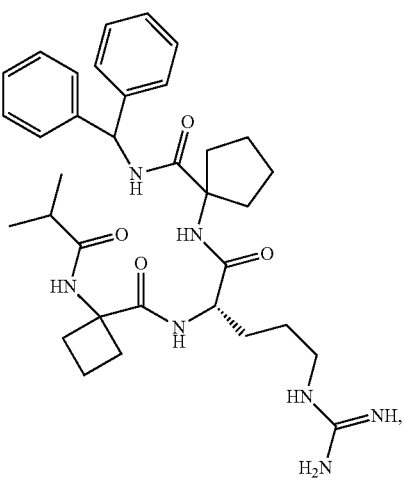

115
-continued
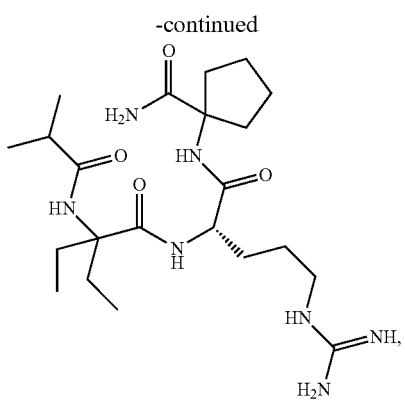
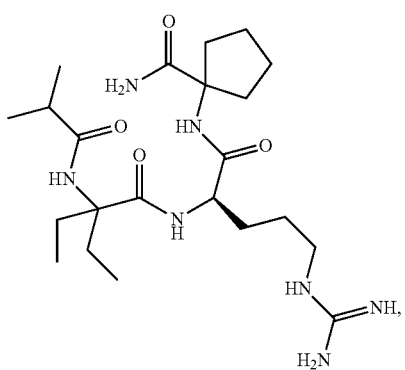
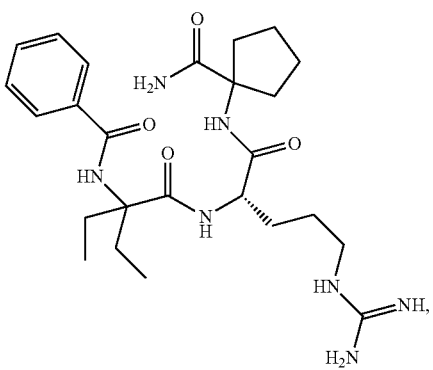
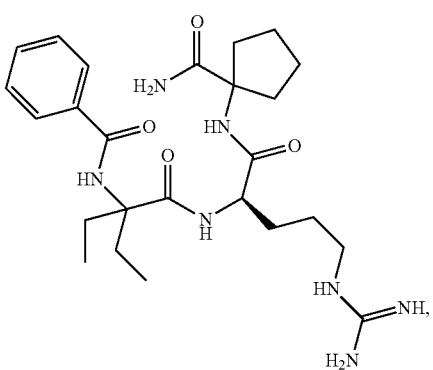
116
-continued
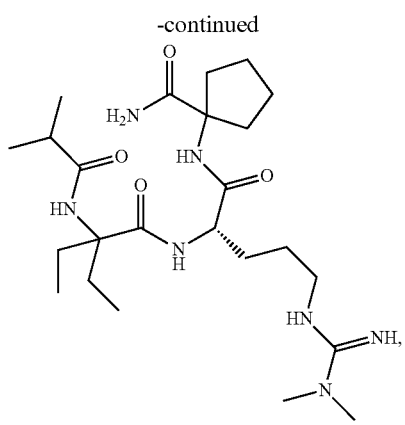
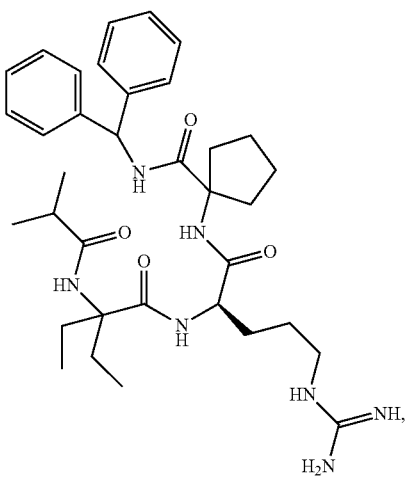
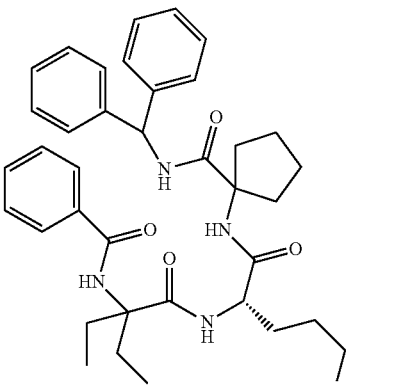

117
-continued
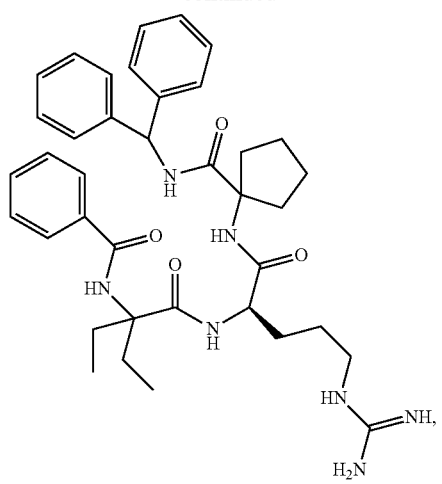
118
-continued
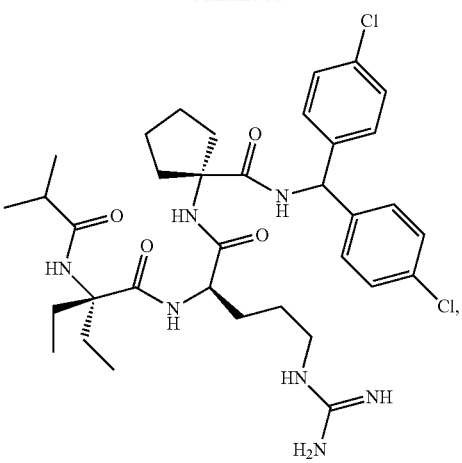
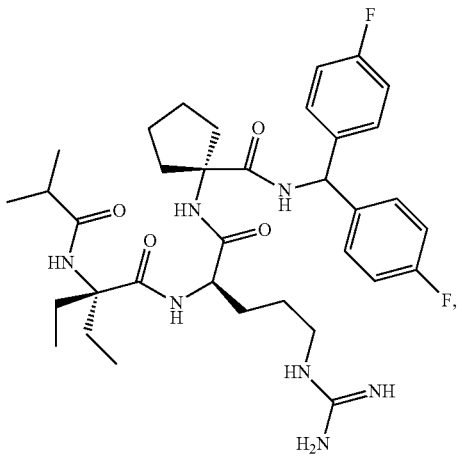
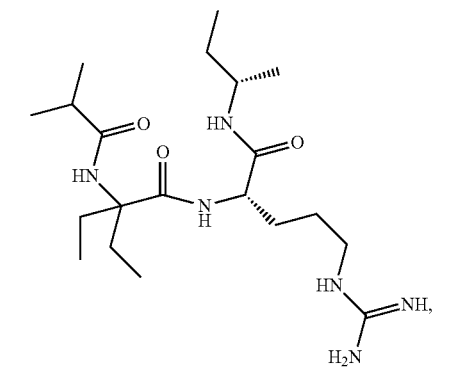
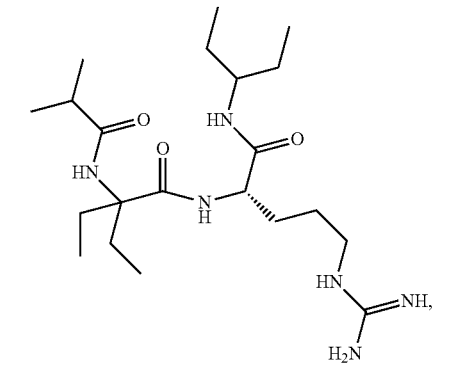

119
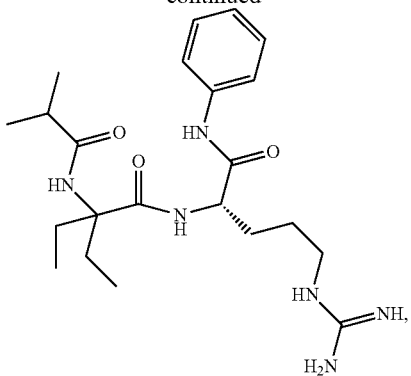
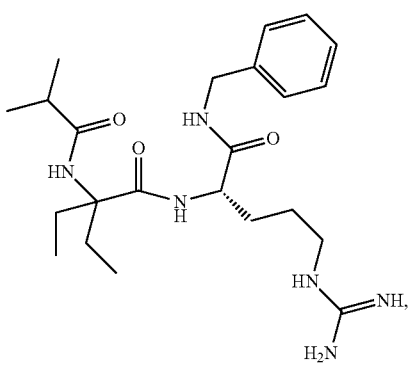
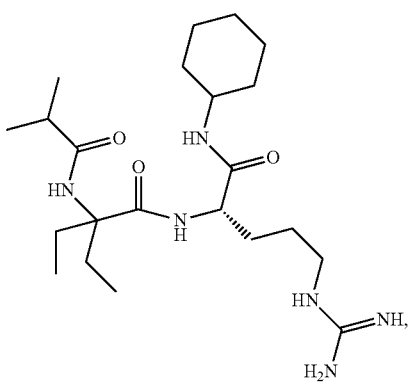
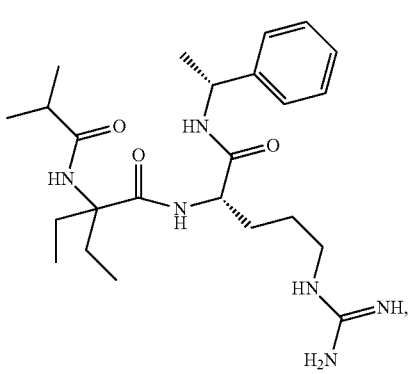
120
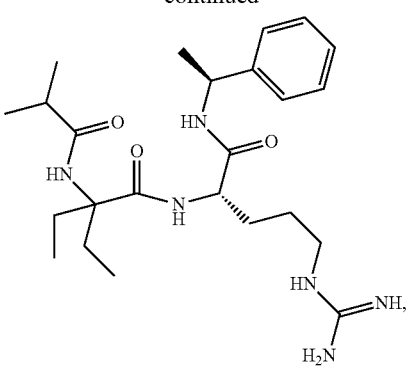
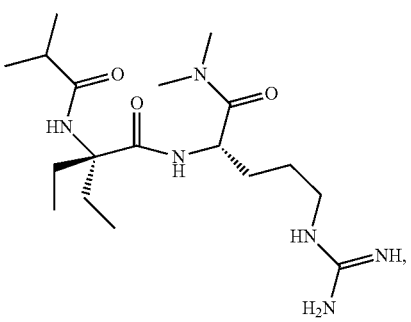
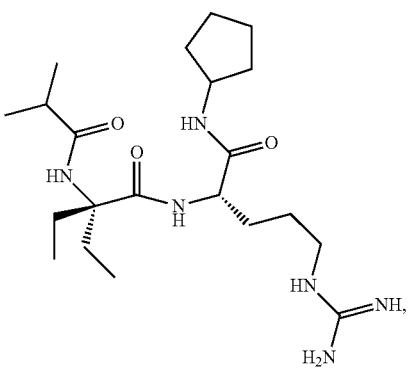
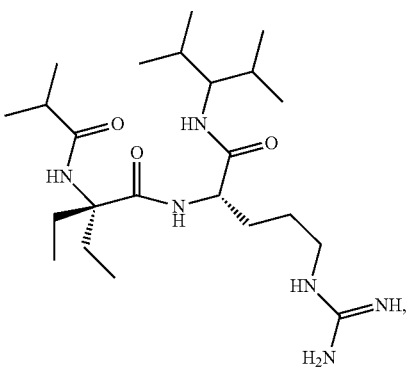

121
-continued
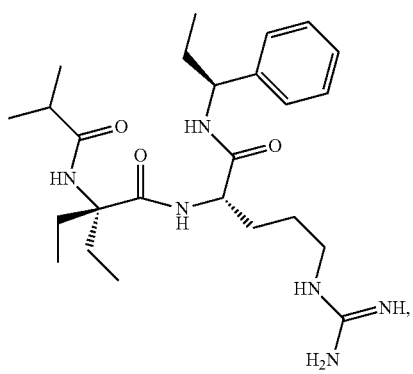
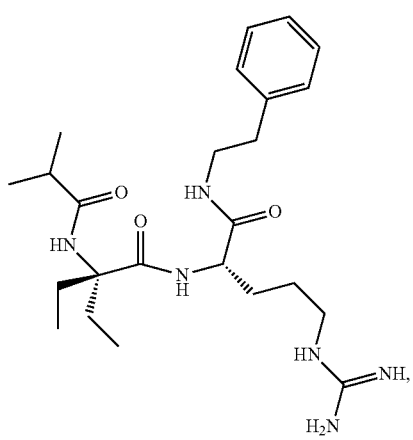
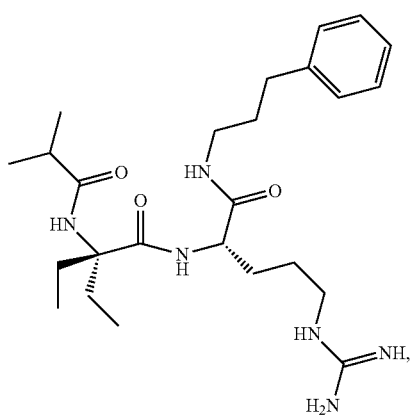
122
-continued
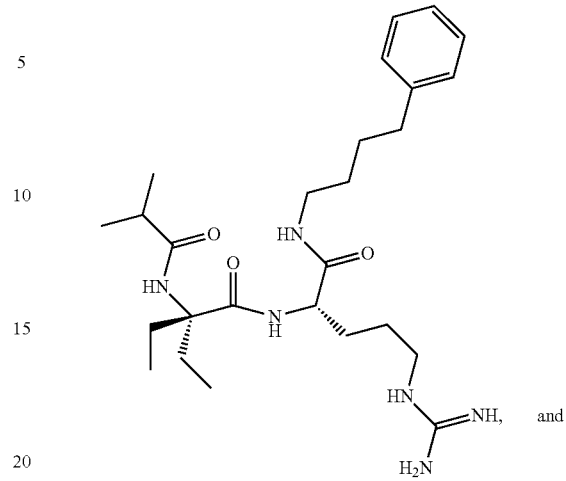
and any mixture thereof.
14. The composition of claim 1 further comprising a chemotherapeutic therapeutic agent useful in the treatment of a cancer.
15. The composition of claim 1 wherein the peptidomimetic compound has a structure
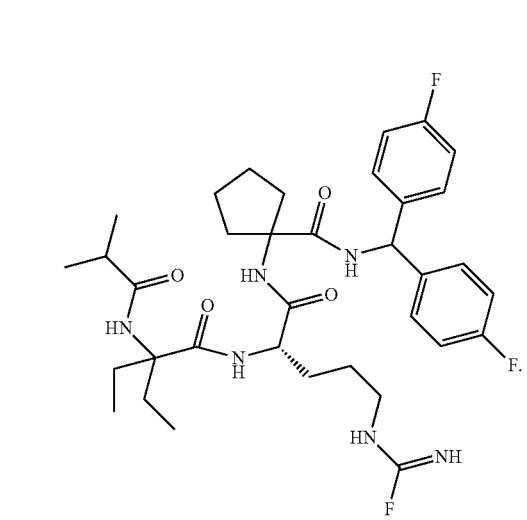 [SMILES: CCC(CC)(NC(=O)C(C)C)C(=O)N[C@@H](CCCNC(=N)F)C(=O)NC1(C(=O)NC(c2ccc(F)cc2)c2ccc(F)cc2)CCCC1]
16. The composition of claim 1 wherein the peptidomimetic compound has a structure 123
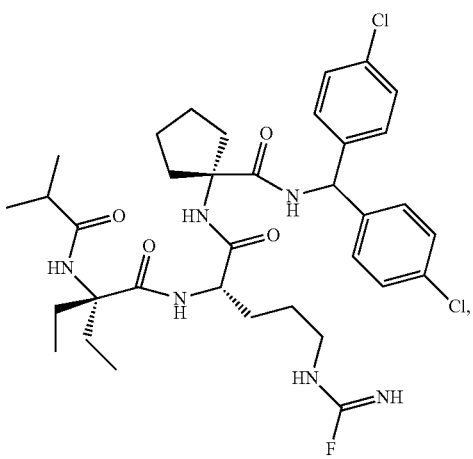
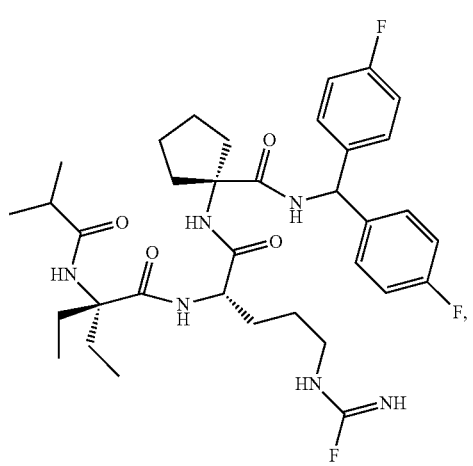
124
-continued
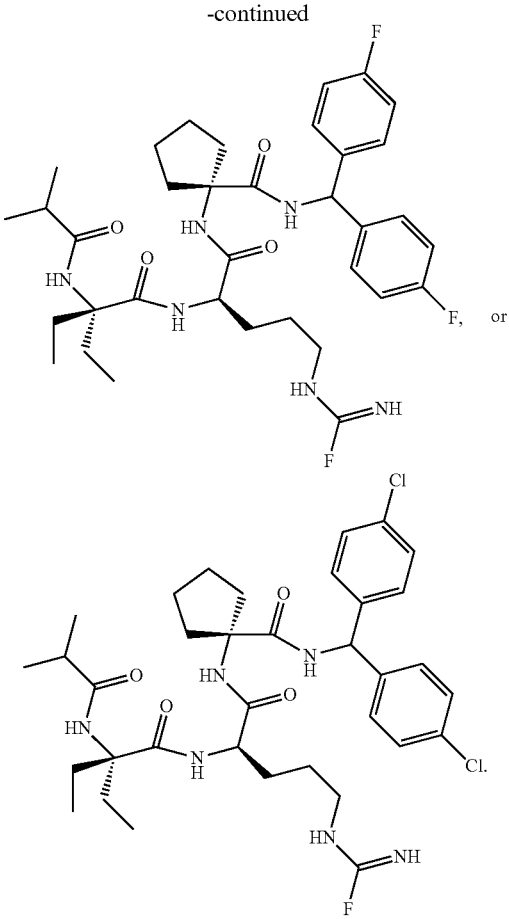
* * * * *